(12) United States Patent
Chelak et al.

(10) Patent No.: US 11,013,902 B2
(45) Date of Patent: May 25, 2021

(54) VASCULAR ACCESS SITE MANAGEMENT SYSTEM

(71) Applicant: NP Medical Inc., Clinton, MA (US)

(72) Inventors: Todd M. Chelak, Westborough, MA (US); John Damarati, Marlborough, MA (US); Nicholas Dennis, Sterling, MA (US); Nicholas Illsley, Sterling, MA (US)

(73) Assignee: NP MEDICAL INC., Clinton, MA (US)

( * ) Notice: Subject to any disclaimer, the term of this patent is extended or adjusted under 35 U.S.C. 154(b) by 57 days.

(21) Appl. No.: 16/298,501

(22) Filed: Mar. 11, 2019

(65) Prior Publication Data

US 2019/0275297 A1    Sep. 12, 2019

Related U.S. Application Data

(60) Provisional application No. 62/641,649, filed on Mar. 12, 2018.

(51) Int. Cl.
*A61M 39/02* (2006.01)
*A61M 39/10* (2006.01)
(Continued)

(52) U.S. Cl.
CPC ........ *A61M 39/0247* (2013.01); *A61M 25/02* (2013.01); *A61M 39/10* (2013.01);
(Continued)

(58) Field of Classification Search
CPC .......... A61M 2039/229; A61M 39/223; A61M 2039/224; A61M 39/0247;
(Continued)

(56) References Cited

U.S. PATENT DOCUMENTS 4,106,491 A * 8/1978 Guerra ............... A61B 5/15003
251/149.2
4,123,091 A * 10/1978 Cosentino ........... F16L 37/0847
285/307
(Continued)

FOREIGN PATENT DOCUMENTS

EP        0422631 A1    4/1991
WO   2000/06230 A1    2/2000
(Continued)

OTHER PUBLICATIONS

International Search Report for Application No. PCT/US2019/021563 dated Jun. 21, 2019, pp. 1-3.
(Continued)

*Primary Examiner* — Brandy S Lee
*Assistant Examiner* — Hong-Van N Trinh
(74) *Attorney, Agent, or Firm* — McCarter & English, LLP; Jonathan C. Lovely, Esq.

(57) ABSTRACT

A vascular access site management system includes a stabilization body and a flow housing that is rotatable relative to the stabilization body. The flow housing may have a flow path extending through it to allow fluids to be introduced into or extracted from a patient via a catheter connected to the vascular access site management system. The vascular access site management system may also include a needle free connector fluidly connected to the flow housing via a section of tubing.

25 Claims, 36 Drawing Sheets

(51) Int. Cl.
*A61M 25/02* (2006.01)
*A61M 39/00* (2006.01)

(52) U.S. Cl.
CPC .............. *A61M 2025/028* (2013.01); *A61M 2039/0036* (2013.01); *A61M 2039/027* (2013.01); *A61M 2039/0258* (2013.01); *A61M 2039/0261* (2013.01); *A61M 2039/0273* (2013.01); *A61M 2039/0282* (2013.01)

(58) Field of Classification Search
CPC .......... A61M 2039/0282; A61M 25/02; A61M 2025/0253; A61M 2025/026; A61M 2025/0266; A61M 2025/0273; A61M 2025/028; A61M 2025/024; A61M 2025/0246; A61M 39/10; A61M 2025/0286; A61M 39/02; A61M 39/0208; A61M 2039/0273; A61M 2039/0276; A61M 2025/0206; A61M 2025/0213; A61M 2025/0233; A61M 2039/0223; A61M 2039/1027; A61M 2039/0261; A61M 2039/0258; A61M 5/425; A61M 2005/1586; A61M 2005/1587; A61M 2039/1033; A61M 2209/088; A61M 39/1011; A61M 5/1418; A61M 25/0097; A61M 39/1055; A61M 2039/0036; A61M 2309/0261; A61M 2039/027; A61M 2309/0273

See application file for complete search history.

(56) References Cited

U.S. PATENT DOCUMENTS

| | | | |
|---|---|---|---|
| 4,569,675 A * | 2/1986 | Prosl | A61M 39/0208 128/DIG. 26 |
| 4,946,448 A | 8/1990 | Richmond | |
| 5,139,483 A * | 8/1992 | Ryan | A61M 39/1011 604/533 |
| 5,205,834 A * | 4/1993 | Moorehead | A61M 39/22 137/493.9 |
| 5,354,282 A | 10/1994 | Bierman | |
| 5,693,025 A * | 12/1997 | Stevens | A61M 39/0613 604/167.03 |
| 5,707,348 A | 1/1998 | Krogh | |
| 5,865,808 A * | 2/1999 | Corn | A61M 25/02 604/174 |
| 6,086,564 A | 7/2000 | McLaughlin | |
| 6,736,797 B1 * | 5/2004 | Larsen | A61M 5/158 604/167.05 |
| 8,585,655 B2 | 11/2013 | Bierman | |
| 8,790,311 B2 * | 7/2014 | Gym | A61F 13/0259 604/180 |
| 8,827,959 B2 | 9/2014 | Wright et al. | |
| 9,017,290 B2 | 4/2015 | Peters et al. | |
| 9,545,502 B2 | 1/2017 | Maseda et al. | |
| 9,642,987 B2 | 5/2017 | Bierman et al. | |
| 9,827,398 B2 * | 11/2017 | White | A61M 5/158 |
| 2006/0270994 A1 | 11/2006 | Bierman | |
| 2008/0269687 A1 * | 10/2008 | Chong | A61L 27/28 604/180 |
| 2010/0179481 A1 * | 7/2010 | Bierman | A61M 25/02 604/177 |
| 2010/0298777 A1 | 11/2010 | Nishtala | |
| 2011/0106014 A1 | 5/2011 | Helm, Jr. | |
| 2011/0257600 A1 | 10/2011 | Kessler | |
| 2012/0232490 A1 | 9/2012 | Andino | |
| 2012/0271240 A1 | 10/2012 | Andino et al. | |
| 2014/0276542 A1 | 9/2014 | Ciccone | |
| 2018/0140821 A1 * | 5/2018 | Purdy | A61M 39/105 |
| 2019/0160275 A1 * | 5/2019 | Funk | A61M 5/1418 |

FOREIGN PATENT DOCUMENTS

| | | |
|---|---|---|
| WO | 2002/096494 A1 | 12/2002 |
| WO | 2009/032008 A2 | 3/2009 |
| WO | 2010/132837 A1 | 11/2010 |

OTHER PUBLICATIONS

Written Opinion of the International Search Authority for Application No. PCT/US2019/021563 dated Jun. 21, 2019, pp. 1-3.

* cited by examiner

VASCULAR ACCESS SITE MANAGEMENT SYSTEM

PRIORITY

This application claims priority from U.S. Provisional Application No. 62/641,649 filed Mar. 12, 2018, entitled "Vascular Access Site Management System," and naming Todd Chelak, John Damarati, Nicholas Dennis and Nicholas Illsley as inventors, the disclosure of which is incorporated herein, in its entirety, by reference.

RELATED UNITED STATES APPLICATIONS

This patent application is related to co-pending U.S. patent application Ser. No. 16/298,175, entitled "Vascular Access Site Management System," filed on even date herewith, and naming Todd Chelak, John Damarati, Nicholas Dennis and Nicholas Illsley as inventors, the disclosure of which is incorporated herein, in its entirety, by reference.

TECHNICAL FIELD

The present invention relates to vascular access sites, and more particularly to devices and systems that manage a vascular access site inclusive of an associated indwelling catheter such as a peripheral intravenous (IV) catheter.

BACKGROUND ART

In instances in which a patient will need regular administration of fluid or medications (or regular withdrawal of fluids/blood), catheters are often inserted into the patient and used to administer the fluids/medications. The catheter may remain in the patient for extended periods of time (several hours to several days or longer). Additionally, an extension tube may be connected to the catheter to facilitate use of the catheter and connection of a medical implement (e.g., a syringe). To ensure that the catheter and/or extension tube remain in place and are not accidentally removed, some prior art systems secure the catheter and/or extension tube to the patient using tape or similar adhesive materials (e.g., a film dressing).

Tapes and adhesive film dressings can be problematic in that they may not firmly secure the catheter in place, which can lead to local trauma to the vein and a medical condition referred to as phlebitis requiring removal of the catheter. Additionally, in some instances, the manner in which the tape is applied and the positioning/location of the catheter and/or extension tube may cause the catheter and/or extension tube to be bent. This, in turn, increases the risk of kinking (which can reduce/stop flow through the catheter and/or extension tube) and makes it more difficult to connect the medical implement required to introduce the fluid/medication.

Other prior art systems attempt to manage the extension set tubing and include various ways to secure the indwelling IV catheter during the final stages of placement. However, these systems either require cumbersome manipulation of the tubing to fit a desired "J-loop" configuration or present a "hard-wired" configuration that may not adapt to the available space surrounding the insertion site. Additionally, the structure used to secure the catheter to the patient is often a separate component that requires maneuvering of several pieces to reach a final state of deployment. This further burdens the clinician's time and skill level.

SUMMARY OF THE INVENTION

In accordance with one embodiment of the invention, a vascular access site management system for transfer of fluid to and/or from a patient has a stabilization body and a flow housing. The stabilization body may have an inlet, an outlet (e.g., a male luer that may connect to a catheter) configured to be connected to a vascular access device, and an internal fluid path extending through at least a portion the stabilization body and between the inlet and outlet. The stabilization body may also have a stabilization surface located on an underside of the stabilization body to stabilize the vascular access site when on the patient. The flow housing may have a sleeve portion and a pathway portion extending from the sleeve portion. The pathway portion may have a flow path extending through at least a portion of it. The sleeve portion may be rotatably coupled to the stabilization body such that the flow housing is rotatable with respect to the stabilization body. The stabilization base may be oriented at an angle (e.g., between 5 and 10 degrees) with respect to a longitudinal axis of the outlet.

In some embodiments, the flow housing may be able to rotate relative to the stabilization body between a first position and at least a second position. The flow path may be fluidly disconnected from the inlet of the stabilization body when in the first portion, and fluidly connected to the inlet of the stabilization body when in the second position. The system may also include an o-ring located between a portion of the stabilization body and a portion of the flow housing.

On the underside of the stabilization surface, the system may have a first securement portion that secures the vascular access site management system to the patient. The system may also have a second securement portion located on a portion of the underside of the stabilization surface. The second securement portion may further secure the vascular access site management system to the patient. The first securement portion may have a first tack adhesive and the second securement portion may have a second tack adhesive. The second tack adhesive may be stronger than the first tack adhesive. The first securement portion may have a first liner covering the first tack adhesive and the second securement portion may have a second liner covering the second tack adhesive. The liners may be removed prior to securing the vascular access site management system to the patient. Additionally or alternatively the first securement portion may include a gripping and/or conforming structure.

In further embodiments, the system may have a valve mechanism located in the fluid path. The valve mechanism selectively prevents and allows fluid flow through the internal fluid path. The stabilization body may have an inlet body and an outlet body and the valve mechanism may be positioned between the inlet body and outlet body. The valve mechanism may be a two way pressure activated valve that deforms in the presence of a forward pressure within the internal fluid path (e.g., to allow fluid flow around the valve mechanism from the inlet to the outlet). To help support the valve mechanism within the stabilization body, the outlet body may have a plurality of support arms. The valve mechanism may deform over the support arms in the presence of the forward pressure. Additionally or alternatively, the valve mechanism may include a slit extending through it. The slit may open in the presence of a back pressure within the internal fluid path to allow fluid flow through the slit and from the outlet to the inlet. Additionally or alternatively, the pressure required to open the slit may be above the venous pressure of the patient.

In additional embodiments, the system may have a tube with a first end that is fluidly connected to the flow path of the pathway portion and a second end. The device may also have a female luer connector located at the second end of the tube. Alternatively, the inlet of the flow path within the pathway portion may fluidly connect to a medical implement.

To reduce pressure over a vein of the patient, the stabilization body may include a vein relief zone. The vein relief zone may have an adhesive portion that lifts the patient's skin when the vascular access site management system is on the patient. The relief zone may be axially aligned with the outlet of the stabilization body. In some embodiments, the stabilization body may have a protrusion extending from a surface of the stabilization body, and the flow housing may have a recess. The recess may snap over the protrusion such that the protrusion enters the recess to axially secure the flow housing to the stabilization base.

In accordance with further embodiments, a method for managing a vascular access site for transfer of fluid to and/or from a patient includes providing a vascular access site management system. The system may include a stabilization body and a flow housing. The stabilization body may include an inlet, an outlet, and an internal fluid path extending through a portion the stabilization body and between the inlet and outlet. The stabilization body may also have a stabilization surface located on an underside of the stabilization body. The flow housing may have a sleeve portion and a pathway portion extending from the sleeve portion. The pathway portion has a flow path extending through a portion it. The sleeve portion may be rotatably coupled to the stabilization body such that the flow housing is rotatable with respect to the stabilization body.

The method may also include connecting the outlet of the stabilization body to a vascular access device, and placing the stabilization body on the patient. The stabilization surface may stabilize the vascular access site management system on the patient. Once on the patient, the method may then rotate the sleeve portion of the flow housing relative to the stabilization body to a second position. The flow path in the pathway portion may be fluidly disconnected from the inlet of the stabilization body when in the first portion, and fluidly connected to the inlet of the stabilization body when in the second position.

In some embodiments, the system may include a valve mechanism located in the fluid path. The valve mechanism may have a slit through it and may selectively prevent and allow fluid flow through the internal fluid path. For example, the valve mechanism may deform in the presence of a forward pressure within the internal fluid path to allow fluid flow around the valve mechanism from the inlet to the outlet. Additionally or alternatively, the slit may open in the presence of a back pressure within the internal fluid path to allow fluid flow through the slit and from the outlet to the inlet. The vascular access site management system may have a first and second securement portion located on the underside of the stabilization surface. The first and second securement portions may secure the vascular access site management system to the patient.

In accordance with further embodiments, a vascular access site management system includes a stabilization body having a base, and an upper portion having a first end configured to be connected to a vascular access device and a second end configured to receive a medical implement. The stabilization body may also have a flow path connecting the first end and the second end along a substantially linear pathway. At the second end, the device may have a port that may connect with the medical implement. The medical implement may have a distal tip and a passage extending through a portion of the medical implement to the distal tip. The passage allows a medical article to pass through the medical implement. A valve mechanism may be located within the flow path to selectively prevent and allow fluid flow through the flow path. The base may be oriented at an angle (e.g., between 5 and 10 degrees) with respect to an outlet of the system.

The device may also have a first engagement element located on a surface of the vascular access site management system. The first engagement element may engage with a second engagement element located on the medical implement to couple the medical implement with the vascular access site management system and position the distal tip at a predetermined longitudinal position in the flow path (e.g., when coupled to the vascular access site management system). The distal tip may interact with the valve mechanism when in the predetermined longitudinal position to allow passage of the medical article into the vascular access site management system. For example, the distal tip of the medical implement may at least partially open the valve mechanism when in the predetermined longitudinal position. In some embodiments, the valve mechanism may be supported in the vascular access site management system such that the longitudinal movement of an outer portion of the slit toward the first end is minimized.

In some embodiments, the valve mechanism may be a two way pressure activated valve. In such embodiments, the valve mechanism may deform in the presence of a forward pressure within the flow path to allow fluid flow around the valve mechanism from the inlet to the outlet. The upper portion may have a plurality of support arms that support the valve mechanism within the flow housing and the valve mechanism may deform over the support arms in the presence of the forward pressure.

The valve mechanism may have a slit extending through it. The slit may open in the presence of a back pressure within the flow path to allow fluid flow through the slit and toward the second end. The back pressure required to open the slit may be above a venous pressure of the patient, and/or the distal tip of the medical implement may partially open the slit when in the predetermined longitudinal position.

The first engagement element may include at least one protrusion and the second engagement element may include at least one recess. The protrusion(s) may enter the recess (es) when the medical implement is connected to the vascular access site management system. Additionally or alternatively, the first engagement element may include at least one recess and the second engagement element may include at least one protrusion. Similarly, the at least one protrusion may enter the at least one recess when the medical implement is connected to the vascular access site management system. The medical implement may have at least one flexible arm, and the second engagement element may be on the at least one flexible arm.

In further embodiments, the vascular access site management system may include a septum located within the port. The septum normally obstructs the port, and at least a portion of the medical implement may extend through the septum when connected to the vascular access site management system. For example, the septum may include a slit extending through it, and the distal tip of the medical implement may open and extend through the slit when the medical implement is connected to the vascular access site management system.

Additional embodiments of the vascular access site management system may have a flow housing with a sleeve portion and a pathway portion extending from the sleeve portion. The pathway portion may have a fluid path extending through at least a portion of the pathway portion, and the sleeve portion may be rotatably coupled to the upper portion of the stabilization body such that the flow housing is rotatable with respect to the stabilization body. The flow housing may rotate with respect to the stabilization body between a first position, a second position and, perhaps, a third position. The fluid path may be in fluid communication with the flow path of the upper portion when the sleeve portion is in the first position and/or the third position, and fluidly disconnected when in the second position. The upper portion may have a first and second hole extending through a wall of the upper portion. The first hole may fluidly connect the fluid path and the flow path when the sleeve portion is in the first position, and the second hole may fluidly connect the fluid path and the flow path when the sleeve portion is in the third position.

Further embodiments may include a tube having a first end and a second end. The first end may be fluidly connected to an inlet of the vascular access site management system and/or there may be a needle free connector located at the second end of the tube. The upper portion may include a male luer lock connector that may be connected to a catheter/or alternatively an access device such as a needleless connector. Additionally or alternatively, the upper portion may have a contact surface within the flow path. The contact surface may contact an outer surface of the medical implement during connection of the medical implement to prevent further longitudinal movement of the distal tip within the flow path and/or radially align the distal tip with the flow path. The upper portion may also have a crushable or deformable guide rib within the flow path to keep the distal tip concentric within the flow path during connection of the medical implement.

In accordance with additional embodiments, a method for managing a vascular access site and introducing a medical article includes providing a vascular access site management system with a stabilization body having a base, an upper portion with a first end and a second end, and a flow path connecting the first end and the second end along a substantially linear pathway. The system may also include (1) a port located at the second end of the upper portion of the stabilization body, (2) a valve mechanism located within the flow path that selectively prevents and allows fluid flow through the flow path, and (3) a first engagement element located on a surface of the vascular access site management system. The method may also include connecting a vascular access device to the first end of the upper portion and connecting a medical implement to the port at the second end of the upper portion. During connection, the first engagement element may engage with a second engagement element located on the medical implement. The medical implement may have distal tip and a passage extending through a portion of the medical implement to the distal tip. The distal tip may be positioned at a predetermined longitudinal position in the flow path and may interact with the valve mechanism when the first engagement element is engaged with the second engagement element. The method may then pass a medical article through the passage of the medical implement and into the vascular access site management system. The distal tip of the medical implement may partially open the valve mechanism (e.g., a slit within the valve mechanism) when in the predetermined longitudinal position.

In some embodiments, the method may also include fluidly connecting a second medical implement to an inlet of the system, and transferring fluid through the vascular access site management system, The pressure applied to the valve mechanism by the fluid may deform the valve mechanism to allow fluid flow around the valve mechanism from the inlet to the outlet. Additionally or alternatively, the vascular access site management system may also include a flow housing having a sleeve portion and a pathway portion extending from the sleeve portion. The pathway portion may have a fluid path extending through at least a portion of the pathway portion, and the sleeve portion may be rotatably coupled to the upper portion of the stabilization body. In such embodiments, the method may also include rotating the flow housing from a first position to a second position. The fluid path may be in fluid communication with the flow path of the upper portion when the flow housing is in the second position, and fluidly disconnected when in the first position.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1A:
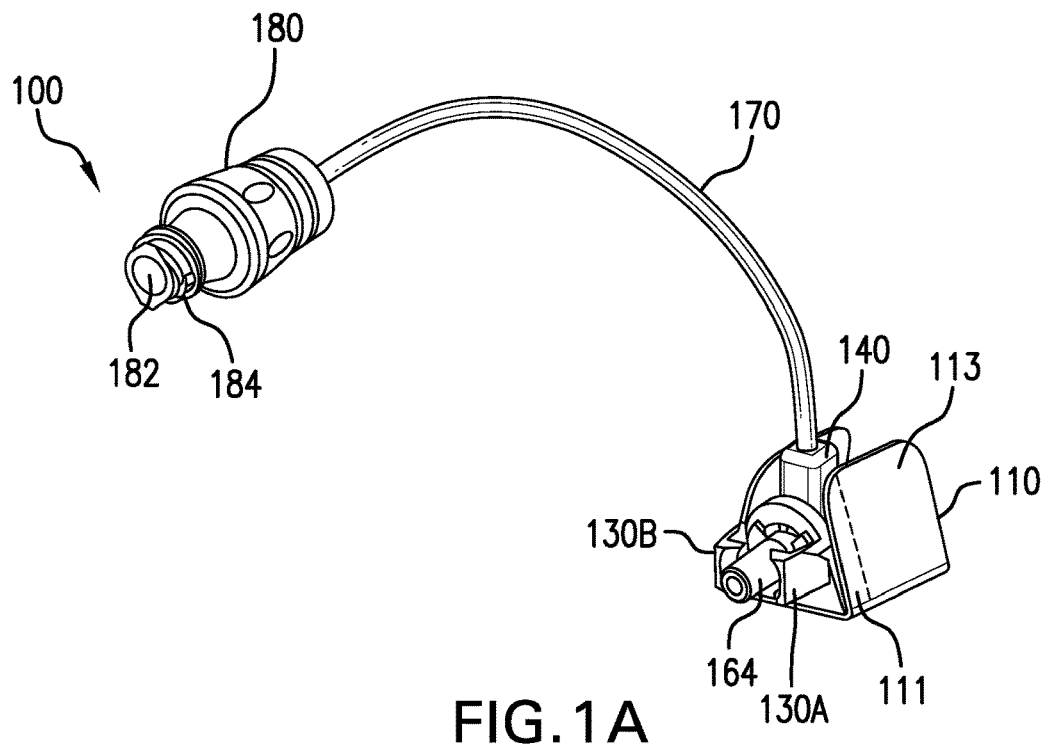
FIGS. 1A-1B schematically show various views of a vascular access site management system in an undeployed state, in accordance with various embodiments of the present invention.
Figure 1B:
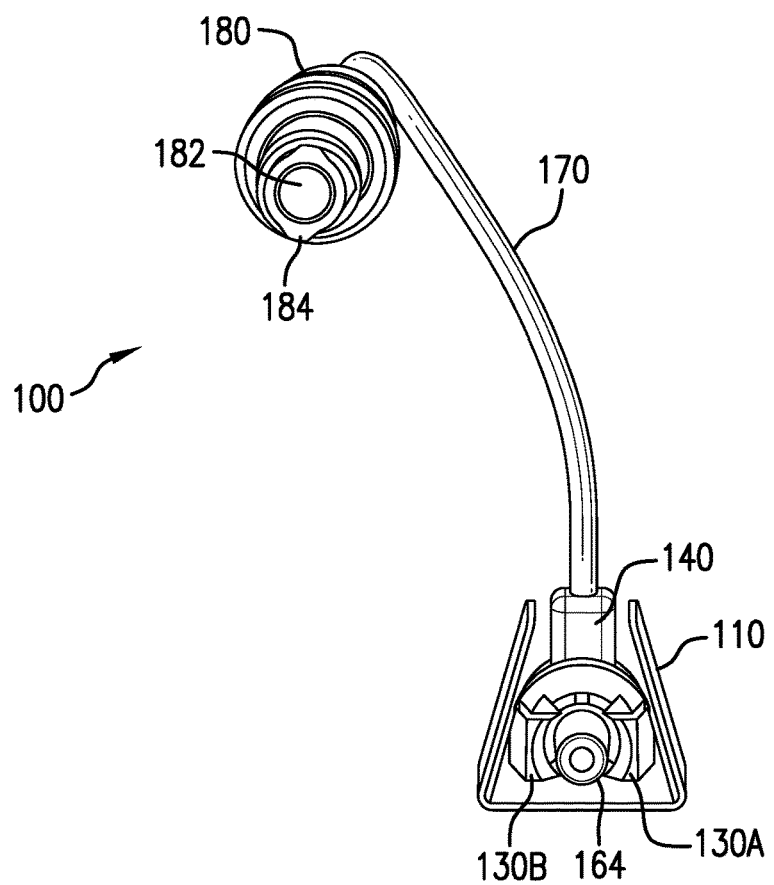

In illustrative embodiments, a vascular access site management system includes a stabilization body and a flow housing that is rotatable relative to the stabilization body. The flow housing may have a flow path extending through it to allow fluids to be introduced to or extracted from a patient via a catheter connected to the vascular access site management system. Additionally, in some embodiments, the vascular access site management system may include a needle free connector or other medical connector fluidly connected to the flow housing via a section of tubing. Details of illustrative embodiments are discussed below.

FIGS. 1A-1D schematically show a vascular access site management system 100 in both an undeployed state (FIGS. 1A and 1B) and a deployed state (FIGS. 1C and 1D), in accordance with some embodiments of the present invention. FIG. 2 shows an exploded view of the vascular access site management system 100. The management system 100 may include a stabilization base 110 (e.g., an adherent substrate) that may be secured to the patient to hold the management system 100 in place during use. More specifically, the stabilization base 110 may include one or more adhesive layers on its underside to secure the management system 100 to the patient. For example, as discussed in greater detail below, the stabilization base may include two sections of adhesive (FIG. 2). The first section 112 may be a light tack adhesive that allows the user to position and re-position the management system 100 as needed. The second section of adhesive 114 may be stronger adhesive that allows the user to firmly secure management system 100 once the system 100 is in place.

The locations of the adhesive sections 112/114 may vary depending on the application. For example, in some embodiments, the first section adhesive 112 may be located at the leading end (e.g., the end closed to the catheter) of the stabilization base 110 (see FIG. 2), and the second section 114 of adhesive may be located on the remainder of the underside of the stabilization base 110. However, in other embodiments, the first section of adhesive 112 may be located at the trailing end of the stabilization base 110 (e.g., the end farthest from the catheter). Additionally or alternatively, the stronger adhesive (e.g., the second section of adhesive 114) may be located on the entire underside of the stabilization base 110 and the first section of adhesive 112 may be located on top of a portion of the stronger adhesive (e.g., one or more areas on the underside of the stabilization base 110 will have multiple layers of adhesive—a layer of stronger adhesive and a layer of lighter tack adhesive on top of the stronger adhesive).

To prevent the sections of adhesive 112/114 from inadvertently sticking to the wrong surface and/or to prevent bacteria and other contamination from sticking to the adhesive, the stabilization base 110 may include one or more liners covering the adhesive. Each of the liners may include a tab so that the liner can be easily removed. For example, the stabilization base 110 can include a first liner 111 for the first section of adhesive 112 and a second liner 113 for the second section of adhesive 114. Alternatively, a single liner may be used for both sections of adhesive 112/114 or each section 112/114 may have multiple liners.

Although any number of adhesives may be used to secure the management system 100 to the patient, the adhesive used for the first section 112 should be easily peelable (e.g., to allow the user to reposition the device 100), but be able to resist shear loads so that the weight of the device 100 and any attached medical implements (e.g., a syringe) do not cause the device 100 to inadvertently move or fall off. The adhesive used for the second section 114 should be strong enough such that the stabilization base 110 and the management system 100 do not peel off the patient's skin during regular movement by the patient (e.g., manipulation of the hand, arm etc.).

In some instances, it may be beneficial for the stabilization base 110 to be folded up prior to use/deployment (see FIGS. 1A and 1B) such that a portion of the stabilization base 110 interfaces with the stabilization body 120 (or flow housing 140). For example, the stabilization base 110 (or the liners 111/113) may be bi-stable such that it is stable in either the folded up position or in the folded down position (e.g., it will not revert to the folded down position when it is folded up and vice versus). Alternatively, the system 100 may include a mechanism that holds that stabilization base 110 in the folded up position (e.g., the body 120 may include a protrusion that extends through the base 110 when in the folded up configuration and prevents the base 110 from returning to the folded down position).

As discussed in greater detail below, when the stabilization base 110 is in the folded up position, the underside of the base 110 provides a surface on each side of the management system 100 where the user may grab and manipulate the device 100. To further improve the user's ability to grip and manipulate the device 100, the release liners 111/113, the adhesive 112/114, or the stabilization base 110 may be a material that deforms in the presence of a pressure such that it conforms to the user's fingers, the shape of the stabilization body 120 and/or flow housing 140.

Figure 4A:
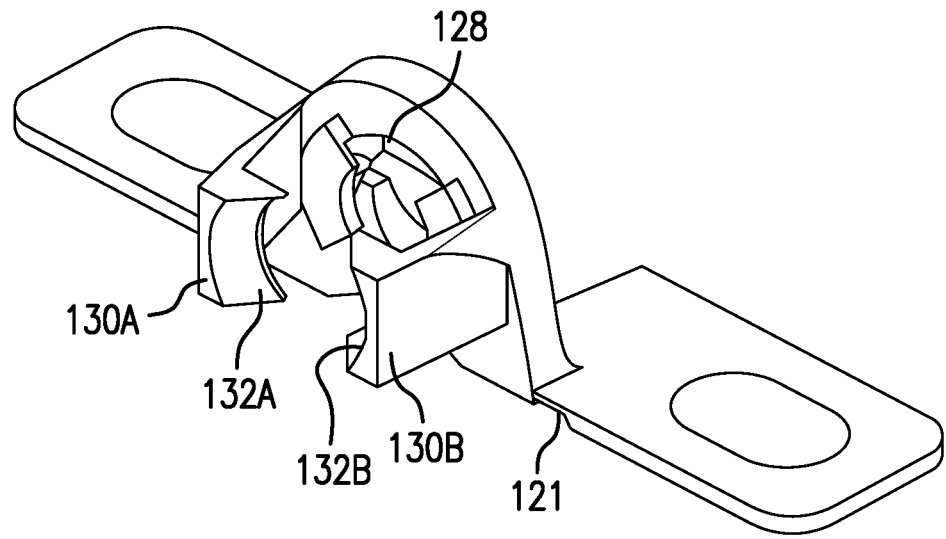
FIG. 4A-4D schematically show a camming mechanism within the vascular access site management system shown in FIGS. 1A-1D, in accordance with some embodiments of the present invention.
Figure 4B:
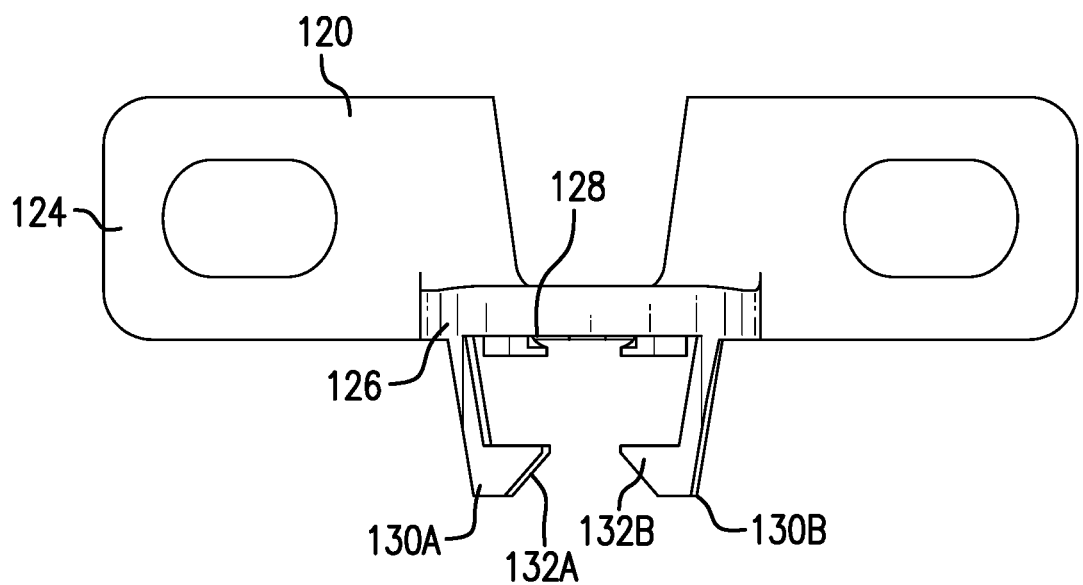
Figure 4C:
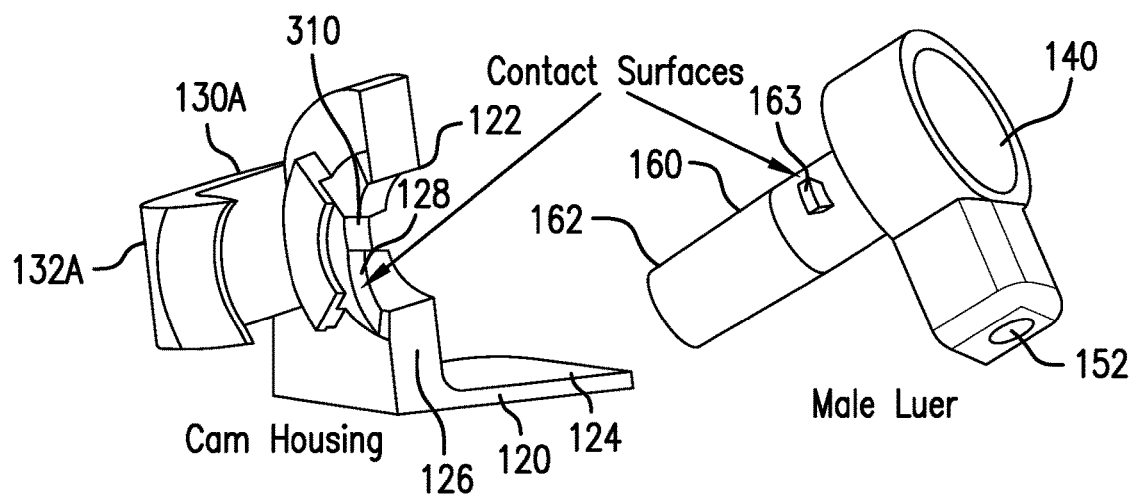
Figure 4D:
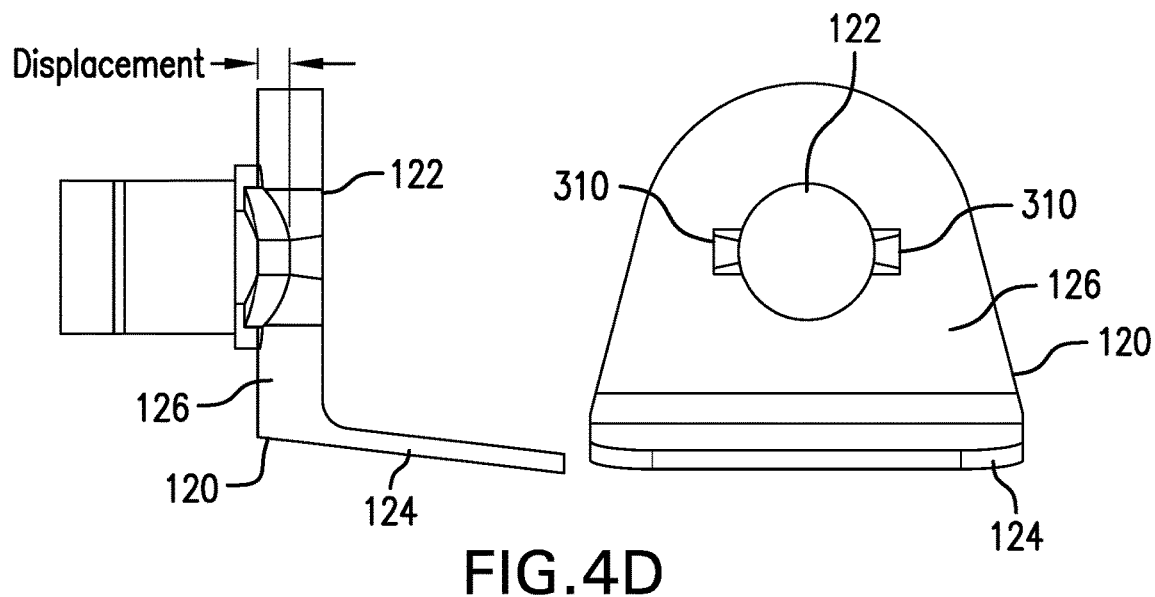

Located on and secured to the stabilization base 110, the management system 100 has a stabilization body 120 with an opening 122 extending through it. For example, the stabilization body 120 may have a bottom portion 124 that is secured to the stabilization base 110 and a proximally extending portion 126 that extends upward from the bottom portion 124 and through which the opening 122 extends. The bottom portion 124 may be secured to the stabilization base 110 in any number ways (e.g., via adhesive, ultrasonic welding, bonding, etc.). In some embodiments, it may be beneficial for the stabilization body 120 to conform to the patient. To that end, the stabilization body 120 may include living hinges 121 (FIGS. 4A and 4B) that allow the bottom portion 124 of the stabilization body 120 to flex (e.g., with respect to portion 126).

As mentioned above, the management system 100 may be connected to a catheter 210 that has been inserted into the patient. To that end, the stabilization body 120 may include a pair of locking arms 130A/130B that extend from the body 120 and toward the catheter 210. Each of the locking arms 130A/130B may have an inwardly projection protrusion 132A/132B that engages with a luer thread 212 on the catheter 210 to lock the catheter 210 in place. For example, during connection of the catheter 210, the user may push the management system 100 against the catheter 210 (while holding the catheter 210 to ensure that it does not move) such that the end of the catheter 210 and the luer thread 212 contact the locking arms 130A/B. As additional force is applied by the user, the locking arms 130A/B will begin to flex outward until the luer thread 212 is located between the arms 130A/B, at which point the arms 130A/B will snap back to their original position. Once the arms 130A/B have "snapped" back, the protrusions 132A/B will engage the luer thread 212 and lock the catheter 210 to the management system 100.

Figure 2:
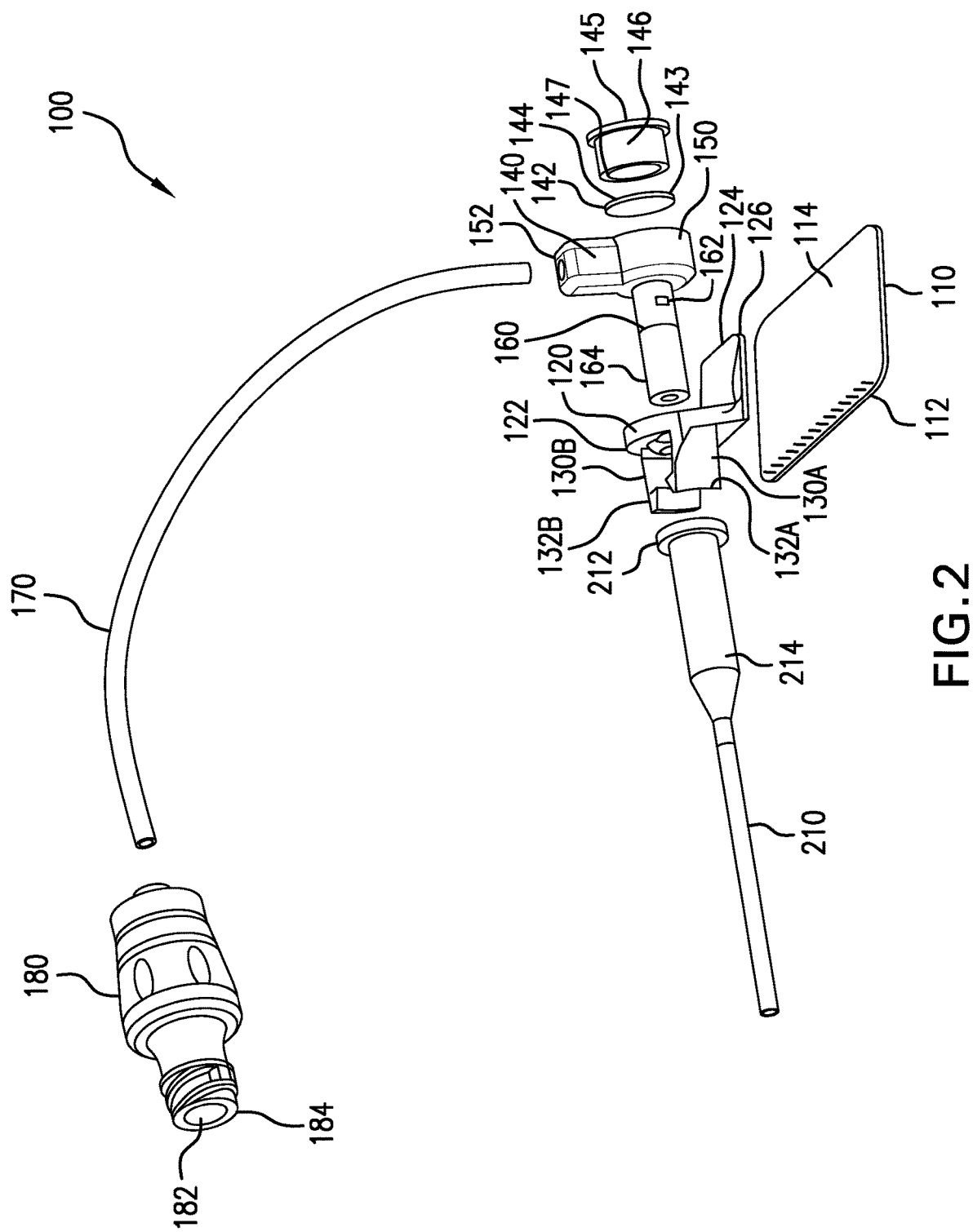
FIG. 2 schematically shows an exploded view of the vascular access site management system shown in FIGS. 1A-1D, in accordance with some embodiments of the present invention.
Figure 3:
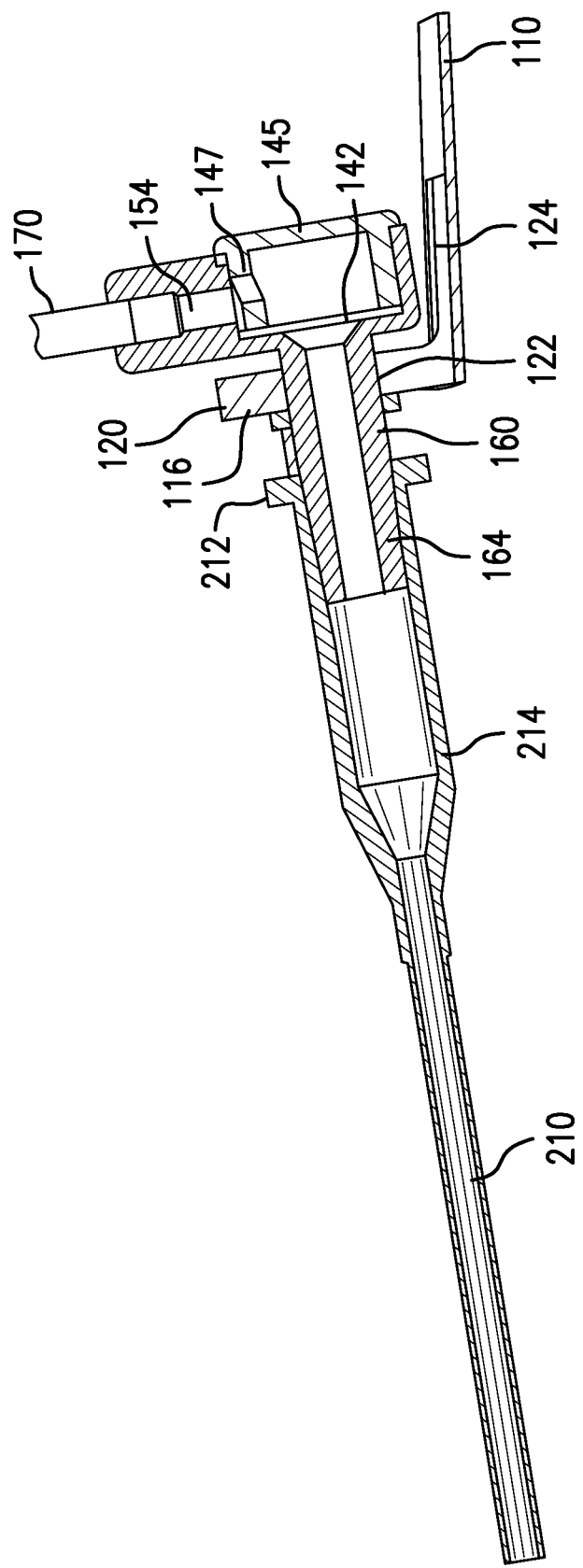
FIG. 3 schematically shows a cross-sectional view of the vascular access site management system shown in FIGS. 1A-1D, in accordance with some embodiments of the present invention.

As best shown in FIGS. 2 and 3, the management system 100 may also include a flow housing 140 that essentially acts as the hub of the management system 100, and through which fluid being transferred to/from the patient flows. The flow housing 140 includes a main housing 150 and a housing extension 160 that extends outward from the main housing 150 and through the opening 122 in the stabilization body 120. At least a portion of the housing extension 160 may be a male luer (e.g., male luer portion 164) that connects with the catheter 210 during use. The extension 160 and/or the opening 122 may be sized such that the extension 160 and, thus the flow housing 140 is free to rotate with respect to stabilization body 120. Additionally, as discussed in greater detail below, the extension 160 may have one or more protrusions 162 that interact with a camming surface on the stabilization body 120 to further secure the extension 160 (e.g., the male luer portion 164) to the catheter 210.

The main housing 150 of the flow housing 140 may have a port 152 (e.g., an inlet) that fluidly connects to tubing 170 leading to a needle free connector 180 (discussed in greater detail below). Within the interior of the main housing 150, the flow housing 140 may have an internal fluid path 154 that extends through the body of main housing 150/flow housing 140 and the extension 160. As discussed in greater detail below, during use, fluid may flow through the flow housing 140 as fluid is transferred to the patient. It should be noted that, although much of the discussion herein refers to the port 152 as an inlet, the port 152 also may be used as an outlet. In other words, if fluid is to be drawn from the patient (as opposed to transferred to the patient), the fluid may flow into fluid path 154 via the extension 160 and male luer connector 164, through the internal fluid path 154, and out of the port 152.

In some instances the catheter 210 may extend out of the patient at an angle (e.g., at a 7 degree angle with respect to the patient). To reduce the forces/pressure on the catheter 210, make it easier for the user to connect the catheter 210 to the device 100 and keep the fluid path 154 in line with the catheter 210, the fluid path 154 (e.g., the portion extending through the housing extension 160/male luer) may also be at an acute angle with respect to the surface of the patient. To that end, as shown in FIG. 3, the proximally extending portion 126 may not be perpendicular with respect to the bottom portion 124 of the stabilization base. Rather, it may be angled back slightly to create the acute angle between the fluid path 154 and the surface of the patient's skin. Additionally or alternatively, the portion of the fluid path 154 extending upward through the fluid housing 140 may be not be at a right angle with respect to the portion that extends through the extension 160.

To control fluid flow through the management system 100 and the flow housing 140, the interior of the flow housing 140 may include a valve mechanism 142 within the internal fluid path 154. For example, the flow housing 140 may include a two-way pressure activated valve 142 (PAV) that includes a flat diaphragm 143 with a slit 144. Alternatively, at least a portion of the diaphragm 143 may have a curvature with the slit 144 positioned within the curved portion. The valve mechanism 142 prevents fluid flow through the flow housing 140 (e.g., through the internal fluid path 154) until it is exposed to a large enough pressure to open the slit through the diaphragm 143 (e.g., a cracking pressure). It is important to note that a diaphragm 143 and slit 144 configuration should be chosen such that the patient's venous pressure is below the backward (i.e. proximally-directed) cracking pressure of the valve mechanism 142 to prevent the venous pressure from opening the slit 144/pressure activated valve 142. Additionally, the distally-directed cracking pressure may be different than the proximally-directed cracking pressure.

Although a diaphragm 143 with a slit 144 may achieve the functionality of a two-way pressure activated valve, other two-way PAVs known in the art may also be used within the flow housing 140. Additionally or alternatively, the flow housing 140 may include a one-way PAV valve that only allows a one directional flow through the flow housing 140 (e.g., from the port 152 and towards the catheter 210). For example, in some embodiments, the diaphragm 143 may not have a slit 144 (e.g., it may be a solid diaphragm). In such embodiments, the diaphragm may deform (e.g., it may deform over a protrusion within the flow housing 140) in the presence of a pressure within the flow housing 140 to open the internal fluid path 154 and allow the fluid to flow past the diaphragm and through the flow housing 140.

To secure the valve 142 within the flow housing, the device 100 may include a cap 145 that may be inserted to an open end of the flow housing 140. The cap 145 may have a skirt 146 that extends inward into the interior of the flow housing 140 and traps the valve 142 between the skirt 146 and an inner wall of the flow housing 140. To ensure that the fluid path 154 through the flow housing 140 is not blocked, the cap 145 may include an opening 147 through the skirt 146. In some instances, connection and disconnection of a medical implement to the needle-free connector 180 may cause a pressure increase and/or decrease within the flow housing 140 (e.g., within the fluid path 154). To compensate for these pressure changes and to help prevent blood from being pulled into the fluid path 154 (e.g., past the valve 142), the cap 145 may include a diaphragm or bellows (not shown) that deforms with the changes in pressure. For example, if the pressure within the fluid path 154 increases (e.g., due to connection of the medical implement), the diaphragm or bellows may deform outward with respect to the fluid path 154. Conversely, if the pressure within the fluid path 154 decreases (e.g., upon disconnection of the medical implement) the diaphragm or bellows may deform inward with respect to the fluid path 154 (e.g., into the interior of the flow housing 140).

As noted above, the extension 160 may have one or more protrusions 162 that interact with a camming surface on the stabilization body 120 to further secure the extension 160 (e.g., the male luer portion 164) to the catheter 210. For example, as shown in FIGS. 4A-4D, the stabilization base 120 (e.g., in the proximally extending portion 126) may have slots 310 that allow the protrusions 162 on the extension 160 to pass through the stabilization base 120 (e.g., when the flow housing 140 is in the upright position shown in FIG. 2). The slots 310 provide a diametric interference with the effective diameter of the protrusions 162 such that they provide a one-way, snap-style insertion of the flow housing 140 into the stabilization body 120. This allows for proper initial positioning and capturing of the protrusions 162 relative to the camming surfaces 128 on the stabilization body 120.

Once in place, a camming surface 163 on the protrusions 162 will contact a camming surface 128 on the stabilization body 120. Upon rotation of the flow housing 140 toward the deployed position (see FIGS. 1C and 1B), the camming surface 163 on the protrusions 162 will slide along and advance up the camming surface 128 on the stabilization body 120. This, in turn, will cause the flow housing 140 and extension 160 to move towards the catheter 210 such that the male luer portion 164 of the extension 160 moves further into the female luer of the catheter hub 214. In some embodiments, the protrusions 162/lugs may travel into a detent within the stabilization body 120 to lock the flow housing 140 in the cammed/fully connected position. It is important note that, as discussed above, the catheter 210 is restrained by the pair of locking arms 130A/B and therefore is held in place as the male luer portion 164 is connected.

As mentioned above, the vascular access site management system 100 also includes a needle-free connector 180 that is fluidly connected to the flow housing 140 via a tube 170. The needle-free connector 180 (e.g., a medical valve) is connectable to a medical implement and is used to control fluid flow to and from the patient. Although any number of needle-free connectors 180 or medical valves can be used (e.g., positive displacement valves, negative displacement valves, neutral displacement valves, etc.), some embodiments may use a simple split septum valve. As is known in the art, a split septum valve includes a septum 182 obstructing the inlet 184 of the valve 180. To allow flow through the valve 180, the septum 182 may include an aperture or a slit extending through it. To that end, connection of the medical implement (e.g., a needleless syringe) to the valve 180 deforms the septum, thus opening the aperture/slit. Once connected, the medical implement may transfer fluid to/from the patient. In order to help reduce potential kinking, the tube 170 may be pre-formed with the arcuate/curved shape shown in the figures. For example, the tube 170 may be initially formed in this shape (e.g., prior to assembly) or the tube 170 may take that curved shape during the sterilization process after assembly.

During use, the user (e.g., the medical personnel) may first connect a medical implement to the needle-free connector 180 and flush (e.g., prime) the device 100, for example, with saline. Once the device 100 is flushed/primed, the user may insert the catheter 210 into the patient (e.g., into the patient's arm). It is important to note that prior to inserting the catheter 210, the insertion site should be properly cleaned per acceptable medical practice. Additionally, to preserve the injection site after insertion of the catheter 210, the user may place gauze over the injection site and the location where the management device 100 will be placed.

The user may then connect the catheter 210 to the management device 100. When attaching the catheter 210 and securing the stabilization device 100, the user may grab the stabilization body 120 (or the underside of the stabilization base 110 if it is folded up) and press the device 100 against the catheter 120. As the user presses the device 100 against the catheter 120, the locking arms 130A/B will begin to deform until the catheter 210 (e.g., the thread 212 on the catheter hub 214) snaps into place. At this point, the catheter 210 is, at least partially connected to the male luer connector portion 164 on the extension 160. Once the catheter 210 is attached, the user may then remove the liner 111 on the first section 112 of adhesive and stick the stabilization base 110 to the patient.

Once the first section 112 of adhesive is adhered to the patient, it is desirable to check that the fluid flow through the system 100 and in the vein is acceptable/adequate. To that end, the user may gently inject 1-2 ml of saline into the vein to confirm adequate fluid flow. If the fluid flow is not adequate, the user may adjust the positioning of the catheter 210 within the vein by gently lifting the first section 112 of adhesive to release the system 100 from the patient's skin, and move the catheter 210 forward into the vein while gently injecting another 1-2 ml of saline solution. Once the flow is adequate, the user may, once again, secure the system 100 to the patient's skin using the first section 112 of adhesive. Additionally, if the user is satisfied with the placement, the user may remove the liner 113 for the second section 114 of adhesive to further secure the system 100 to the patient.

Figure 1D:
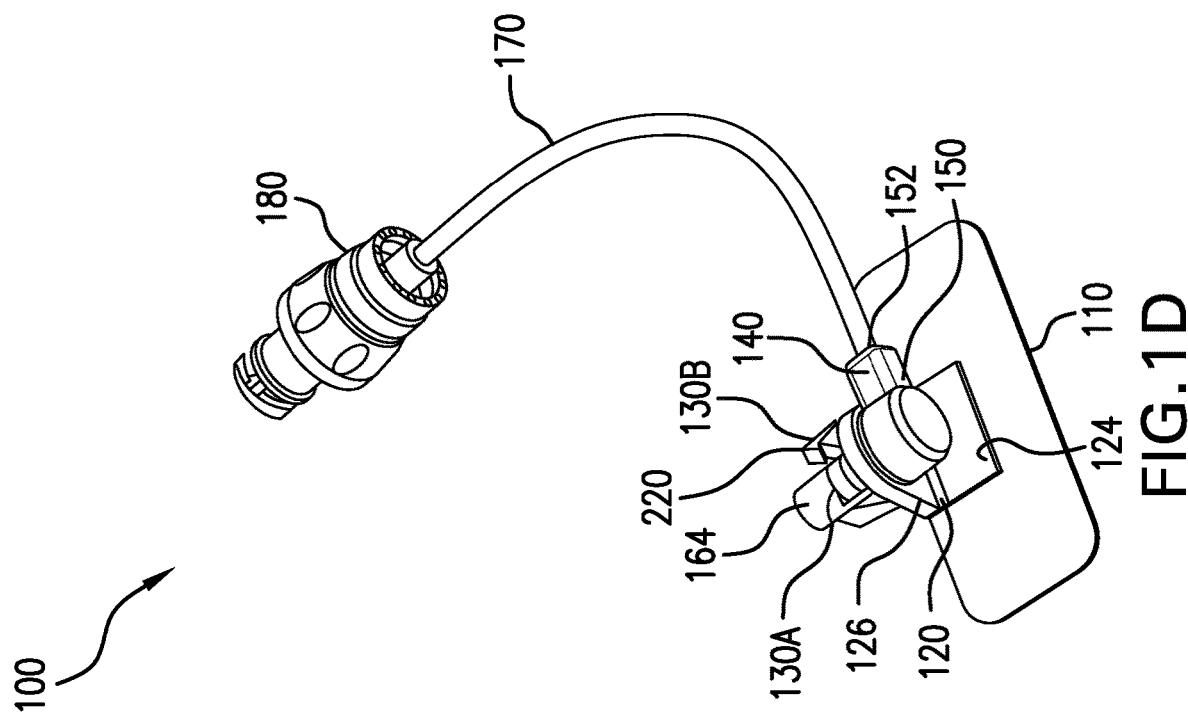
FIGS. 1C-1D schematically show various views of a vascular access site management system in a deployed state, in accordance with various embodiments of the present invention.
Figure 1C:
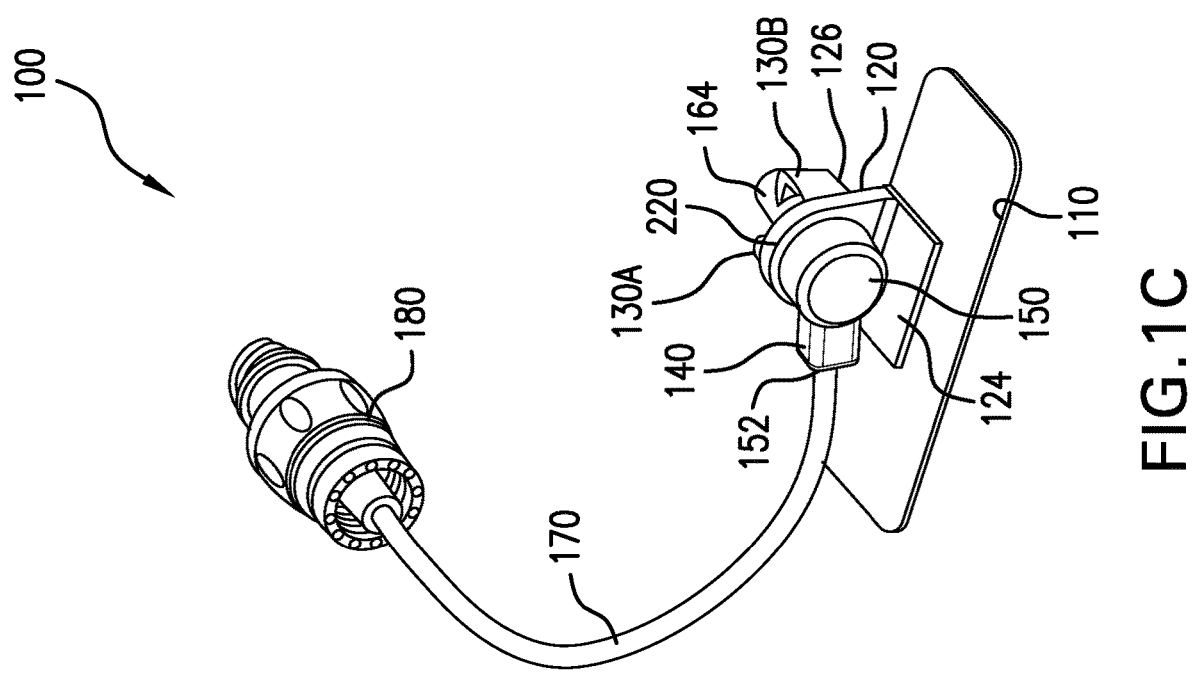

After the vascular access site management system 100 is secured (or re-secured) and there is adequate flow within the vein, the user rotate the flow housing 140, tube 170 and needle-free connector 180 to either the right or the left (e.g., from the upright position to the position shown in FIG. 1C or 1D). As the flow housing 140 is rotated, the camming action of the lug 162 camming surface 128 on the stabilization body 120 will cause the flow housing 140 (including the extension 160 and male luer connector portion 164) to move towards the catheter 210 and further secure the male luer connector portion 164 and the catheter 210. The user may then place a dressing over the connection site to maintain the cleanliness and sterility of the connection and connection site. It should be noted that, by allowing the user to choose either a left or right configuration, embodiments of the present invention allow the user to choose the best configuration for the given application based, for example, the user's preference, the amount of available space on either side of the catheter 210, the location of the catheter 210, etc.

Once the system 100 is fully secured to the patient, the catheter 210 cannot be inadvertently moved. Additionally, the medical implement (e.g., the syringe) may be connected and disconnected as needed without impacting the placement/location of the catheter 210. This, in turn, helps to prevent injury to the patient and ensures that adequate fluid flow through the device 100, catheter 210, and vein is maintained. Furthermore, because the device 100 includes a needle-free connector 180, the medical implement can be easily re-attached to the device 100 at a later time to introduce fluids into the patient and/or withdraw fluids from the patient.

It should be noted that, some embodiments of the present invention may have various features that help the user know/determine the distance from the system 100 to the tip of the catheter 210 so that the user can determine when the tip of the catheter 210 is located within the vein. For example, returning to FIGS. 1C and 1D, the stabilization body 120 and/or the flow housing 140 may have a dressing deployment surface 220 on which the dressing may be placed/secured and the edge of the dressing (not shown) may be aligned with a line or a marking on the stabilization body 120 or flow housing. Additionally, in such embodiments, the dressing may have a series of graduations or a grid pattern that corresponds to the length of the catheter 210. In this manner, when the user applies the dressing such that it is aligned with the line/marking, the user will be able to tell where in the vein the end of the catheter 210 is by the graduations on the dressing. To accommodate multiple types of catheters 210, the dressing may have multiple sets of graduations that correspond to different types and lengths of catheters 210.

Although the embodiments described above have a flow housing 140 with a main housing 150 and a housing extension 160 (with male luer portion 164) that all rotate relative to the stabilization body 120, other embodiments may have different rotational configurations. For example, as shown in FIGS. 5A-5E, in some embodiments, the vascular access site management system 400 may have stabilization body 410 with a male luer connector 420 extending from one side of the stabilization body 410 (e.g., the side facing the catheter 210) and a stabilization body extension 430 extending from the other side. Like the male luer portion 164 discussed above, the male luer connector 420 extending from the stabilization body 410 connects to the catheter 210 during use. Additionally, although not shown, the stabilization device can also include a locking mechanism, for example, locking arms like those described above to lock the catheter 210 to the device 400.

The stabilization body extension 430 may have one or more holes 440 (e.g., opposing side holes) (FIG. 5C) that extend through the wall of the stabilization body extension 430 and to the fluid path 450 (FIG. 5D) extending through the stabilization body 410 (e.g., through both the stabilization body extension 430 and the male luer connector 420). In some embodiments, the end of the stabilization body extension 430 may be a female luer lock 460. However, in other embodiments, the stabilization body extension 430 may have any other type of medical port or it may simply have a closed end or a capped port. In embodiments having a closed end or capped port, the stabilization body extension 430 may have a diaphragm or bellows that flexes/deforms with changes in the pressure, in a manner similar to that described above.

Figure 5A:
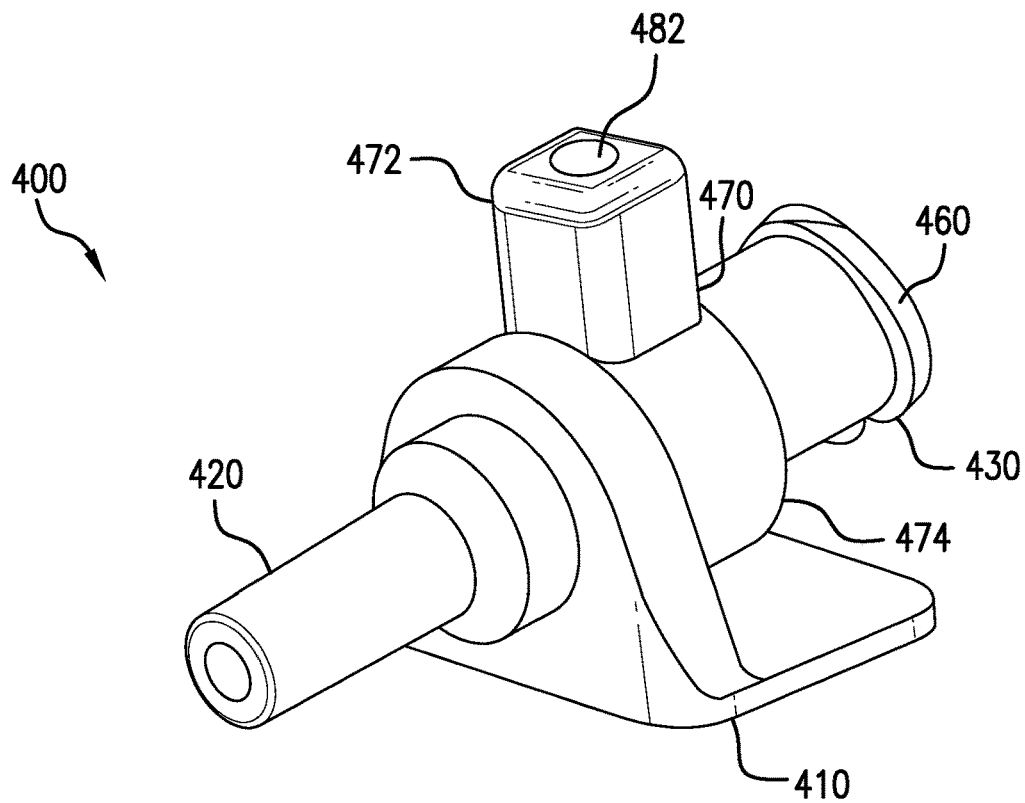
FIG. 5A schematically shows an alternative embodiment of a vascular access site management system in a closed mode, in accordance with some embodiments of the present invention.
Figure 5B:
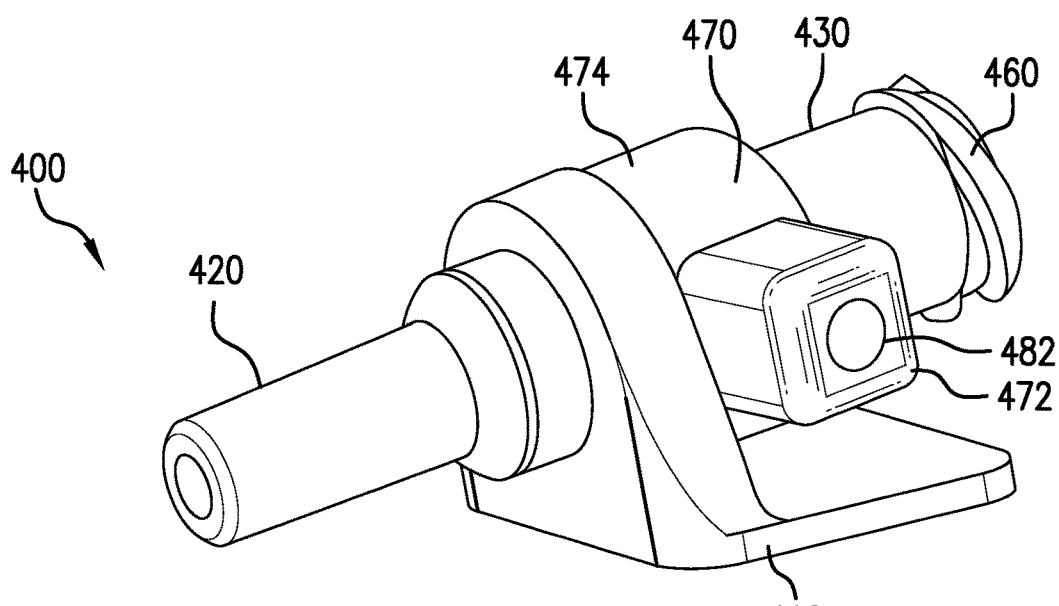
FIG. 5B schematically shows the alternative embodiment of a vascular access site management system shown in FIG. 5A in an open mode, in accordance with some embodiments of the present invention.
Figure 5C:
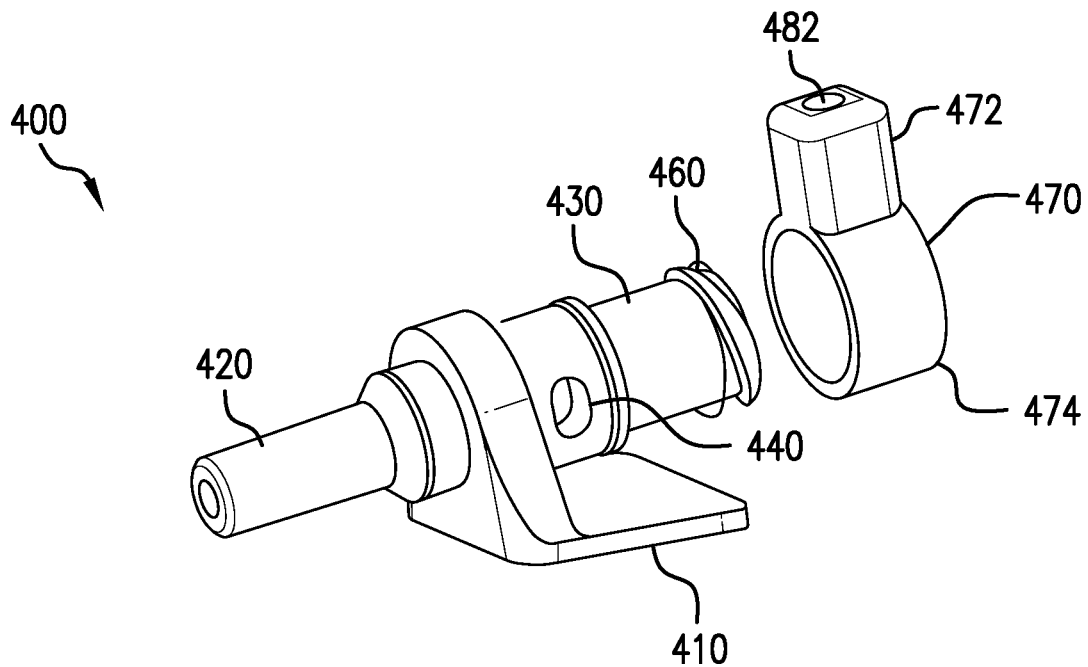
FIG. 5C schematically shows an exploded view of the alternative embodiment of a vascular access site management system shown in FIG. 5A, in accordance with some embodiments of the present invention.
Figure 5D:
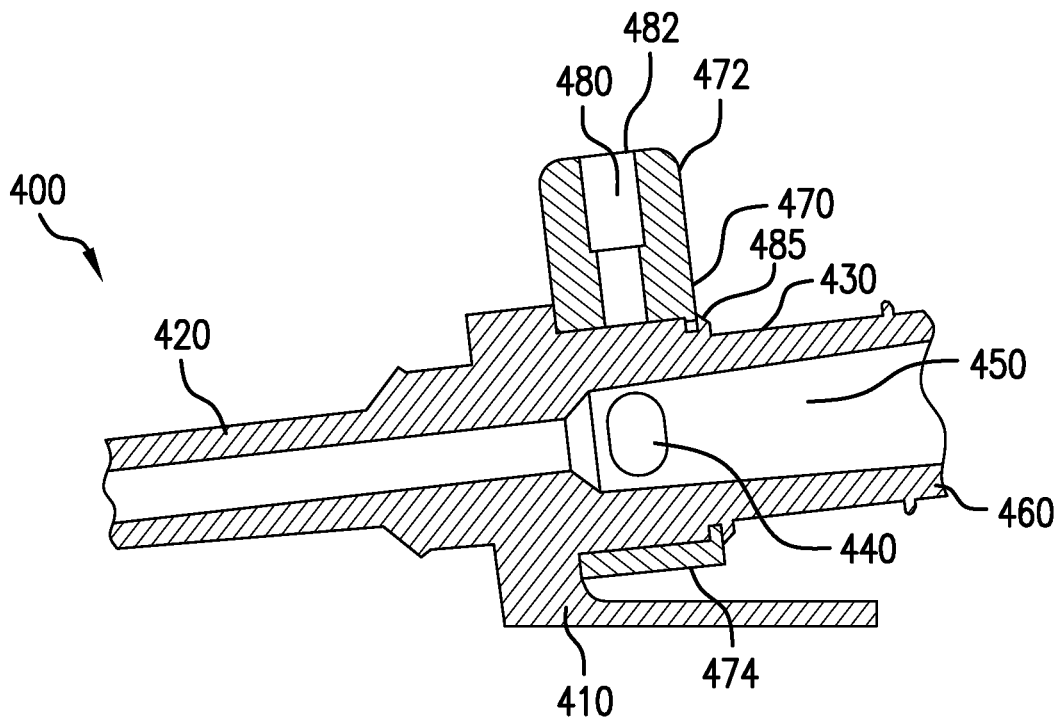
FIG. 5D schematically shows a cross-sectional view of the alternative embodiment of a vascular access site management system shown in FIG. 5A in the closed mode, in accordance with some embodiments of the present invention.
Figure 5E:
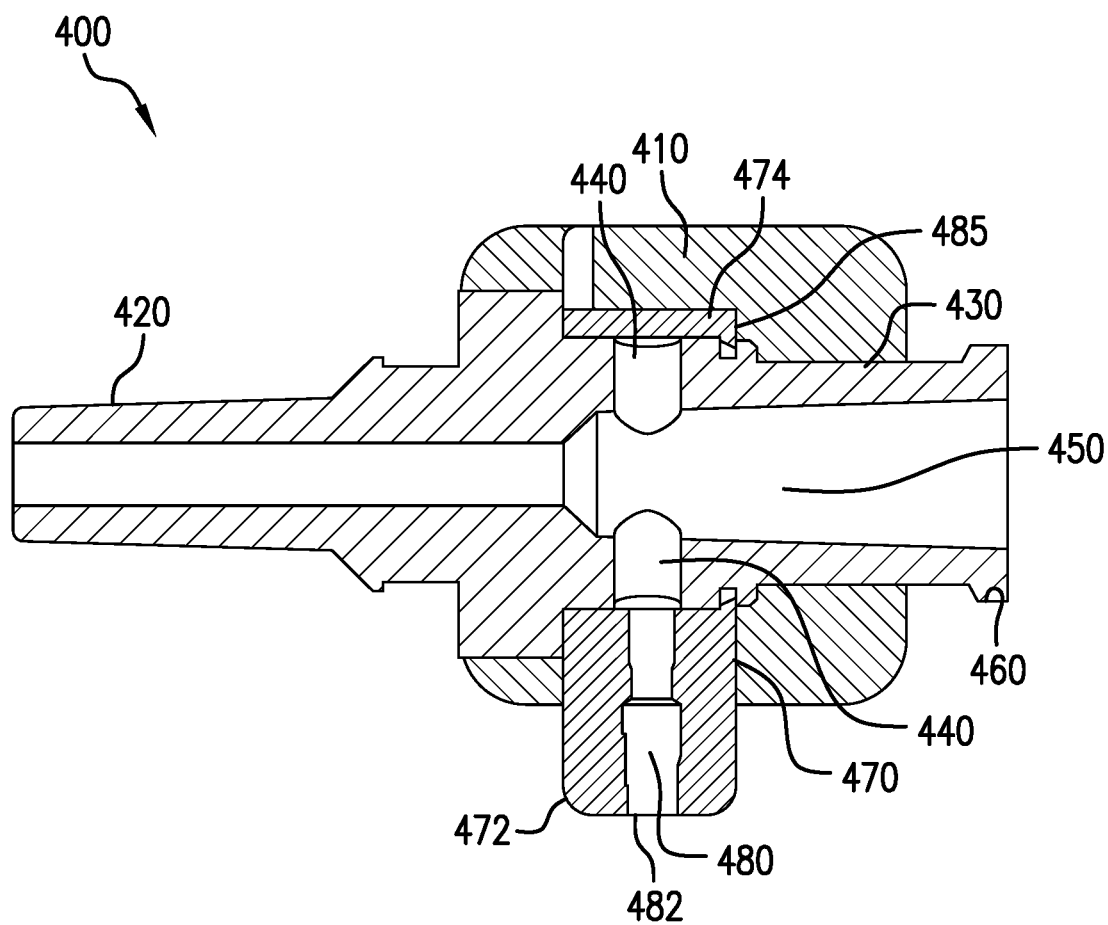
FIG. 5E schematically shows a cross-sectional view of the alternative embodiment of a vascular access site management system shown in FIG. 5A in the open mode, in accordance with some embodiments of the present invention.

Located on the stabilization body extension 430, the device 400 may have a flow sleeve 470 having a flow portion 472 with a fluid path 480 extending (FIG. 5D) through it, and a ring portion 474 that may snapped over (or otherwise secured) to the stabilization body extension 430. The flow sleeve 470 is rotatable with respect to the stabilization body extension 430 between a closed mode and one of two open modes. For example, in the closed mode, the flow portion may be in the vertical orientation (FIGS. 5A and 5D) and the fluid path 480 within the flow portion 472 may be fluidly disconnected from the holes 440 and the fluid path 450 extending through the stabilization body 410. During use, to transition the flow sleeve 470 to the one of the open modes (FIGS. 5B and 5D), the user may rotate the flow sleeve 470 to the left or right (depending on the user's preference and the configuration of the catheter 210) until it reaches the horizontal orientation (FIGS. 5B and 5E). To prevent leakage between the flow sleeve 470 and the stabilization body extension 430, the flow sleeve 470 (or the stabilization body extension 430) may include a seal 485.

When in the open mode, the fluid path 480 extending through the flow portion 472 is fluidly connected to the holes 440 and the fluid path 450 extending through the stabilization body 410. Although not shown, like the embodiments described above, the device 400 may also have a tube and a needle-free connector that are fluidly connected to the flow portion 472 and, in particular, the fluid path 480 (e.g., via port 482). Therefore, in a manner similar to that described above, when the flow sleeve 470 is in the open mode, the user may transfer fluid to and from the patient.

To ensure that the flow sleeve 470 does not inadvertently rotate back to the closed mode, some embodiments may have a locking mechanism that holds the flow sleeve 470 in the open position. For example, in some embodiments, the flow sleeve 470 may have a protrusion that enters a detent within the stabilization body extension 430. Additionally or alternatively, the stabilization body extension 430 may have protrusion that enters a detent in the flow sleeve 470 when in the open mode.

Additionally, although the embodiment described above and shown in FIGS. 5A-5E has opposing holes 440 that create discreet open modes, other embodiments may allow for fluid communication between the fluid path 480 in the flow sleeve 470 and the fluid path 450 extending through the stabilization body 410 in any orientation of the flow sleeve 470. For example, rather than opposing holes 440, some embodiments may have a channel within stabilization body extension 430 that connects the two holes 440. Therefore, the fluid path 480 in the flow sleeve 470 is fluidly connected to the fluid path 450 in the stabilization body 410 when the flow sleeve 470 is in the vertical orientation, horizontal orientation or anywhere in between.

It should be noted that in the embodiment shown in FIGS. 5A-5E, the catheter and the male luer connector 420 are rotationally decoupled from the rotation of the flow sleeve 470. Therefore, any rotation of the flow sleeve 470 does not rotate the male luer connector 420 and/or the catheter.

FIGS. 6A-6E show an additional embodiment of a vascular access site management system 500. Like the management systems 100/400 described above, the management system 500 shown in FIGS. 6A-6E may have a needle-free connector 180 that is fluidly connected to a flow housing 540 via a tube 170. The needle-free connector 180 can be any number of needle-free connectors and/or medical valves. For example, in some embodiments, the needle-free connector may be a swabbable luer activated such that those described in U.S. Pat. Nos. 6,755,391, 7,014,169, 6,039,302, 7,100,890, and 7,789,864, the disclosures of which are incorporated herein by reference.

The management system 500 also includes a rotatable stabilization pad 520 that is rotatable about the flow housing 540 that is secured/retained within the stabilization pad 520. The stabilization pad 520 may have base 522 that may be placed on the patient during use and may support the flow housing 540. To retain the flow housing 540, the stabilization pad 520 may also include a proximally extending portion 524 that extends upward from the base 522, and an opening 526 extending through the proximally extending portion 524. The flow housing 540 may be pushed through the opening 526 such that the portion of the proximally extending portion 524 surrounding the opening 526 snaps into a recess 541 within the flow housing 540. As noted above, the stabilization pad 520 should be able to rotate about the flow housing 540. Therefore, the opening 526 should be sized such that the connection between the pad 520 and flow housing 540 does not interfere with the rotation. In some embodiments, the stabilization pad 520 may be elastomeric.

At one end, the flow housing 540 may include a male luer lock connector 550 that connects to the catheter 210 within the patient. To help the user during connection of the catheter 210, the stabilization pad 520 may include a retention feature 528 (FIG. 6E) that holds the collar/ring 552 of the male luer lock connector 550 back during initial connection with the catheter 210. For example, the retention feature 528 may be a ridge or protrusion that contacts the ring 552 and essentially interferes with the forward and backward movement of the ring 552. Once the initial connection has been made (e.g., the male luer portion has been inserted into the female luer on the catheter 210), the user may rotate the ring 552 to release it from the retention feature 528 and allow the user to screw the ring 552 onto the catheter 210.

Figure 6A:
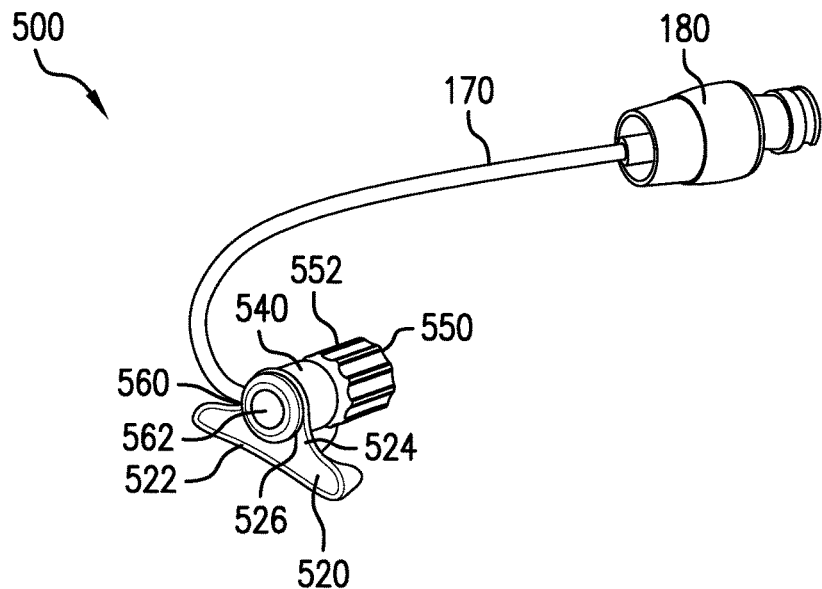
FIG. 6A schematically shows a further alternative embodiment of a vascular access site management system, in accordance with some embodiments of the present invention.
Figure 6B:
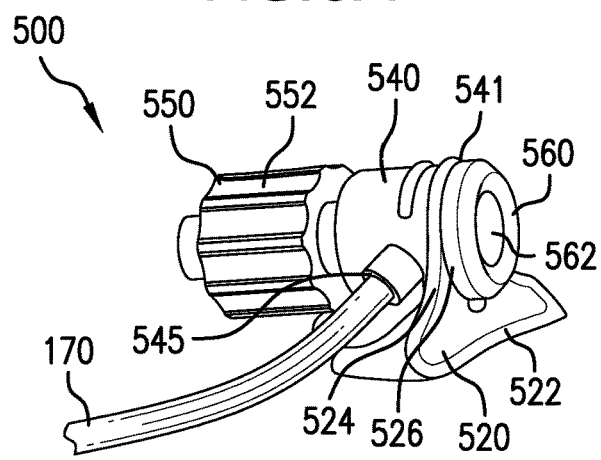
FIG. 6B schematically shows the alternative embodiment of a vascular access site management system shown in FIG. 6A in a first deployed position, in accordance with some embodiments of the present invention.
Figure 6C:
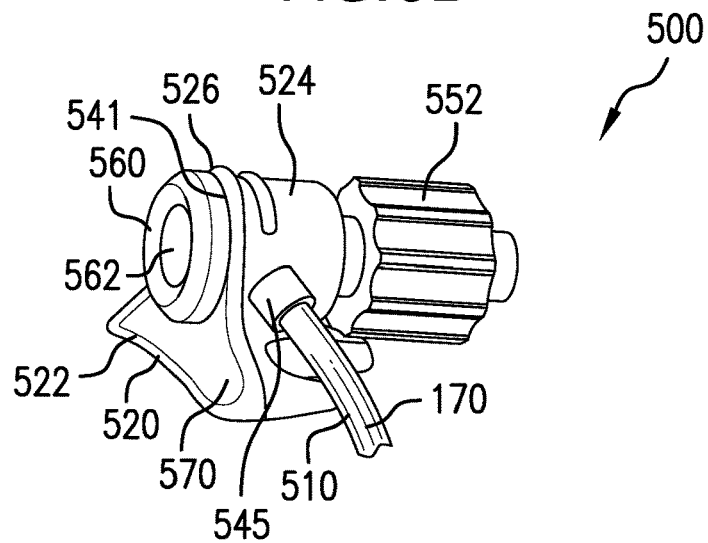
FIG. 6C schematically shows the alternative embodiment of a vascular access site management system shown in FIG. 6A in a second deployed position, in accordance with some embodiments of the present invention.
Figure 6D:
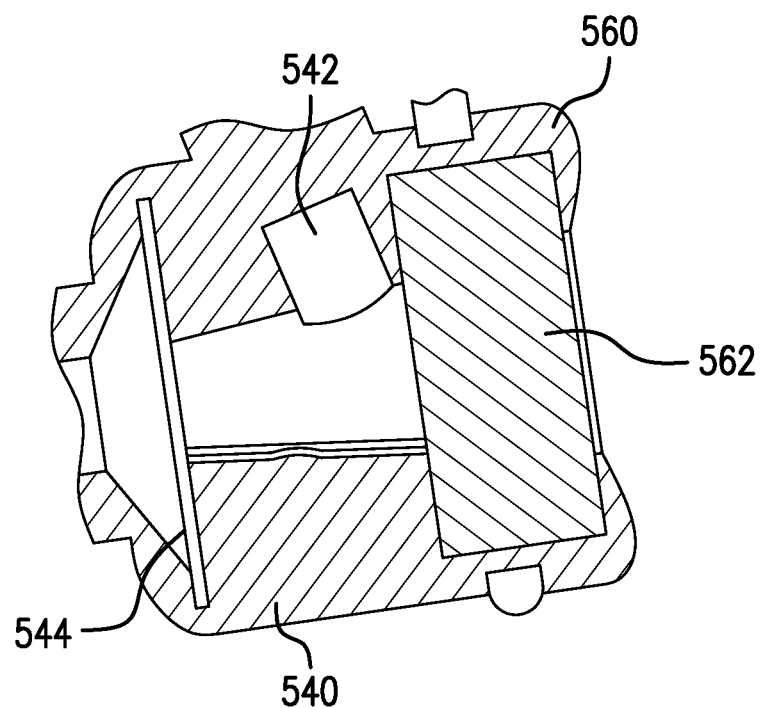
FIG. 6D schematically shows a cross-sectional view of the flow housing of the alternative embodiment of a vascular access site management system shown in FIG. 6A, in accordance with some embodiments of the present invention.
Figure 6E:
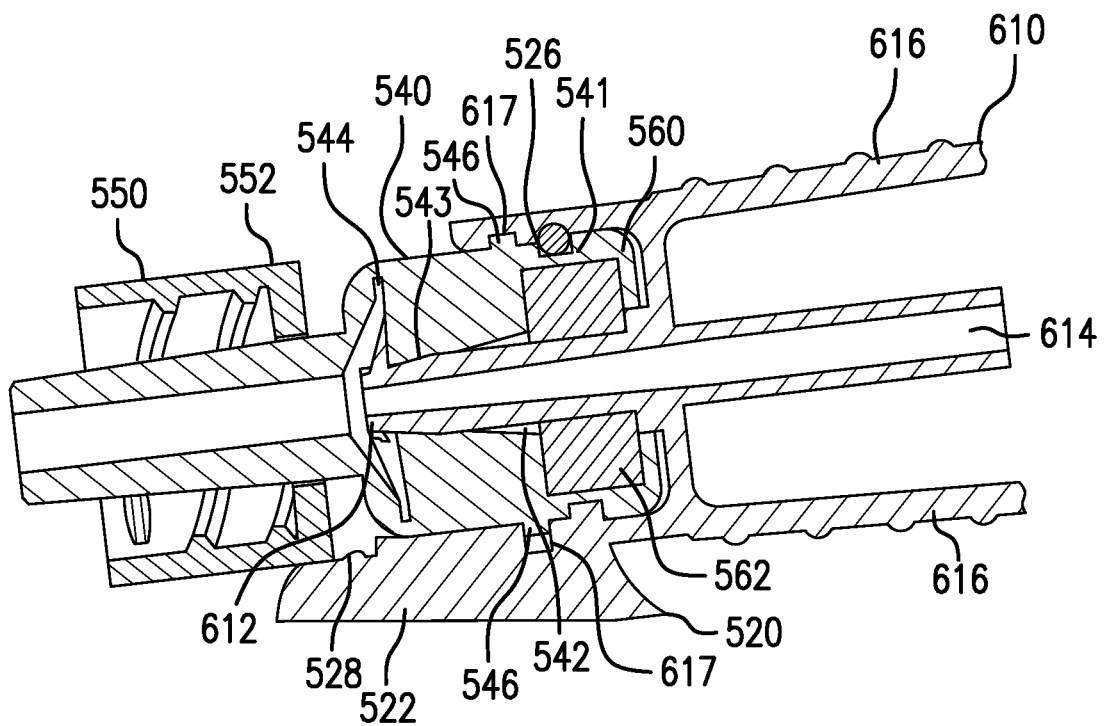
FIG. 6E schematically shows a cross-sectional view of the alternative embodiment of a vascular access site management system shown in FIG. 6A, in accordance with some embodiments of the present invention.
Figure 7A:
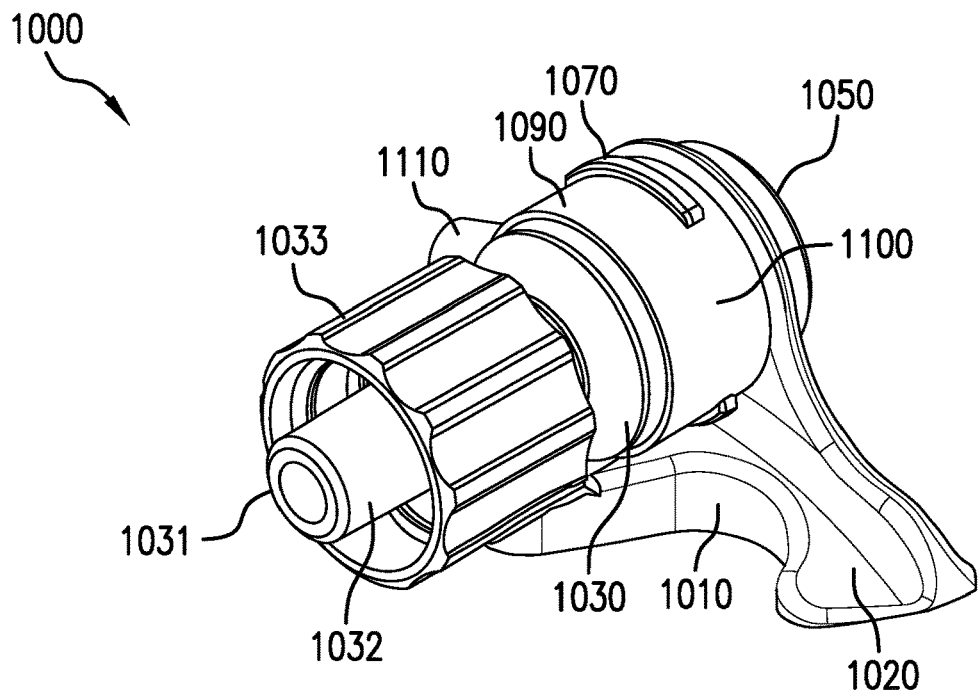
FIGS. 7A-7D schematically show an additional embodiment of a vascular access site management system in a first position, in accordance with further embodiments of the present invention.
Figure 7B:
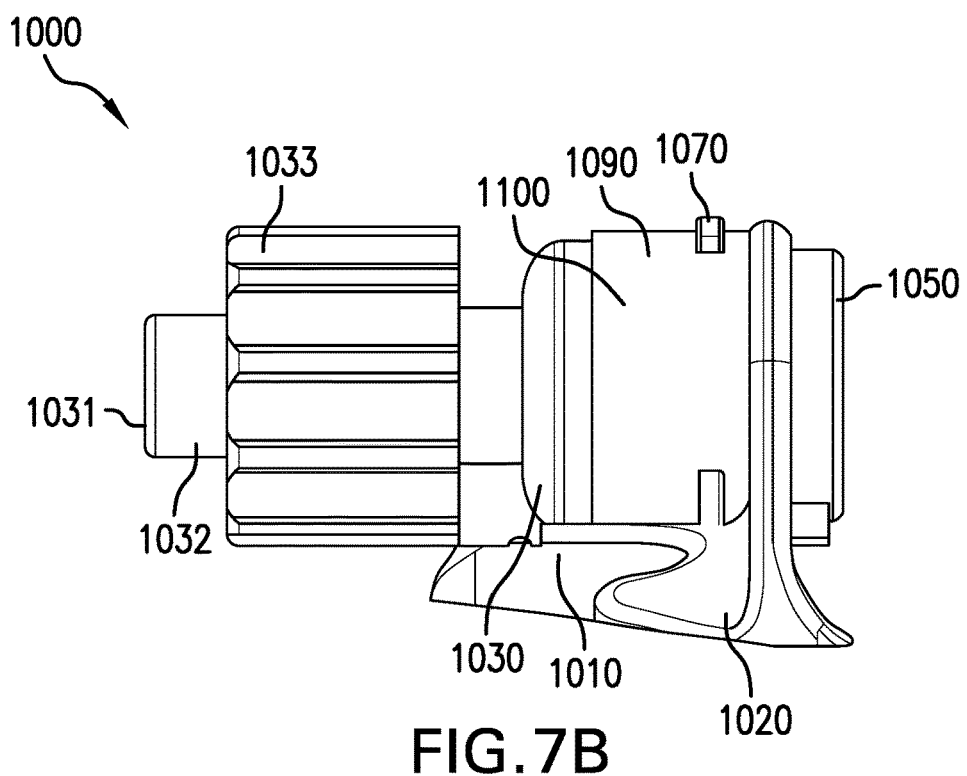
Figure 7C:
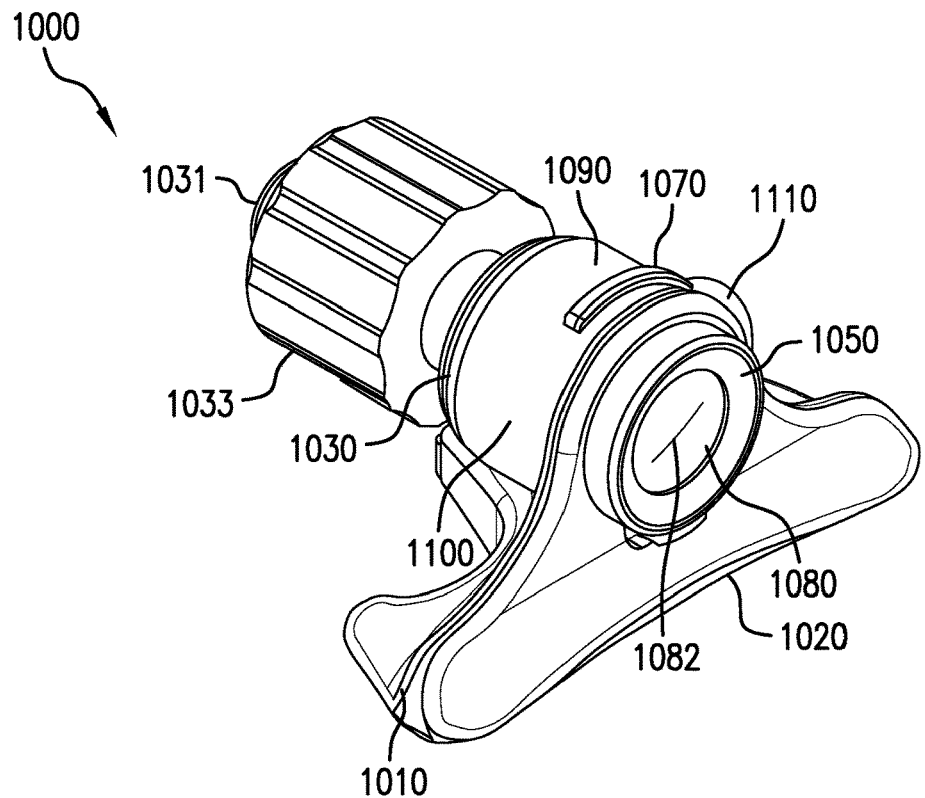
Figure 7D:
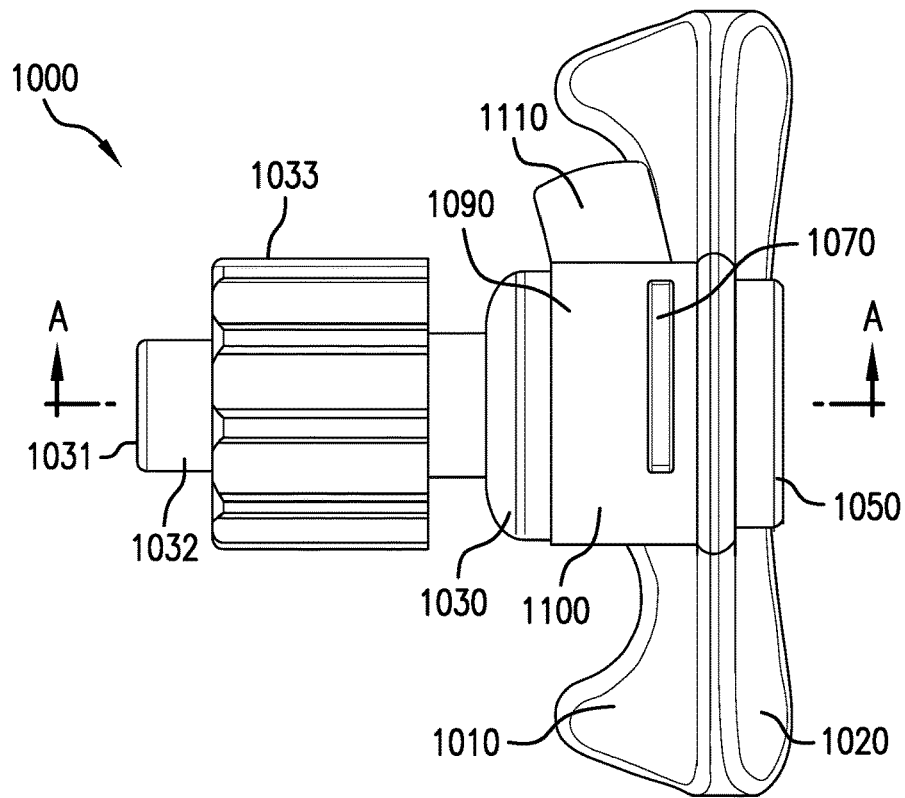
Figure 8A:
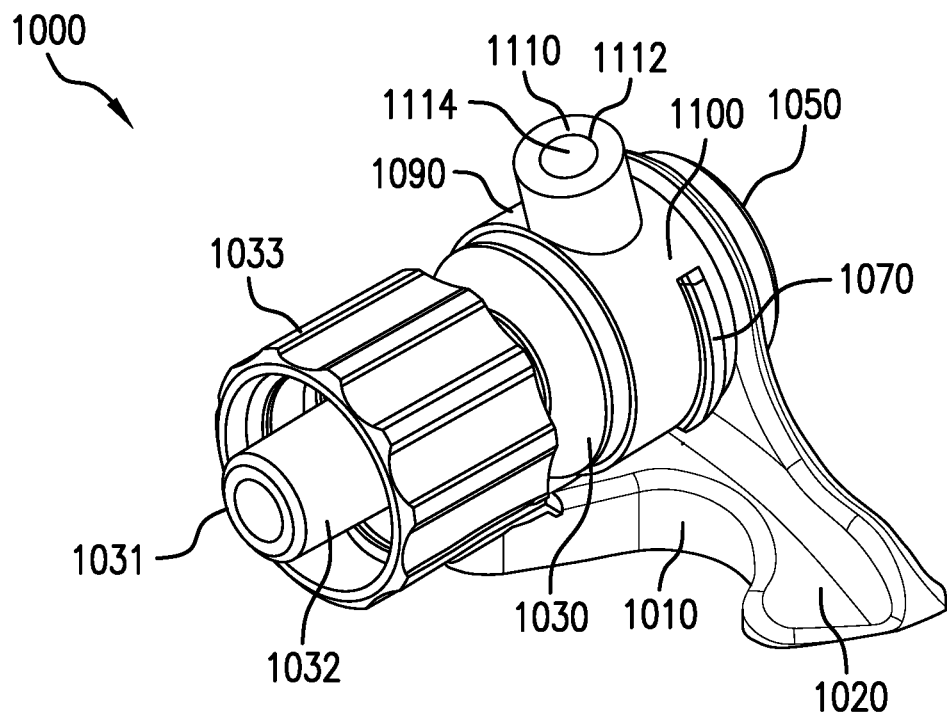
FIGS. 8A-8C schematically show the vascular access site management system of FIGS. 7A-7D in a second position, in accordance with further embodiments of the present invention.
Figure 8B:
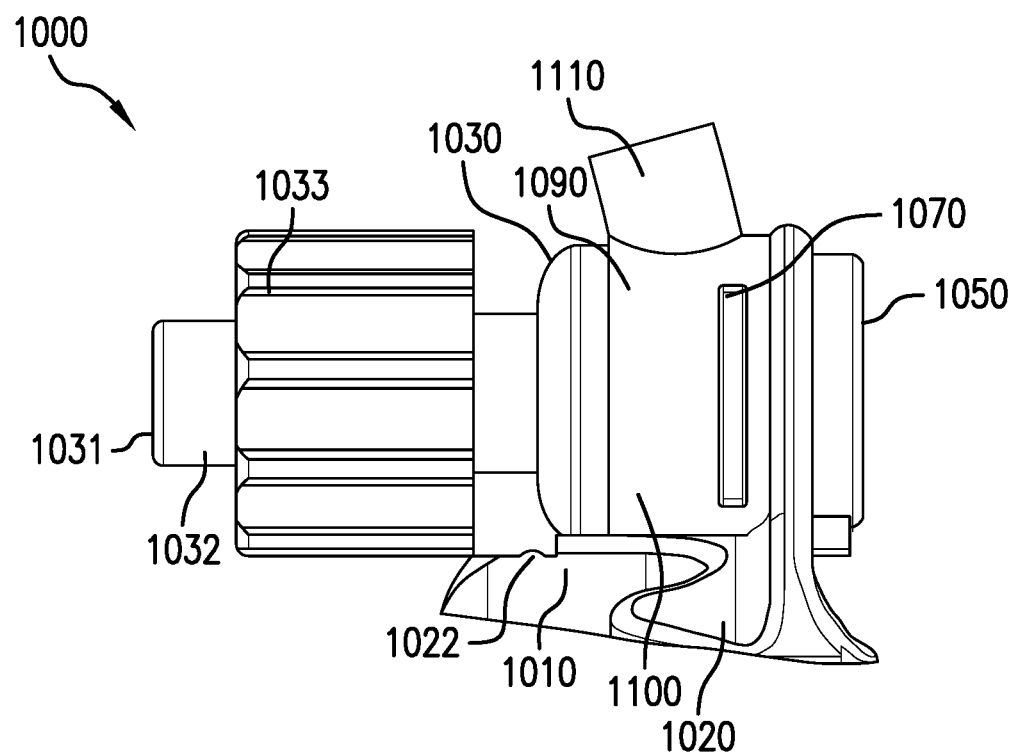
Figure 8C:
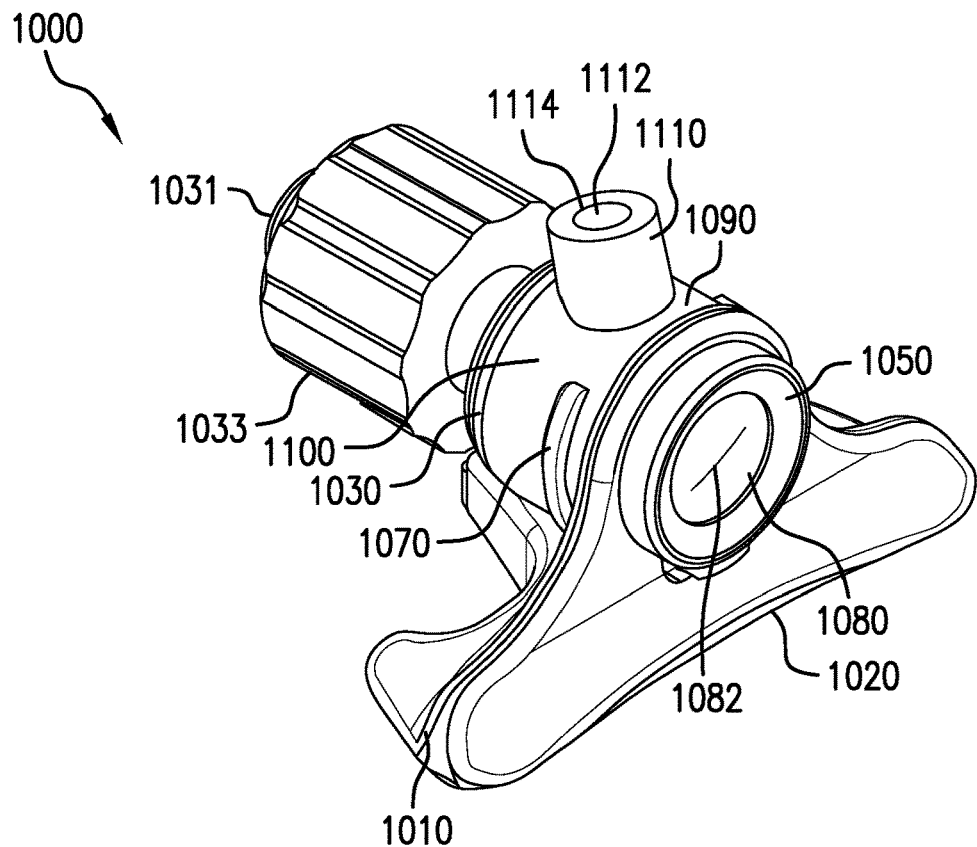
Figure 9A:
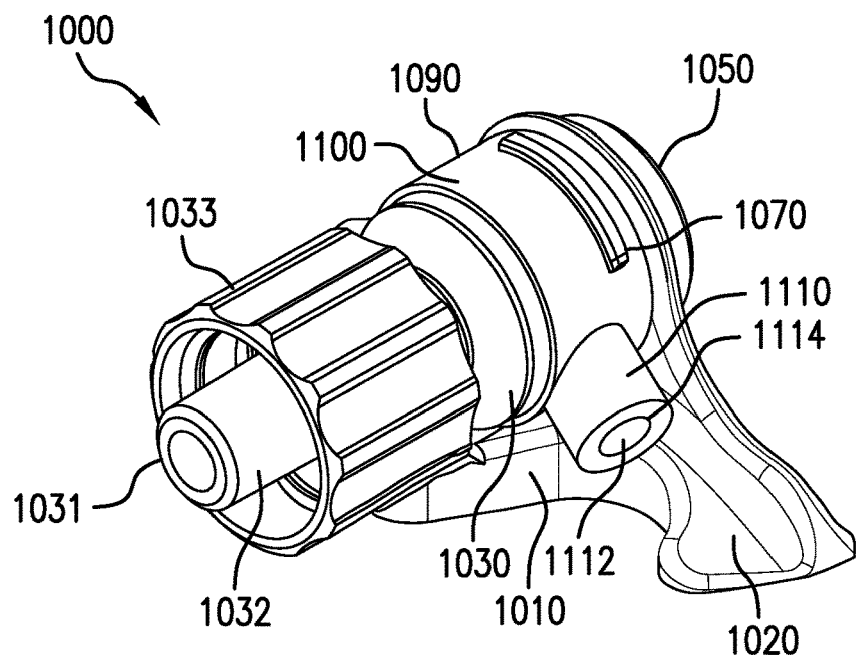
FIGS. 9A-9C schematically show the vascular access site management system of FIGS. 7A-7D in a third position, in accordance with further embodiments of the present invention.
Figure 9B:
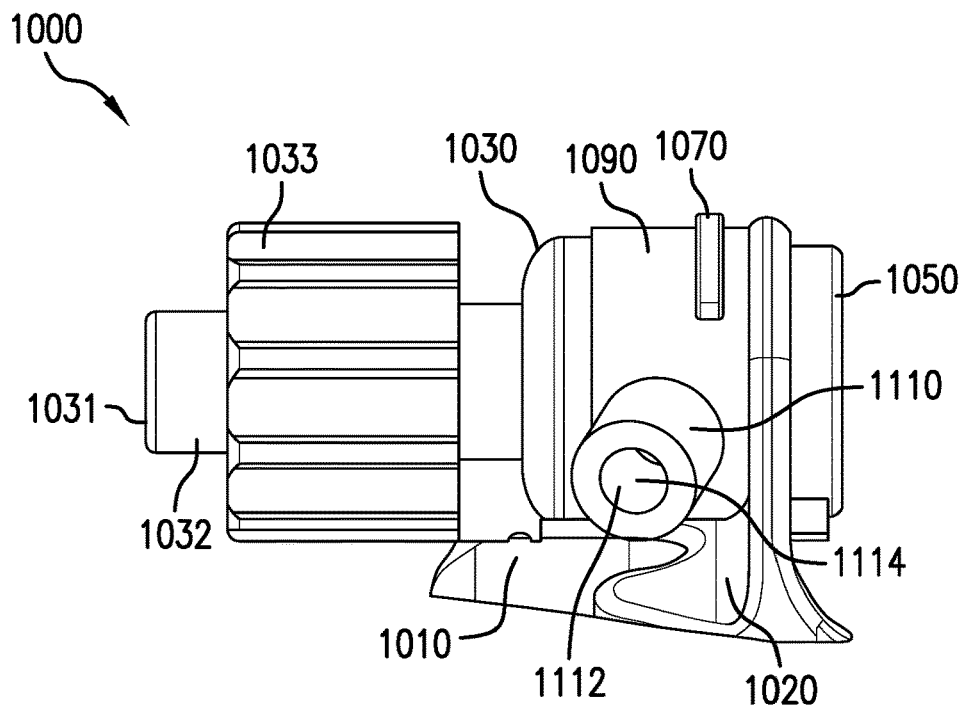
Figure 9C:
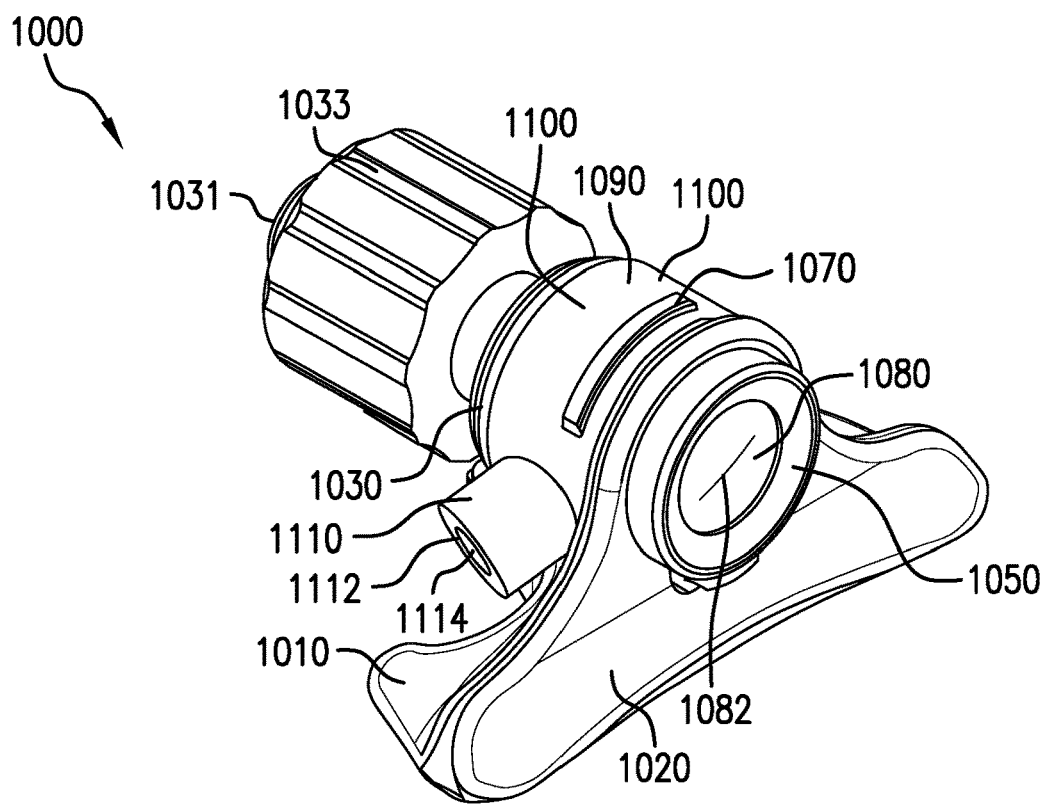

Like the flow housings described above, the flow housing 540 shown in FIGS. 6A-6E has a flow path 542 extending through it to allow fluid to be transferred to and/or from the patient during use. The tube 170 may be fluidly connected to the flow path 542 via port 543. To control fluid flow through the management system 500 and the flow housing 540, the interior of the flow housing 540 may include a valve mechanism 544 within the internal fluid path 542 (FIGS. 6D and 6E). For example, the flow housing 540 may include a two-way pressure activated valve 544 (PAV) like that described above. The valve mechanism 544 prevents fluid flow through the flow housing 540 (e.g., through the internal fluid path 154) until it is exposed to a large enough pressure to open the slit through the diaphragm (e.g., a cracking pressure).

In some applications, it may be necessary to introduce a medical article into the catheter 210. For example, the user may need to access to a peripheral vein through the indwelling catheter 210 to introduce sensors for detecting a patient condition, introduce delivery lines for certain medicaments/agents, and/or introduce tubing for direct blood withdrawal. To that end, the flow housing 540 may have a split septum port 560 for receiving a medical implement 610 (e.g., a blunt cannula or other medical device or connector). As the name suggests, the split septum port 560 includes a septum 562 that obstructs the port 560 and normally seals off the interior of the flow housing 540 (e.g., it seals off the flow path 542 from the environment/exterior of the flow housing 540. To allow for connection of the medical implement 610, the septum 562 may include an aperture or a slit extending through it. To that end, during connection of the medical implement 610 to the flow housing 540, the end 612 (e.g., the distal tip) of the medical implement 610 deforms the septum 562, thus opening the aperture/slit to allow the medical implement 610 to extend through the septum 562.

As shown in FIG. 6E, the medical implement 610 may have a channel 614 extending through it to allow the medical article (not shown) to be introduced into the catheter 210 and/or vein through the system 500. However, it should be noted that any obstructions, bends, turns, etc. within the path between the channel 614 and the catheter 210/vein may make it difficult to introduce the medical article. For example, if the valve mechanism 544 is closed, it will obstruct the pathway and, potentially prevent the medical article from being introduced. In view of the above, some embodiments may have various features that help to provide a clear path for the introduction of the medical article by positioning the medical implement 610 such that the end 612 of the medical implement 610 is near the valve mechanism 544 and, in some cases, partially opens or fully opens the valve mechanism.

For example, the flow housing 540 can include one or more protrusions 546 that extend out from the flow housing 540 and enter a recess 617 within the arms 616 of the medical implement 610 when it is connected to the flow housing 540. The location of both the protrusions 546 and the recesses 617 may be such that the end 612 of the medical implement 610 is located at the valve mechanism 544 or, as shown in FIG. 6E opens the valve mechanism 544. Additionally or alternatively, to help appropriately position the medical implement 610, the flow path 542 may include a contact surface 543 that contacts the outer surface of the medical implement 610 and acts as a stop for the medical implement 610 (e.g., the outer diameter of the medical implement 610 may contact the inner diameter of the flow path 542 so that the medical implement 610 stops in the desired position). In addition to acting as a stop for the medical implement 610, the contact surface 543 may also keep the tip/end 612 of the medical implement 610 (and therefore the channel 614) concentric with the opening through the valve mechanism 544 and the male luer connector 550.

In other embodiments, the medical implement 610 and/or the flow path 542 may also have a guide ribs extending along at least a portion of its length (e.g., along the outer diameter of the medical implement 610 and/or the inner diameter of the flow housing 540). The guide ribs guide the medical implement 610 into the flow housing 540 and keep it concentric within the flow path 542 and, perhaps help position the medical implement 610 longitudinally within the flow housing 540. The ribs may be deformable or crushable.

Although the vascular access site management system shown in FIGS. 6A-6E includes a stabilization pad 520 that rotates with respect to the flow housing 540, other embodiments may have different configurations. For example, as shown in FIGS. 7-11, some embodiments may include a stabilization body 1010 and a flow housing 1090 that is rotatable about the stabilization body 1010 (and not just a stabilization pad 520). It should be noted that, like the management systems described above, the management system 1000 shown in FIGS. 7-11 may have a needle-free connector that is fluidly connected to the flow housing 1090 via a tube. The needle-free connector can be any number of needle-free connectors and/or medical valves.

The stabilization body 1010 has a base 1020 and an upper portion 1030 extending from the base 1020. During use, the base 1020 may be placed on the patient to support and stabilize the device 1000 on the patient. At one end, the upper portion 1030 may include a male luer lock connector 1032 that connects to the catheter 210 within the patient. Like the other embodiments described herein, the base 1020 may be oriented at an angle (e.g., between 5 and 10 degrees) with respect to a longitudinal axis of the outlet 1031 (e.g., the outlet of the male luer lock connector). To help the user during connection of the catheter 210, the base 1020 may include a retention feature 1022 (FIGS. 10A and 10B) that holds the collar/ring 1033 of the male luer lock connector 1032 back during initial connection with the catheter 210. For example, like the retention feature described above, the retention feature 1022 may be a ridge or protrusion that contacts the ring 1033 and essentially interferes with the forward and backward movement of the ring 1033.

Figure 10A:
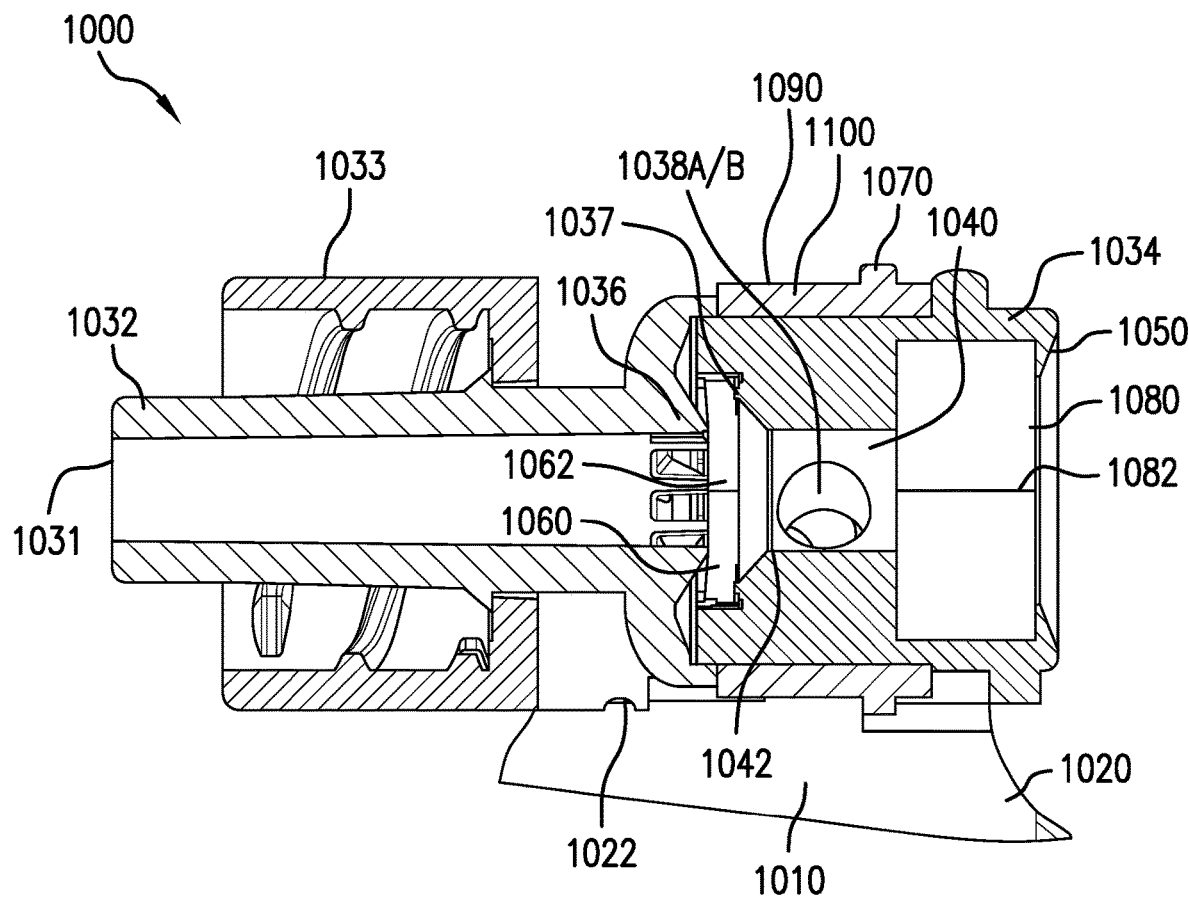
FIG. 10A schematically shows a cross-sectional view of the vascular access site management system shown in FIGS. 7A-7D with a valve mechanism in the closed mode, in accordance with additional embodiments of the present inventions.
Figure 10B:
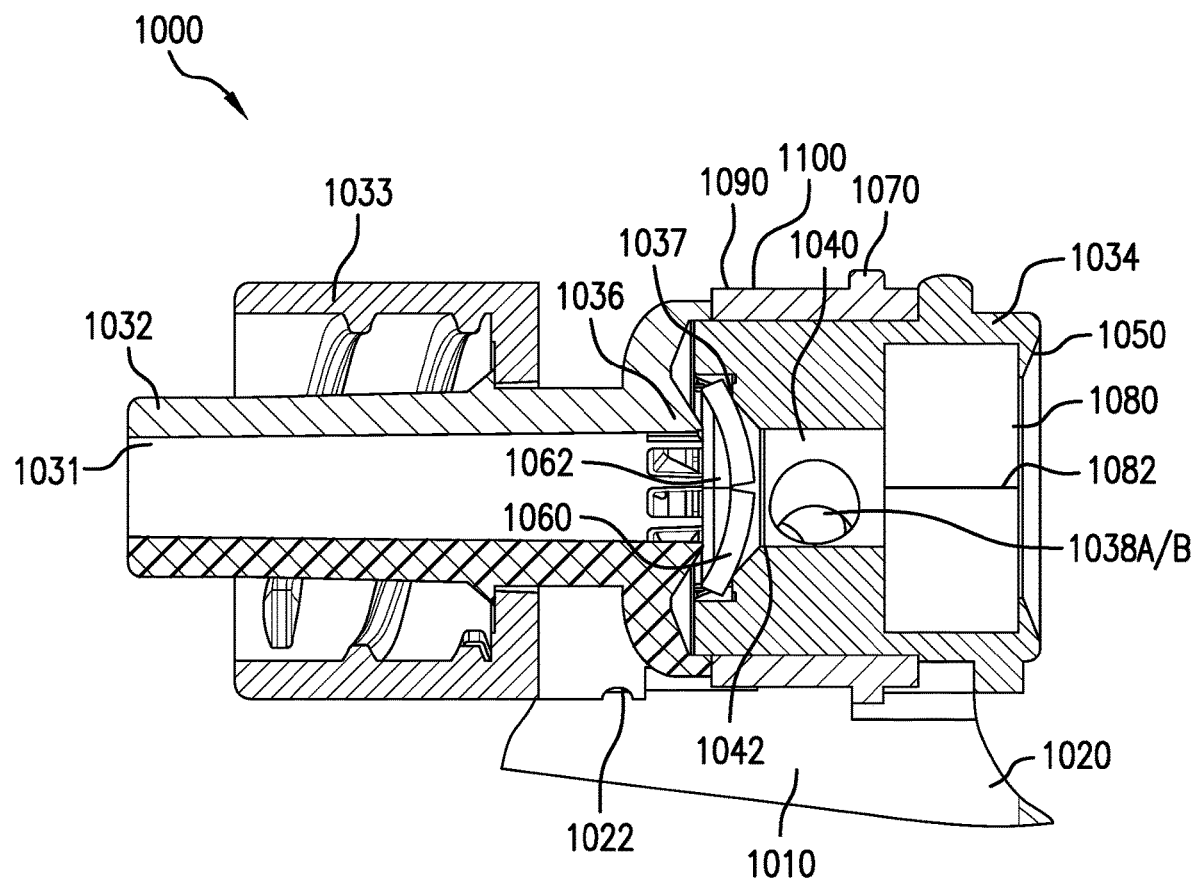
FIG. 10B schematically shows a cross-sectional view of the vascular access site management system shown in FIGS. 7A-7D with a valve mechanism in an open mode for retrograde flow, in accordance with additional embodiments of the present inventions.

As shown in FIG. 10A, the upper portion 1030 has a flow path 1040 extending through it (e.g., to outlet 1031) to allow fluid to be transferred to and/or from the patient during use. To control fluid flow through the management system 1000 and the upper portion 1030, the interior of the upper portion 1030 may include a valve mechanism 1060 (e.g., a two-way pressure activated valve (PAV) with a slit 1062) within the internal flow path 1040 (FIGS. 10A and 10B). The valve mechanism may deform in the presence of a forward pressure (e.g., toward the outlet 1031) to allow fluid to flow around the valve mechanism 1060 and through the upper portion 1030. Additionally, in the presence of a retrograde pressure (e.g., from the outlet 1031), the slit 1062 may open to allow fluid flow through the upper portion 1030 from the outlet 1031 toward an inlet 1114 in the flow housing 1090 (described in greater detail below). It should be noted that, to avoid low pressure flow (e.g. blood reflux) through the valve mechanism 1060, the pressure required to open the slit in the retrograde direction should be greater than the venous pressure of the patient.

To help support the valve mechanism 1060 within the flow path 1040, the upper portion 1030 of the stabilization body 1010 may include a number of support arms 1036. In the presence of the forward pressure and as the valve mechanism 1060 deforms, the valve mechanism 1060 may deform away from a seating/sealing surface 1037 within the upper portion 1030 and over the support arms 1036 to allow the fluid flow toward the outlet 1031, around the valve mechanism 1060 and between the spaces between the support arms 1036. Additionally, the support arms 1036 may be located radially inward from the seating/sealing surface 1037 to promote deformation (e.g. bending) of the valve mechanism 1060 around the support arms 1036 in the presence of the forward pressure. It should be noted that, although the figures show eight support arms 1036, other embodiments may have more or less than eight support arms 1036. For example, some embodiments may have seven or less support arms 1036 and other embodiments may have nine or more support arms 1036. Furthermore, the number of support arms 1036, their width(s) and contact area(s), and the amount of open space between each support arm 1036 will at least partially influence the degree that the valve mechanism 1060 bends around the support arms 1060 and the size of the opening between the seating/sealing surface 1037 and valve mechanism 1060 (e.g. size of flow path).

As shown in FIGS. 9A-9C and 10A-10B, the flow housing 1090 has a sleeve portion 1100 and a pathway portion 1110 extending from the sleeve portion 1100. The sleeve portion 1100 is located on/around the upper portion 1030 of the stabilization body 1010 such that the flow housing 1090 can rotate with respect to the stabilization body 1010, for example, between a closed mode (e.g., the position shown in FIGS. 8A-8C) and at least one open mode (e.g., the positions shown in FIGS. 7A-7C and 9A-9C). The pathway portion 1110 has a fluid path 1112 that extends through it and that is fluidly connected to the flow path 1040 within the upper portion 1030 when in the open mode(s). The inlet 1114 of the fluid path 1112 may be connected to the tube leading to the needle free connector (discussed above). Alternatively, a medical implement (e.g., for fluid transfer in/out of the patient) may be connected directly to the inlet 1114. It should be noted that the catheter 210 and the stabilization body 1010 are rotationally decoupled from the rotation of the flow housing 1090. Therefore, any rotation of the flow housing 1090 does not rotate the stabilization body 1010 and/or the catheter.

To create fluid communication between the flow path 1040 in the upper portion 1030 of the stabilization body 1010 and the fluid path 1112 in pathway portion 1110, the upper portion 1030 may have one or more holes 1038A/B extending through the wall of the upper portion 1030. For example, in the closed mode, the flow housing 1090 may be in the vertical orientation (FIGS. 8A-8C) and the fluid path 1112 within the pathway portion 1110 may be fluidly disconnected from the holes 1038A/B and the flow path 1040 in the upper portion 1030. To transition the flow housing 1090 to one of the open modes (FIGS. 7A-7C and 9A-9C), the user may rotate the flow housing 1090 to the left or right (depending on the user's preference and the location of the catheter 210 upon the patient). When in one of the open modes, the fluid path 1112 extending through the flow housing 1090 is fluidly connected to one of the holes 1038A/B and the flow path 1040 in the upper portion 1030.

As discussed above, in some applications, it may be necessary to introduce a medical article into the catheter 210. To that end, the upper portion 1030 may have a port 1050 with split septum 1080 for receiving a medical implement 610. The split septum 1080 obstructs the port 1050 and normally seals off the interior of the upper portion 1030 (e.g., it seals off the flow path 1040 from the environment/exterior of the upper portion 1030). As the name suggests, the septum 1080 may include an aperture or a slit 1082 through which the end/distal tip 612 of the medical implement may pass. For example, while engaging the medical implement 610 with the upper portion 1030, the end/distal tip 612 will deform the septum 1080, and opens the aperture/slit 1082 to allow the distal tip 612 to enter the interior of the device 1000 (e.g., the flow path 1040).

It should be noted that, although the figures show a split septum-style sealing mechanism 1080, other embodiments may have alternative valving mechanisms for sealing off the flow path 1040 from the environment/exterior of the upper portion 1030 and allow the distal tip 612 to enter the interior of the device 1000. For example, some embodiments may include a valve structure such as that described in U.S. Pat. No. 9,079,005 (incorporated herein by reference in its entirety). In such embodiments, the sealing mechanism may have a proximal portion located within the port, a wall that extends distally from the proximal portion within the interior of the device 1000 (e.g., within the interior of the upper portion) and an open distal end. The wall may form an interior within the sealing mechanism. To support the sealing mechanism within the device 1000, the device 1000 may include structures against which the end of the wall may contact.

As also discussed above, obstructions, bends, turns, etc. within the path between the channel 614 in the medical implement 610 and the catheter 210/vein may make it difficult to introduce the medical article. To that end, like the flow housing 540 mentioned above, the upper portion 1030 can include one or more engagement features (e.g., protrusions 1070) that extend out from the device 1000 (e.g., from the flow housing 1090) and enter an engagement feature (e.g., a recess 617) within the arms 616 of the medical implement 610 when it is connected to the device 1000. The location of both the protrusion(s) 1070 and the recess(es) 617 may be such that the distal tip 612 of the medical implement 610 is located at a predetermined longitudinal position within the flow path 1040 and interacts with the valve mechanism 1060. For example, the distal tip 612 may merely contact the valve mechanism 1060 to make it easier for the medical article to open the slit 1062 or, as shown in FIG. 11, the distal tip 612 of the medical implement 610 may partially or fully open the slit 1062 within the valve mechanism 1060.

Figure 11:
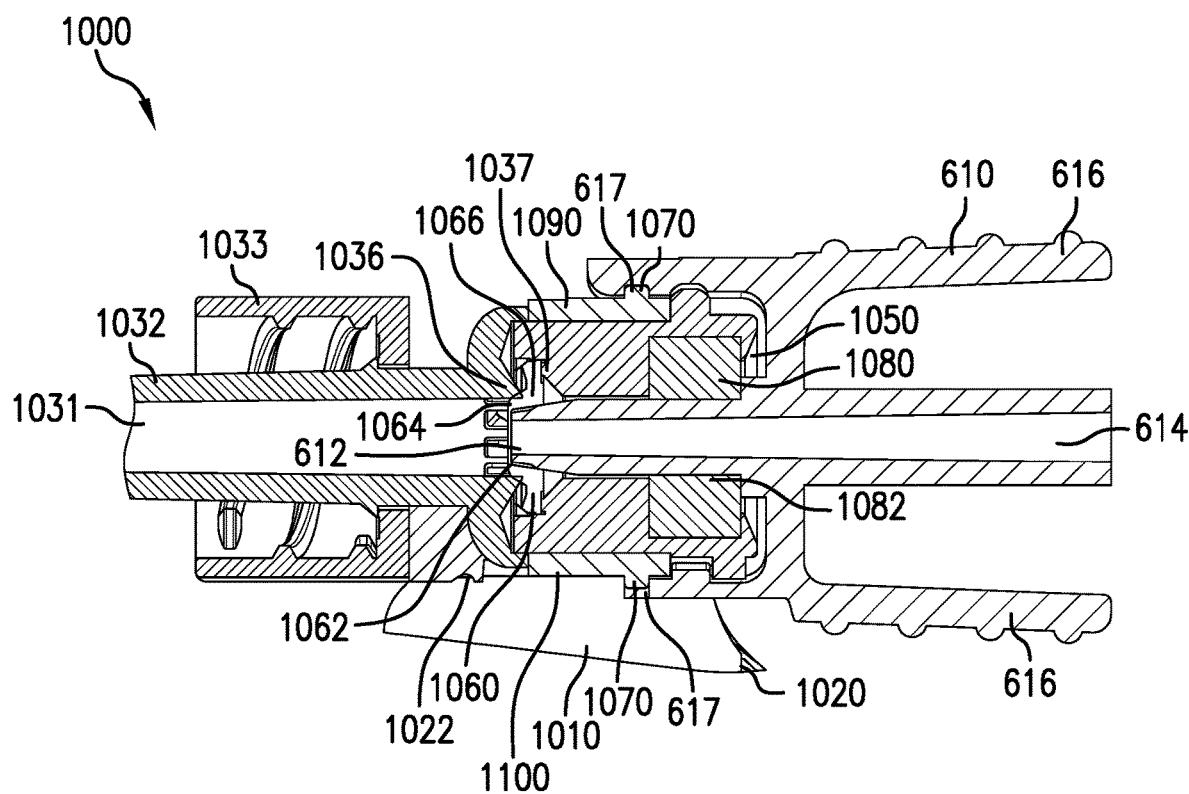
FIG. 11 schematically shows a cross-sectional view of the vascular access site management system shown in FIGS. 7A-7D with a medical implement connected to the vascular access site management system, in accordance with additional embodiments of the present inventions.
Figure 12A:
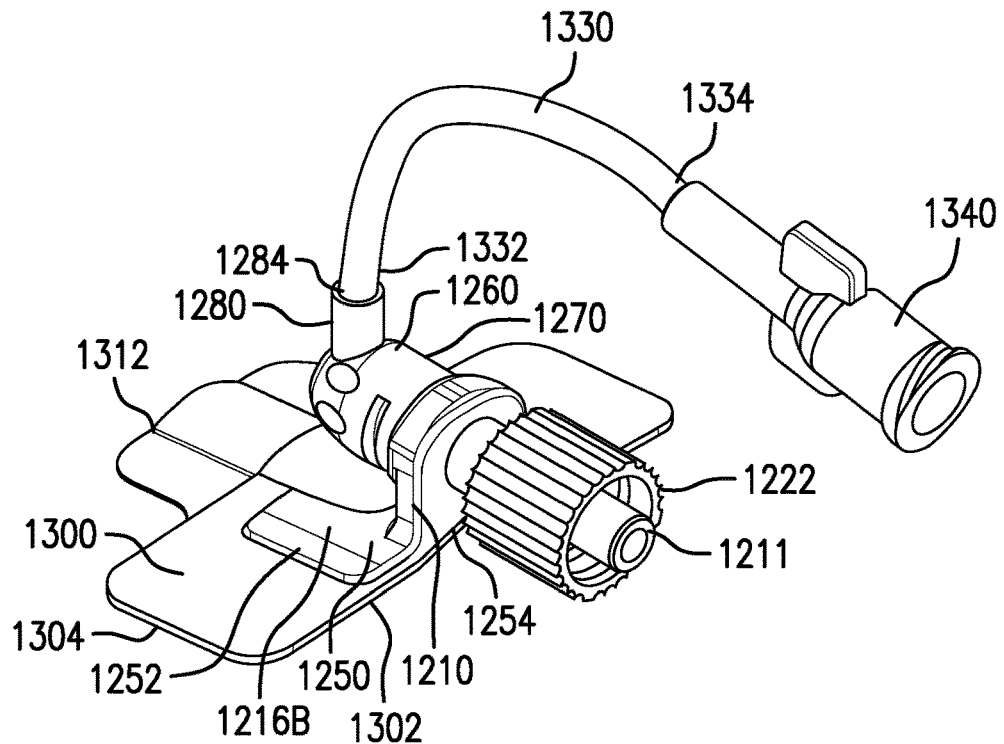
FIGS. 12A-12D schematically show an additional embodiment of a vascular access site management system in a first position, in accordance with further embodiments of the present invention.
Figure 12B:
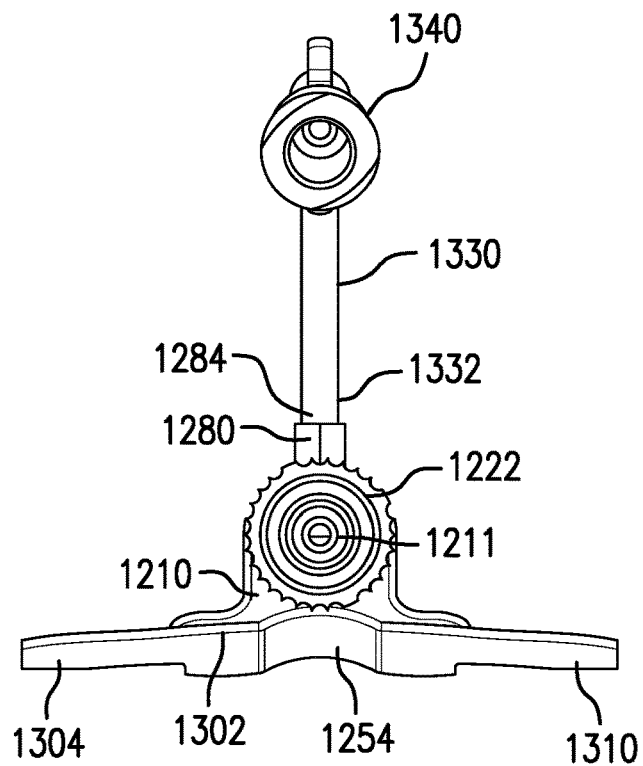
Figure 12C:
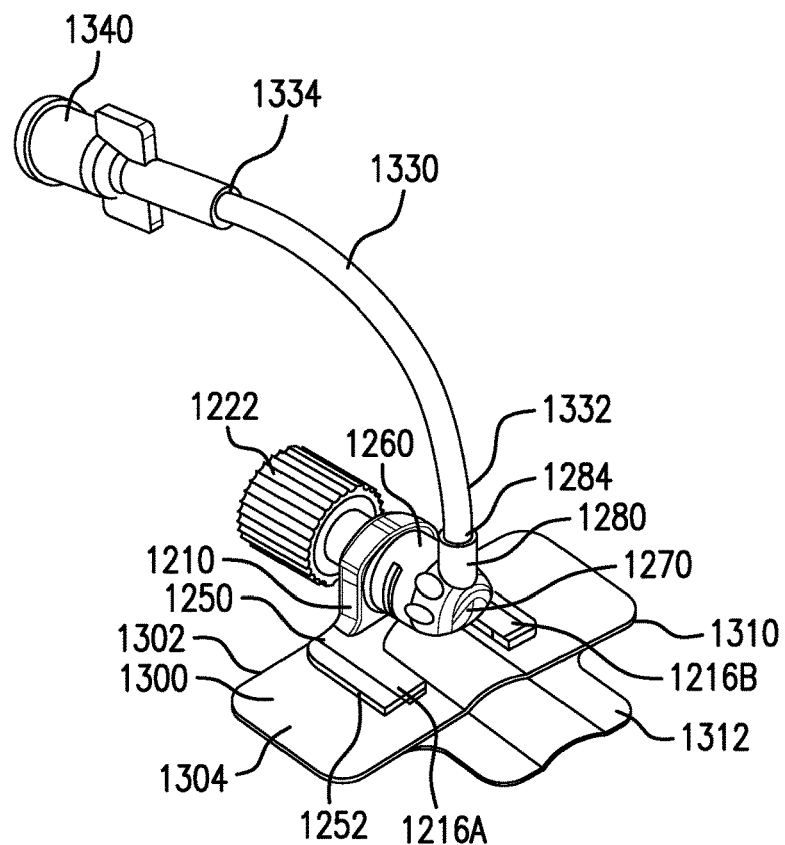
Figure 12D:
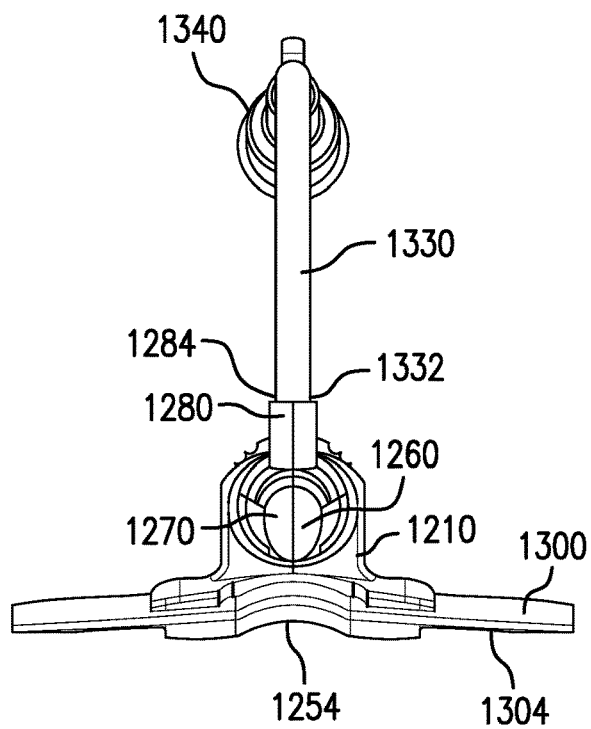
Figure 13A:
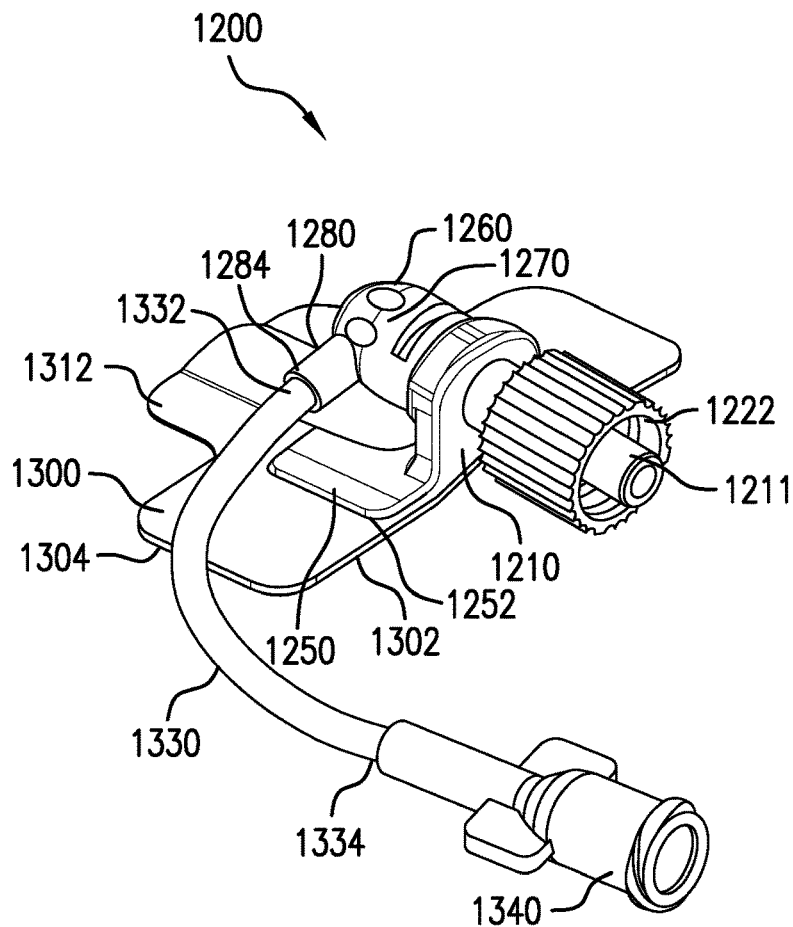
FIGS. 13A-13D schematically show the vascular access site management system of FIGS. 12A-12D in a second position, in accordance with further embodiments of the present invention.
Figure 13B:
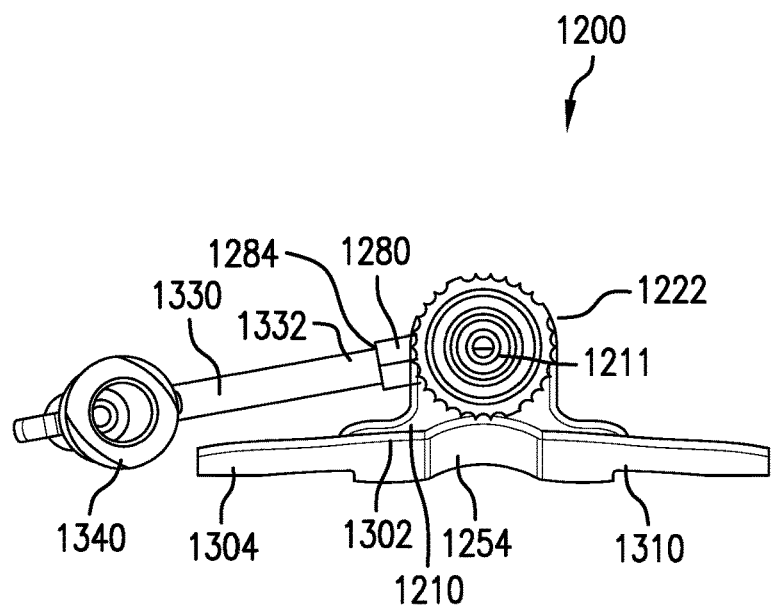
Figure 13C:
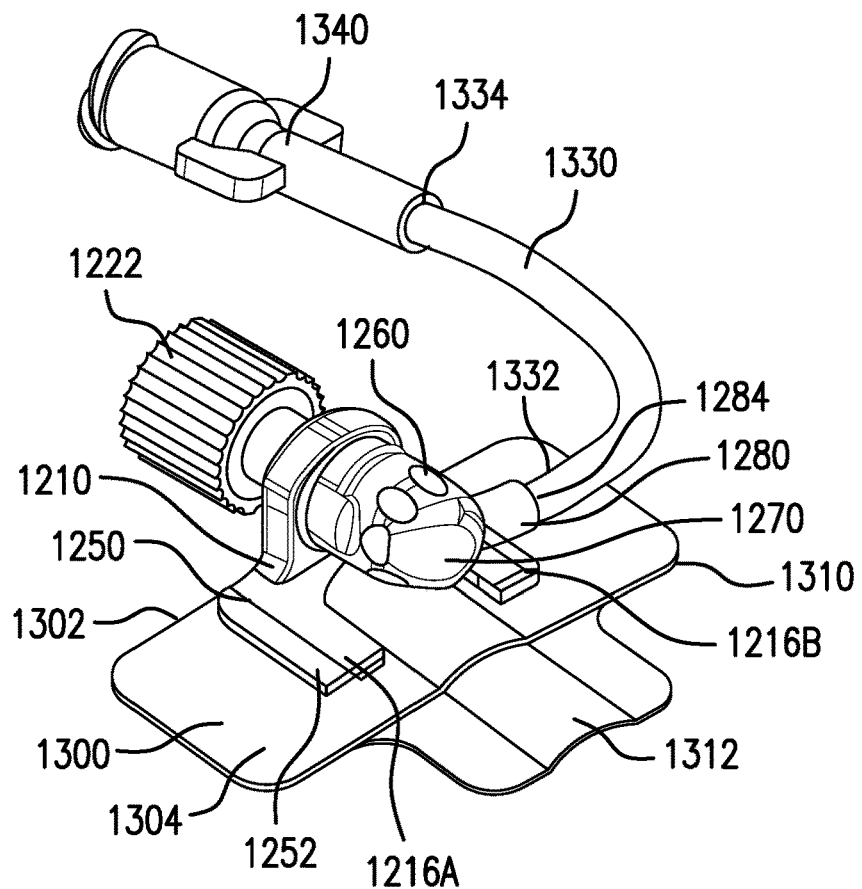
Figure 13D:
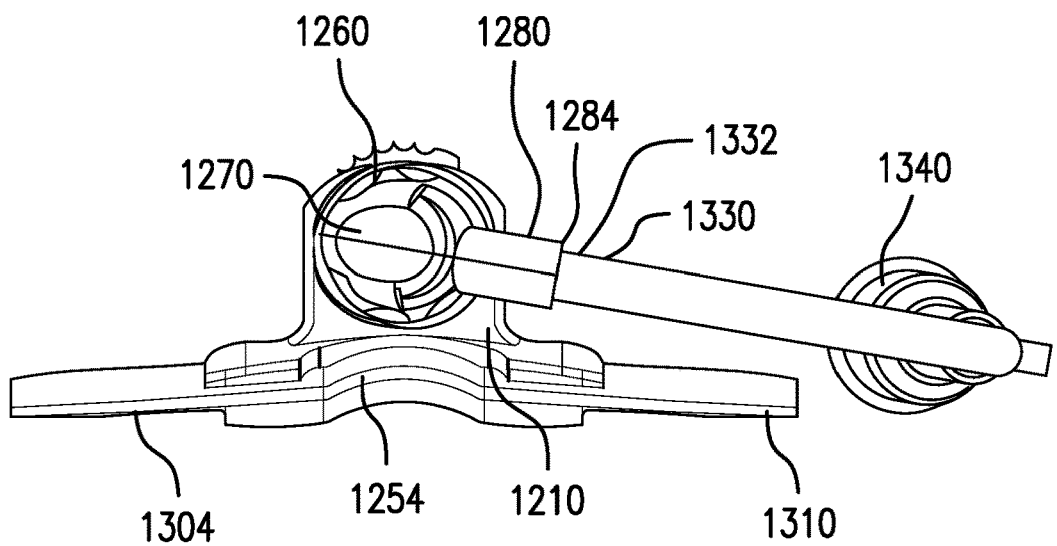
Figure 14A:
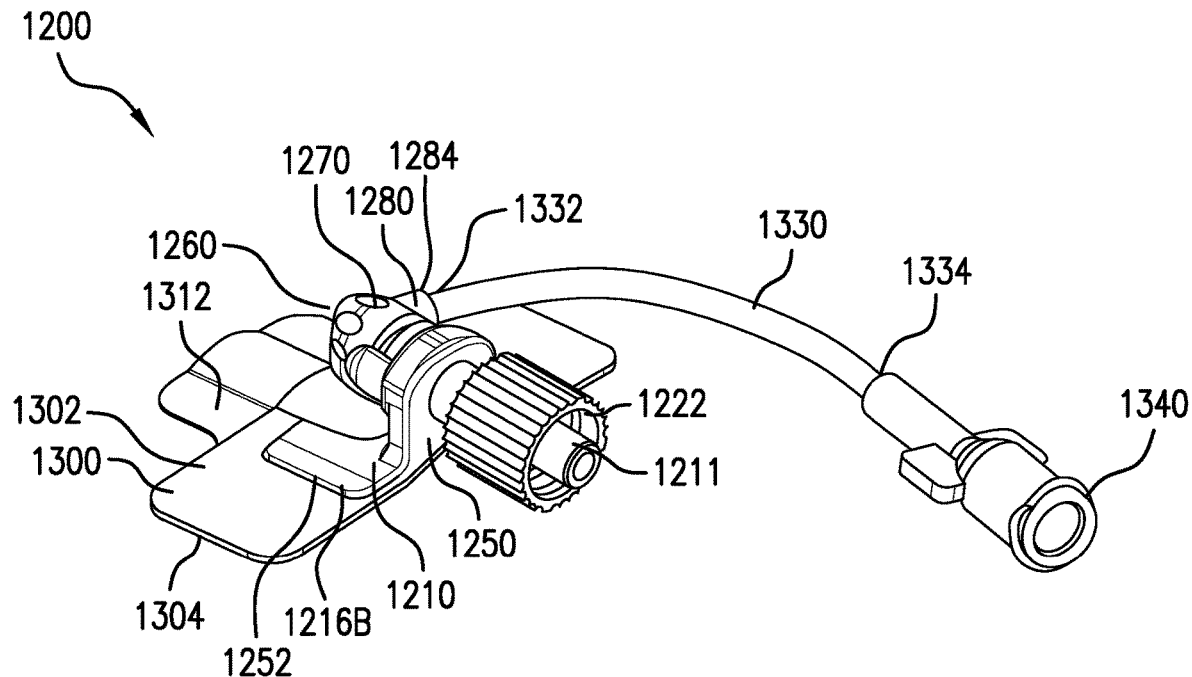
FIGS. 14A-14D schematically show the vascular access site management system of FIGS. 12A-12D in a third position, in accordance with further embodiments of the present invention.
Figure 14B:
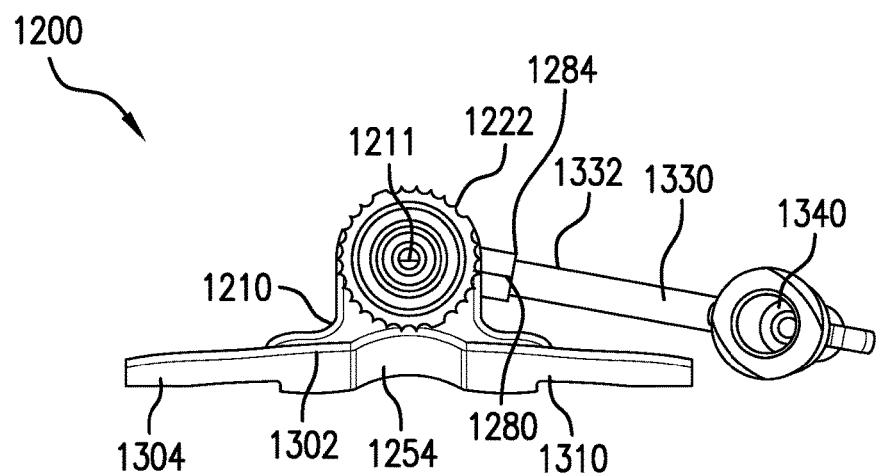
Figure 14C:
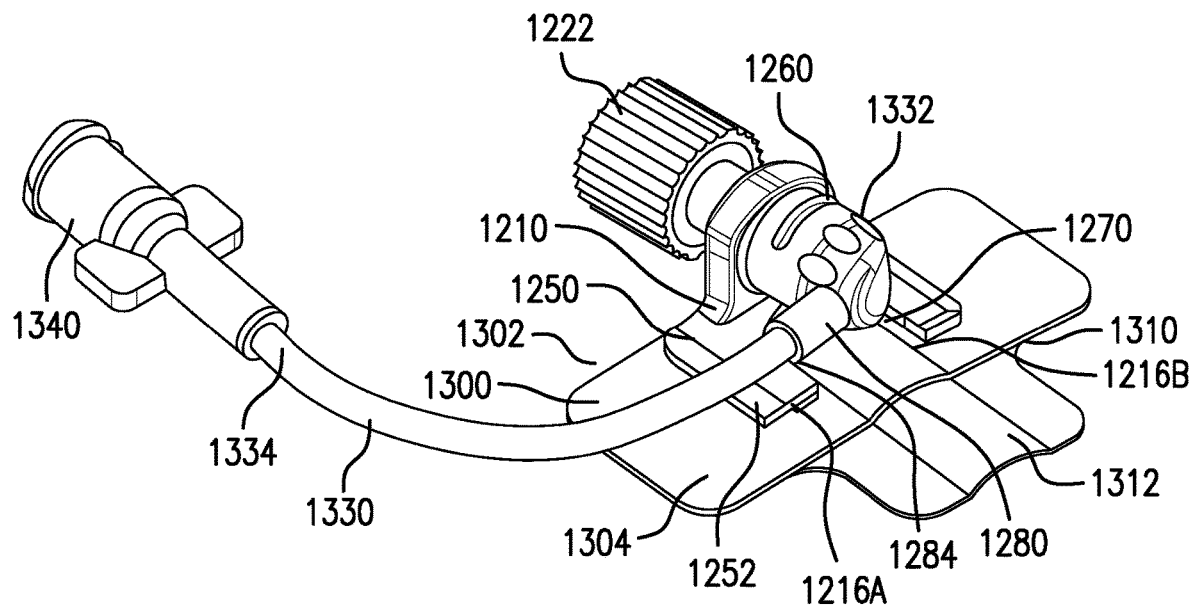
Figure 14D:
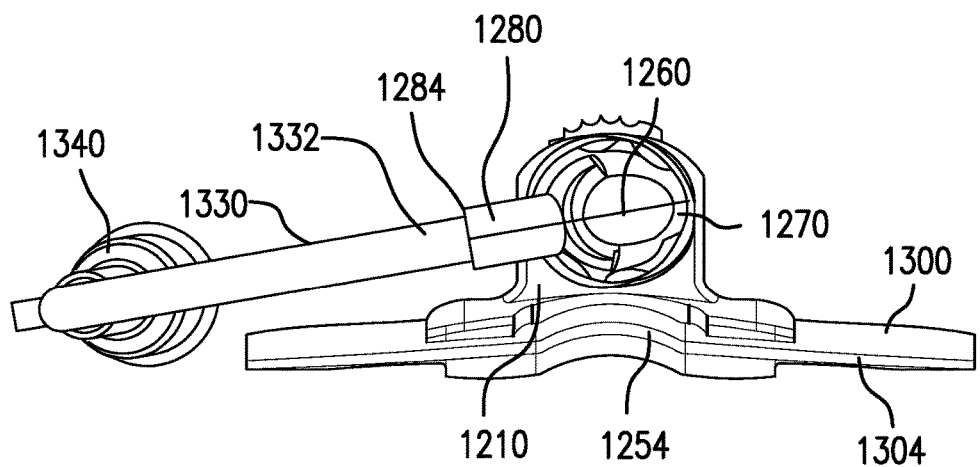
Figure 15:
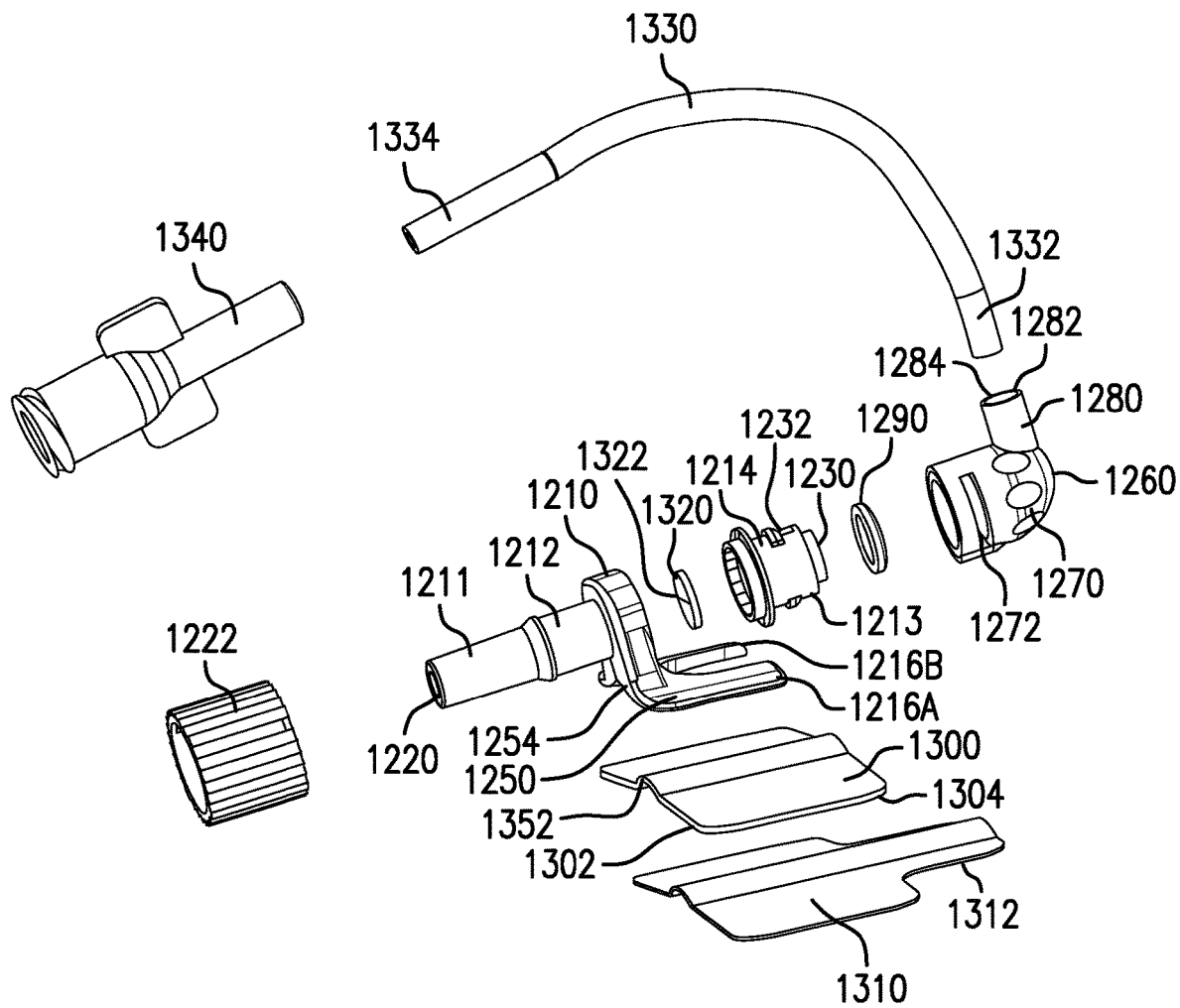
FIG. 15 schematically shows an exploded view of the vascular access site management system of FIGS. 12A-12D, in accordance with some embodiments of the present invention.

As shown in FIG. 11, in embodiments in which the medical implement 610 partially opens the slit, when the distal tip 612 of the medical implement 610 interacts with the valve mechanism 1060, the inner portion 1064 of the valve mechanism 1060 around the slit 1062 may deform and/or move longitudinally towards the first end/outlet 1031 and into the area between the support arms 1036. Conversely, the longitudinal movement (e.g., towards the outlet 1031) of the outer portion 1066 of the slit 1062 may be minimized. For example, as the distal tip 612 begins to interact with the valve mechanism 1060, the outer portion 1066 may contact the support arms 1036 which, in turn, prevent the outer portion 1036 from moving toward the outlet 1031.

It should be noted that, although the engagement member on the device 1000 is described as a protrusion/projection and the engagement member on the medical implement 610 is described as a recess, other embodiments may have different configurations and structures. For example, the engagement member on the medical implement 610 may be a protrusion and the engagement member on the device 1000 may be a recess. Additionally or alternatively, the device 1000 and the medical implement 610 may each have both a protrusion and a recess. In addition, the engagement member on the medical implement 610 may not reside on the arm 616 but alternatively or additionally on a feature or surface(s) that make contact with an engagement member on or near an end 1034 (FIG. 10B) of upper portion 1030, thereby coupling the medical implement 610 with the device 1000 to achieve placement of the distal tip 612 of the medical implement 610 at a predetermined longitudinal position within the flow path 1040.

It should be noted that the engagement between the engagement feature 1070 on the upper portion 1030 and the engagement feature 617 on the medical implement 610 and the contact between the medical implement 610 and the septum 1080 may radially align the distal tip 612 with the flow path (e.g., to keep the distal tip 612 concentric with the flow path 1040). Additionally or alternatively, to further help appropriately position the distal tip 612 (e.g., longitudinally) and to radially align the distal tip 612 with the flow path 1040, the flow path 1040 may include a contact surface 1042 that contacts the outer surface of the medical implement 610. In addition to acting as a stop for the medical implement 610, the contact surface 1042 may also keep the distal tip 612 (and therefore the channel 614) concentric with the opening through the valve mechanism 1060 and the male luer connector 1032. To further help with the radial positioning and keep the distal tip 612 concentric, like the embodiments shown in FIGS. 6A-6E, the device 1000 may have guide ribs (which may be crushable or deformable) extending along a portion of the length of the flow path 1040.

It is important to note that by positioning the medical implement 610 in the manner described above, various embodiments of the present invention provide unobstructed medical article delivery, and like the other embodiments described herein, allow the user to configure the J-loop to the left or right and lock the J-loop in place. Additionally the elastomeric pad 520 and/or the stabilization body 1010 allow for patient comfort and maintains a proper catheter angle (e.g., in a manner similar to that described above).

FIGS. 12-17 schematically show an alternative vascular access site management system 1200 that also rotationally decouples the rotation of a portion of the device (e.g., a flow housing) from the rest of the device and the catheter to which it is connected. In a manner similar to the embodiments described above, the device 1200 may have a stabilization body 1210 with a male luer connector 1211 extending from one side of the stabilization body 1210 and a stabilization body extension 1213 extending from the other side. For example, the stabilization body 1210 may have an inlet body 1214 that forms the stabilization body extension 1213 and an outlet body 1212 that forms the male luer connector 1211. During use, the male luer connector 1211 may connect to the catheter 210. The stabilization device 1210 may include a locking mechanism (e.g., a threaded ring 1222, locking arms, etc.) for securing the male luer connector 1211 to the catheter 210.

Figure 16A:
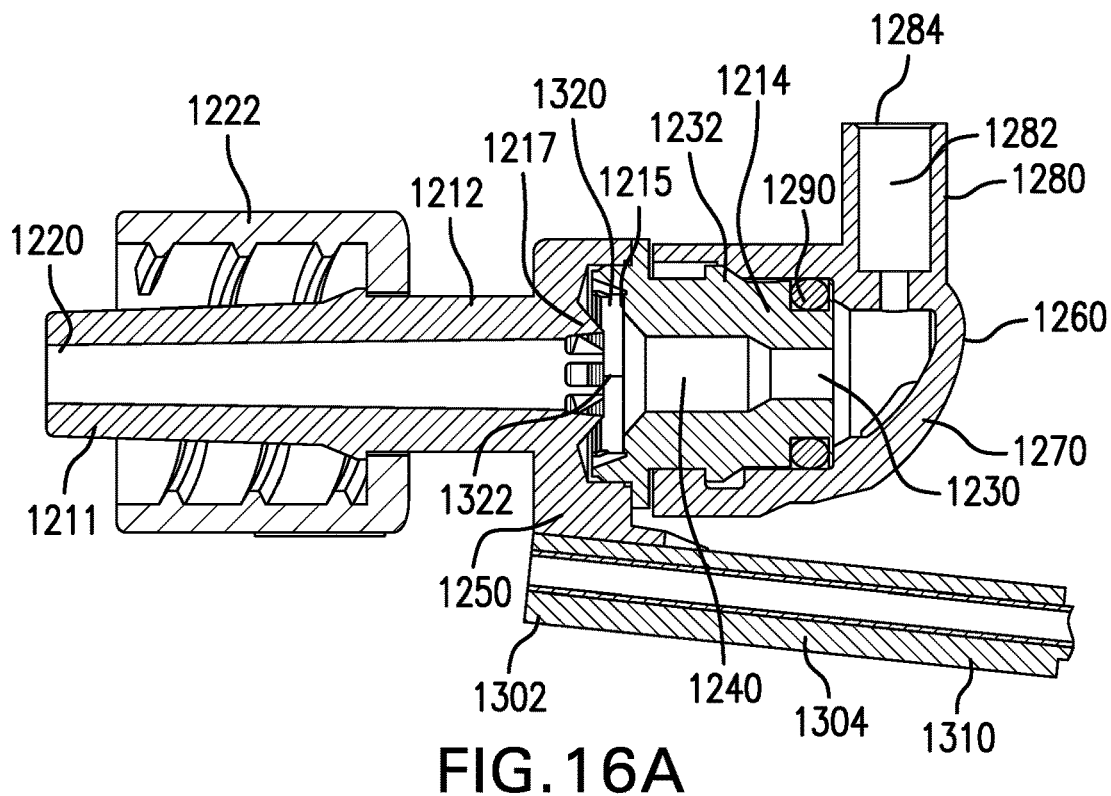
FIG. 16A schematically shows a cross-sectional view of the vascular access site management system shown in FIGS. 12A-12D with a valve mechanism in the closed mode, in accordance with additional embodiments of the present inventions.
Figure 16B:
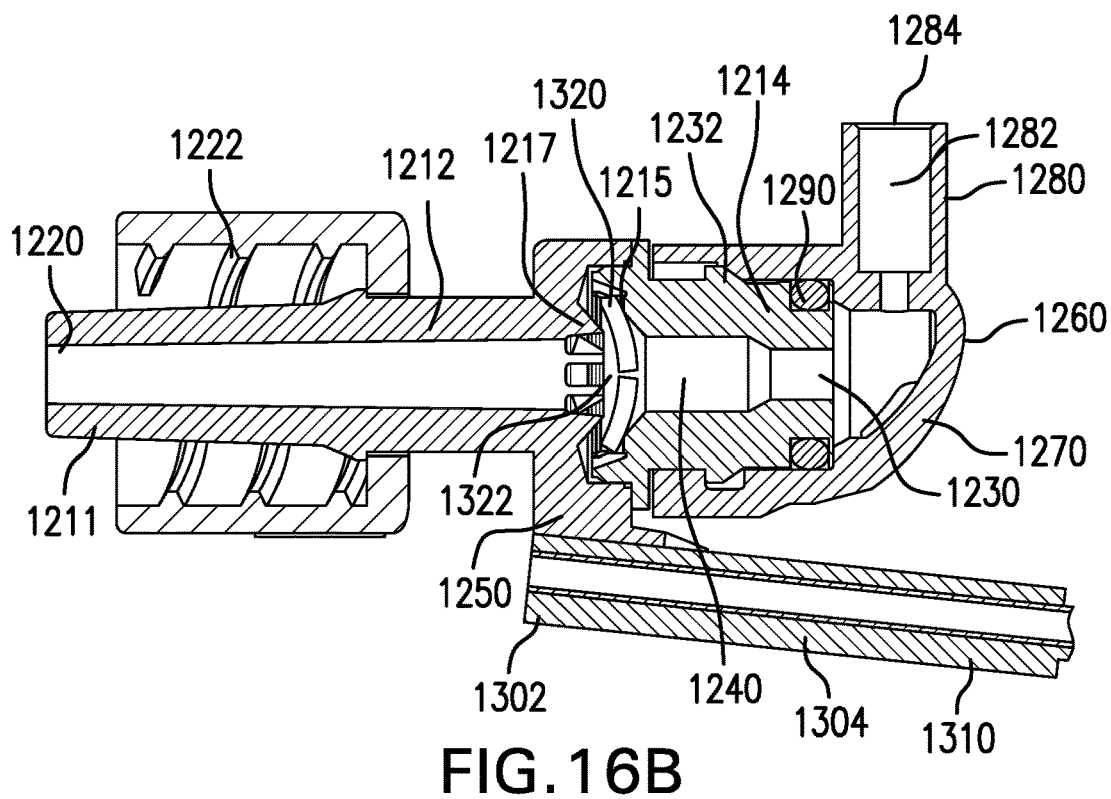
FIG. 16B schematically shows a cross-sectional view of the vascular access site management system shown in FIGS. 12A-12D with a valve mechanism in an open mode for retrograde flow, in accordance with additional embodiments of the present inventions.
Figure 16C:
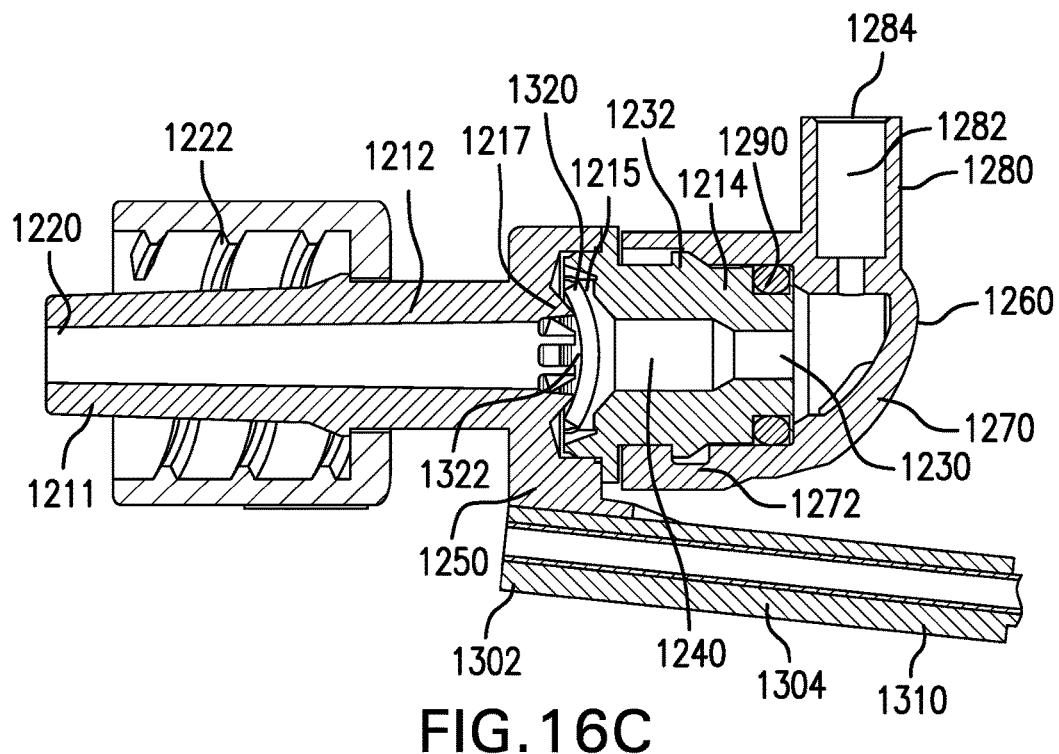
FIG. 16C schematically shows a cross-sectional view of the vascular access site management system shown in FIGS. 12A-12D with a valve mechanism in an open mode for forward flow, in accordance with additional embodiments of the present inventions.

As best shown in FIGS. 16A and 16B, the stabilization body 1210 may have an internal fluid path 1240 extending though the stabilization body 1210. The inlet 1230 of the fluid path 1240 may be located within the inlet body 1214 and the outlet 1220 of the fluid path 1240 may be located within the outlet body 1212. Within the fluid path 1240 and to control the flow of fluid through the internal fluid path 1240, the stabilization body 1210 may have a valve mechanism 1320 that is positioned within/between the inlet body 1214 and the outlet body 1212. For example, the valve mechanism 1320 may be a two-way pressure activated valve (PAV) with a slit 1322 extending through it. As described in greater detail below, the valve mechanism may deform in the presence of a forward pressure (e.g., from the inlet 1230 towards the outlet 1220) to allow fluid to flow around the valve mechanism 1320 and through the stabilization body 1210. Additionally, in the presence of a retrograde pressure (e.g., from the outlet 1220 toward the inlet 1230), the slit 1322 may open to allow fluid flow through the stabilization body 1210 from the outlet 1220 toward the inlet 1230. It should be noted that, to avoid low pressure flow (e.g. blood reflux) through the valve mechanism 1320, the pressure required to open the slit in the retrograde direction should be greater than the venous pressure of the patient.

In addition to being positioned between the inlet body 1214 and the outlet body 1212, the stabilization body 1210 may include a number of support arms 1217 within the fluid path 1240 that mechanically support the valve mechanism 1320 within the fluid path 1240. To that end, as the valve mechanism 1320 deforms (e.g., in the presence of the forward pressure), the valve mechanism 1320 may deform away from a seating/sealing surface 1215 within the stabilization body 1210 and over the support arms 1217 to allow the fluid flow from the inlet 1230 toward the outlet 1220, around the valve mechanism 1320 and between the spaces between the support arms 1217. Additionally, the support arms 1217 may be located radially inward from the seating/sealing surface 1215 to promote deformation (e.g. bending) of the valve mechanism 1320 around the support arms 1217 in the presence of the forward pressure. It should be noted that, although the figures show eight support arms 1217 other embodiments may have more or less than eight support arms 1217. For example, some embodiments may have seven or less support arms 1217 and other embodiments may have nine or more support arms 1217. Furthermore, the number of support arms 1217, their width(s) and contact area(s), and the amount of open space between each support arm 1217 will at least partially influence the degree that the valve mechanism 1320 bends around the support arms 1217 and the size of the opening between the seating/sealing surface 1215 and valve mechanism 1320 (e.g. size of flow path).

To help stabilize the device 1200 on the patient, the stabilization body 1210 may include a base portion 1250 with a stabilization surface 1252 located on an underside of the base portion 1250 that stabilizes the device/system 1200 on the patient. Additionally or alternatively, the base portion 1250 may include a separate stabilization base 1300 that is located on the underside of the base portion 1250. In some embodiments, the device 1200 may have a first securement portion 1302 and, perhaps, a second securement portion 1304 located on the underside of the stabilization base 1300 (or the underside of the base portion 1250). In a manner similar to that described above for prior embodiments, the first and/or second securement portion 1302/1304 may include an adhesive layer that secures the device 1200 to the patient. For example, the first securement portion 1302 may have a light tack adhesive layer and the second securement portion 1304 may have a stronger tack adhesive layer (e.g., an adhesive that is stronger than the adhesive on the first securement portion 1302). As noted above, the first securement portion 1302 with the light tack adhesive allows the user to position and reposition the system/device 1200 as needed. The second securement portion 1304 with the stronger adhesive allows the user to firmly secure the system/device 1200 to the patient once the device/system 1200 is in place.

In addition to or instead of the adhesive, the first securement portion 1302 may include a gripping or conforming structure that grips and/or conforms to the patient's skin to allow the user to initially position the device 1200 and hold the device 1200 in place while the second securement portion is secured to the patient or instead, no different than the first securement portion. For example, the first securement portion 1302 may include silicone structures (e.g., protrusions, ribs, etc.) that grip and/or conform to the surface of the patient's skin.

Like the adhesive sections 112/114 described above, the first securement portion 1302 may be located at the leading or trailing edge of the stabilization base 1300 (or base portion 1250 of the stabilization body 1210) and the second securement portion 1304 may be located on the remainder of the stabilization base 1300 or base portion 1250. To prevent the securement portions 1302/1304 and their respective adhesives from inadvertently sticking to the wrong surface and/or prevent bacteria/contamination from sticking to the adhesive, the device 1200 may have one or more liners 1310 covering the adhesive. The liner 1310 may have a tab 1312 so that the liner 1310 can be easily removed. In some embodiments, the first and second securement portions 1302/1304 may have their own liners that can be removed independently as needed.

As discussed above, it may beneficial to reduce the force/pressure on the catheter 210 and keep the fluid path 1240 in line with the catheter 210. To that end, the base portion 1250 and/or the stabilization base 1300 may be configured at an angle with respect to the outlet 1220 of the stabilization body 1210 (e.g., with respect to the longitudinal axis of the outlet 1220). For example, the stabilization base 1300 and/or base portion 1250 may be at an angle that complements the angle of the catheter 210 extending out of the patient (e.g., between 5-10 degrees).

Figure 17A:
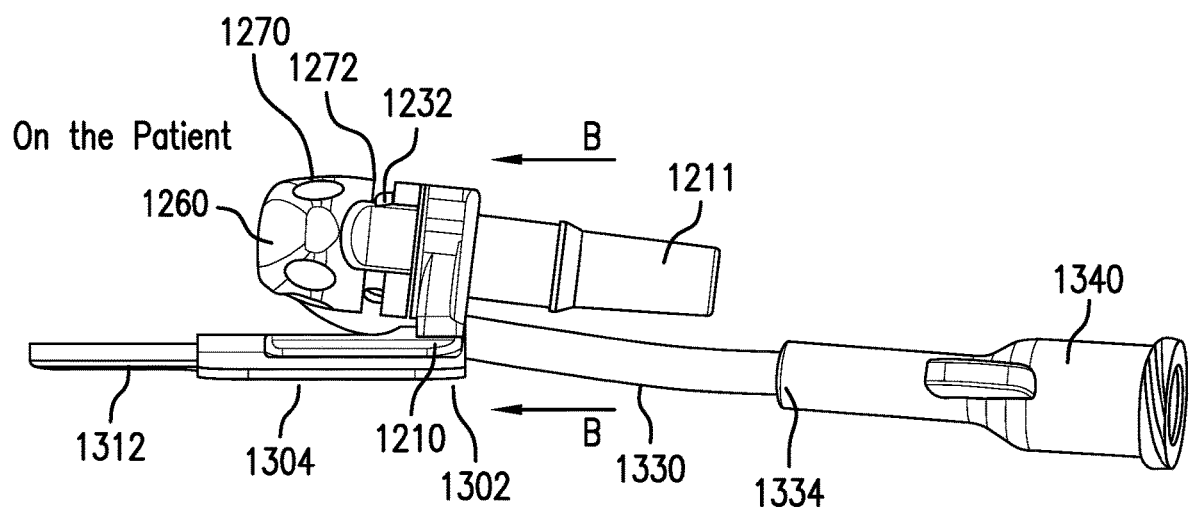
FIGS. 17A-17C schematically show the vascular access site management system of FIGS. 12A-12D with a vein relief area, in accordance with some embodiments of the present invention.
Figure 17B:
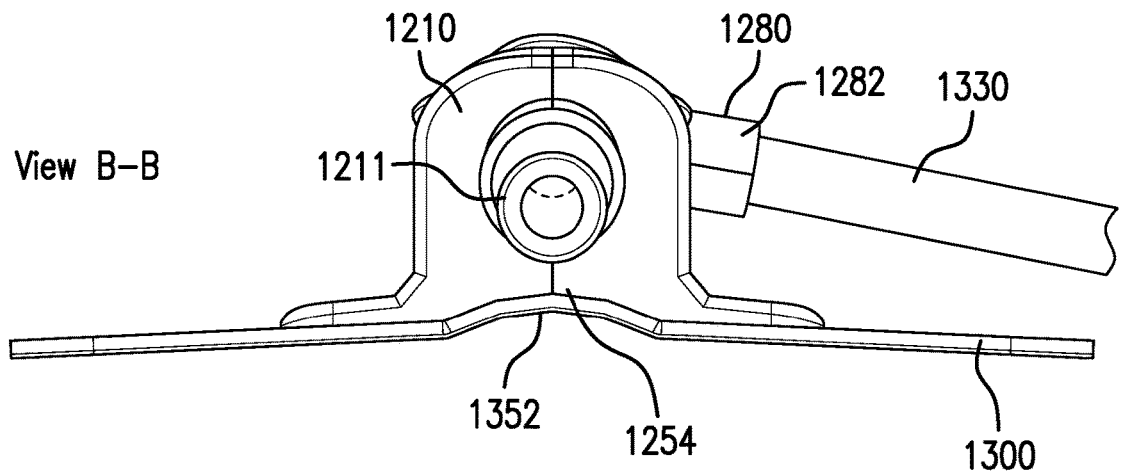
Figure 17C:
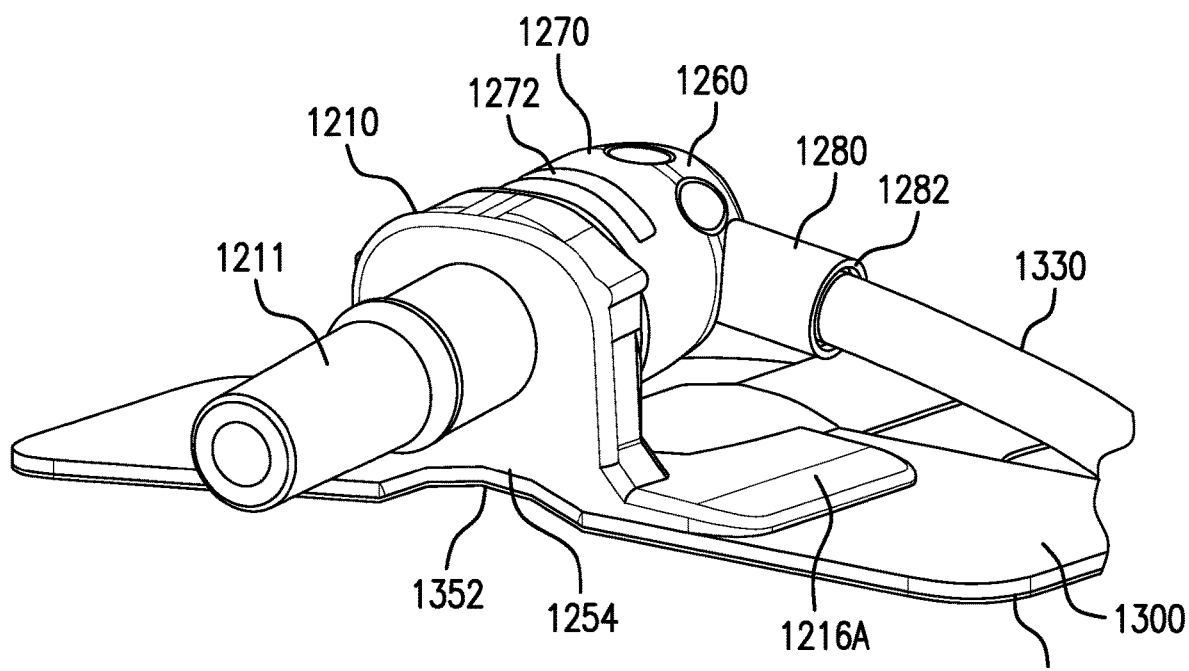

Once the device/system 1200 is in place and secured to the patient, it may be located over a portion of the vein in which the catheter 210 is inserted. To help relieve the pressure applied to the patient over the vein (and reduce any distortion of the vein by the device 1200), some embodiments of the device/system 1200 may include a vein relief zone 1254 within the base portion 1250 (as shown in FIGS. 17A-17C). The vein relief zone 1254 has a recessed surface and is axially aligned with the outlet 1220. Additionally, the relief zone 1254 may include adhesive (e.g., on the base portion 1250 and/or adhesive 1352 on the stabilization base 1300) that lifts the patient's skin that is over the vein to further reduce the pressure on the vein.

To facilitate the flow of fluids in and out of the patient, the device 1200 may have a flow housing 1260 that is connected to the stabilization body 1210 and has a sleeve portion 1270 and a pathway portion 1280 extending from the sleeve portion 1270. As the name suggests, the pathway portion 1280 may include a flow path 1282 that extends through it and that is fluidly connected to the fluid path 1240 within the stabilization body 1210 to allow fluid to pass through the device 1200. The inlet 1284 of the flow path 1282 may connect directly to a medical implement used to transfer fluid to and/or from the patient through the device 1200. Alternatively, the device 1200 may include a tube 1330 that is connected to the inlet 1284 of the flow path 1282 at a first end 1332 and a medical connector (e.g., a female luer connector 1340), a needle free connector (not shown) or other medical device such as a luer activated valve (not shown) at the second end 1334.

As best shown in FIGS. 12A-12D, 13A-13D, and 14A-14D, the flow housing 1260 may be rotatably connected to the stabilization body 1210 such that flow housing 1260 can rotate between a first position (FIGS. 12A-12D), a second position (FIGS. 13A-13D) and a third position (FIGS. 14A-14D). To that end, the inlet body 1214 of the stabilization body 1210 may have a protrusion 1232 extending from a surface of the inlet body 1214. Conversely, the sleeve portion 1270 may include a recess 1272 into which the protrusion 1232 may snap during assembly of the device 1200. To allow the flow housing 1260 to rotate with respect to the stabilization body 1210, the recess 1272 may be substantially larger/longer that the protrusion 1232 such that the protrusion 1232 slides within the recess 1272 during rotation. To further help rotation and prevent leakage between the stabilization body 1210 and the flow housing 1260, the device 1200 may include an o-ring 1290 between an outer diameter/surface of the stabilization body 1210 and an inner diameter/surface of the flow housing 1260. The o-ring 1290 may also provide some rotational resistance so that the flow housing 1260 does not accidentally rotate.

It should be noted that, although the stabilization body 1210 is described above as having a protrusion 1232 and the flow housing 1260 is described as having a recess 1272 to facilitate the rotation of the flow housing 1260 with respect to the stabilization body 1210, other embodiments may have different configurations. For example, in some embodiments, the stabilization body 1210 may have a recess into which a protrusion extending inward from an inner surface of the flow housing 1260 may snap into and slide within during rotation.

In a manner similar to that described above, the device 1200 may be used to transfer fluids to and/or from a patient and minimize the stress on the catheter 210 and access site. For example, the user (e.g., the medical personnel) may first connect a medical implement to the female luer connector 1340 (or other needle-free connector) or directly to the inlet 1284 of the flow path 1282 and flush (e.g., prime) the device 1200, for example, with saline. Once the device 1200 is flushed/primed, the user may insert the catheter 210 into the patient (e.g., into the patient's arm).

The user may then connect the catheter 210 to the management device 1200. When attaching the catheter 210 and securing the stabilization device 1200, the user may grab the stabilization body 1210 and press the device 1200 against the catheter 210. If so equipped, the user may then screw the ring 1222 of the male luer connector 1212 onto the catheter 210 to secure the device 1200 to the catheter 210. Once the catheter 210 is attached, the user may then remove the liner 1310 stick the stabilization base 1210 to the patient (e.g., via the securement portion(s) 1302/1304).

It should be noted that, if the device 1200 has more than one securement portion (e.g., the first securement portion 1302 and second securement portion 1304 discussed above) and each securement portion has its own liner, the user may remove the liner for the first securement portion 1302 first. Once the first securement portion 1302 is adhered to the patient and the user has confirmed that there is adequate flow through the system 1200 (e.g., as described above), the user may remove the liner 1310 for the second securement portion 1304 to further secure the system 1200 to the patient.

After the vascular access site management system 1200 is secured or at a time preferable to the user, the user may rotate the flow housing 1260 (and the tube 1330 and female luer connector 1340 if equipped) to either the right or the left (e.g., from the upright position shown in FIGS. 12A-12D to the position shown in FIG. 13A-D or 14A-D). If needed, the user may then place a dressing over at least the catheter insertion site to maintain the cleanliness of the site. It should be noted that, like the embodiments described above, the user may choose either a left or right configuration based on what is the best configuration for the given application.

Figure 18:
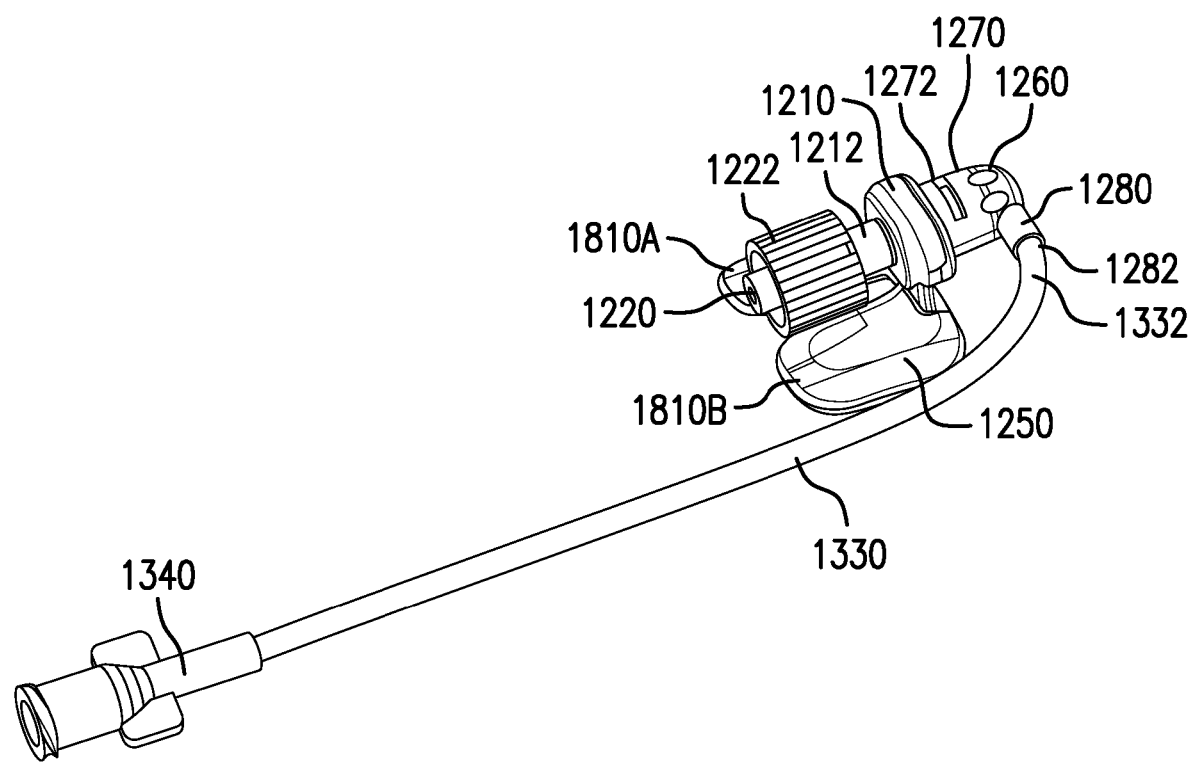
FIG. 18 schematically shows an additional embodiment of a vascular access site management system with an alternate base direction, in accordance with further embodiments of the present invention.

Although the embodiment discussed above has a base portion 1250 that is a split base with two legs 1216A/B that extend out from the base portion 1250 and toward the flow housing 1260 (e.g., and away from the male luer connector 1211), other embodiments may have different base configurations. For example, as shown in FIG. 18, the base portion 1250 may have legs 1810A/B that extend toward the male luer connector 1211 and away from the flow housing 1260. Alternatively, some embodiments may have legs that extend in both directions or may only have a single leg (e.g., as opposed to being a split base with more than one leg).

It is important to note that the embodiments described herein, provide numerous benefits. For example, because the devices may be rotated in either direction, the embodiments described above, allow the user to configure the J-loop to either the left or right side and, in some embodiments, lock it in place. Various embodiments also provide two stage stabilization. During the first stage, the clinician has an important "extra hand" during the venous access procedure and the second stage secures catheter to the body to restrict catheter movement and reduce associated clinical complications, such as phlebitis and infiltration/extravasation. The embodiments described herein also reduce the potential for kinking in the tube, reduces clinical variation, and provide a means for the user to know the location of the catheter tip relative to a datum on the device.

Figure 19A:
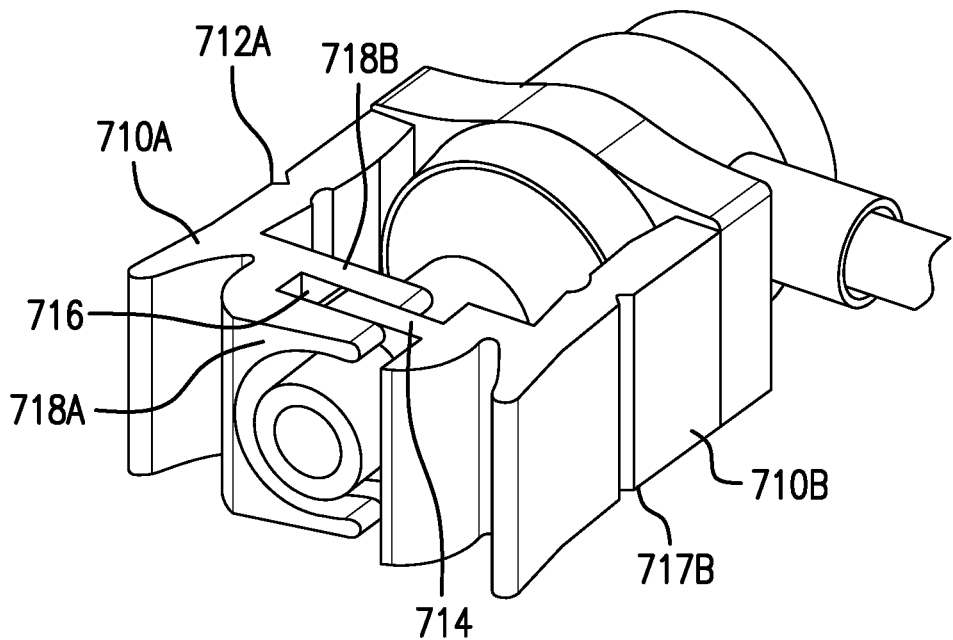
FIGS. 19A-19D schematically show an alternative embodiment of a locking mechanism for locking the vascular access site management system to the catheter, in accordance with some embodiments of the present invention.
Figure 19B:
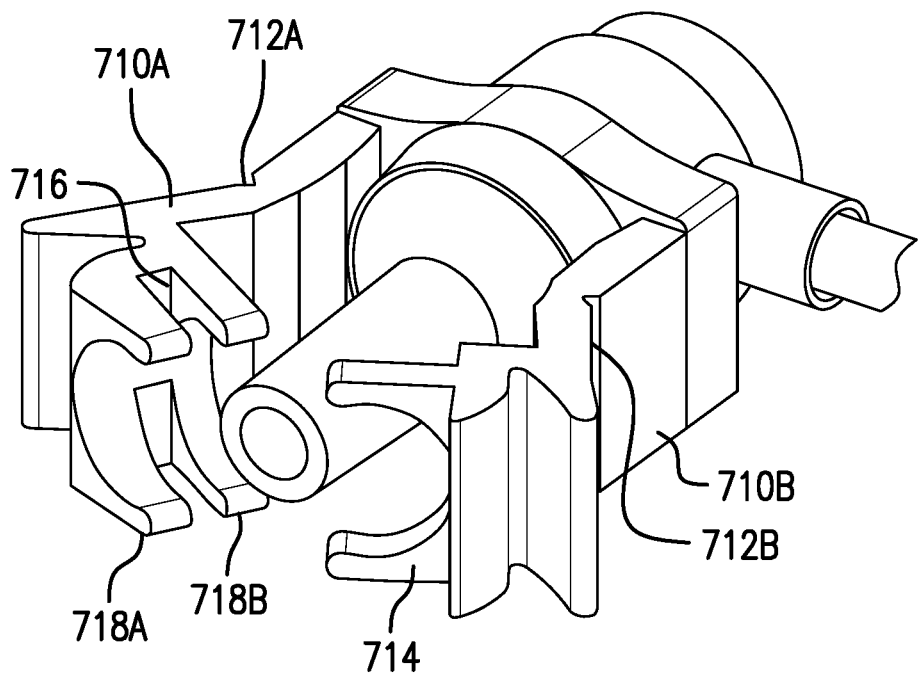
Figure 19C:
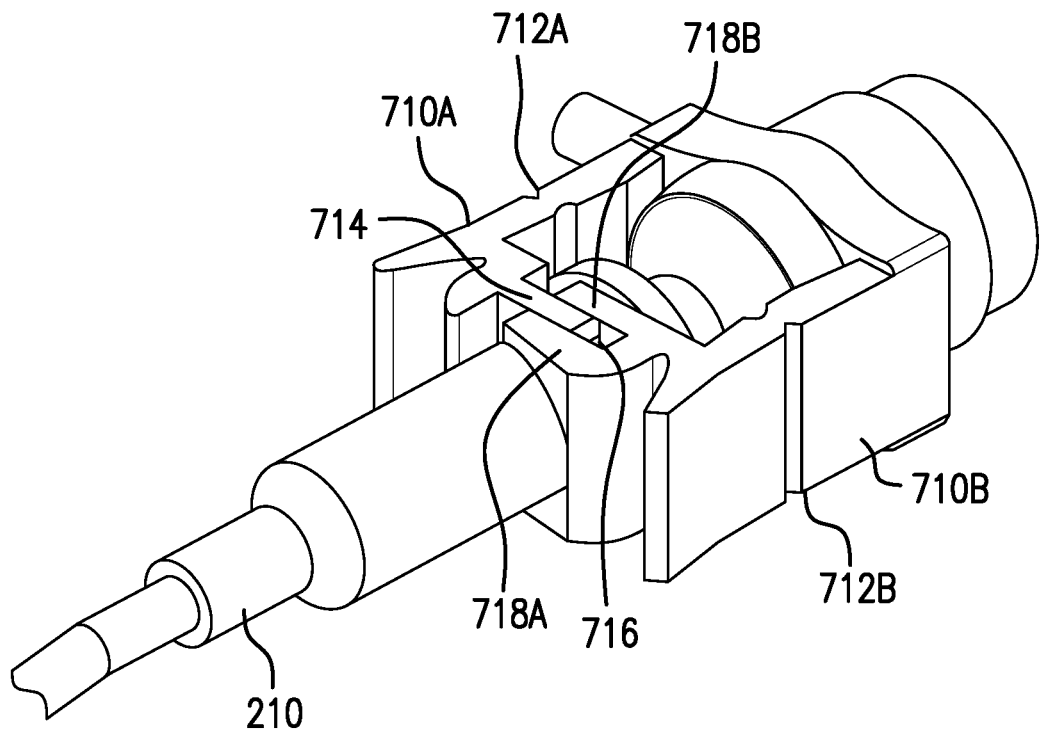
Figure 19D:
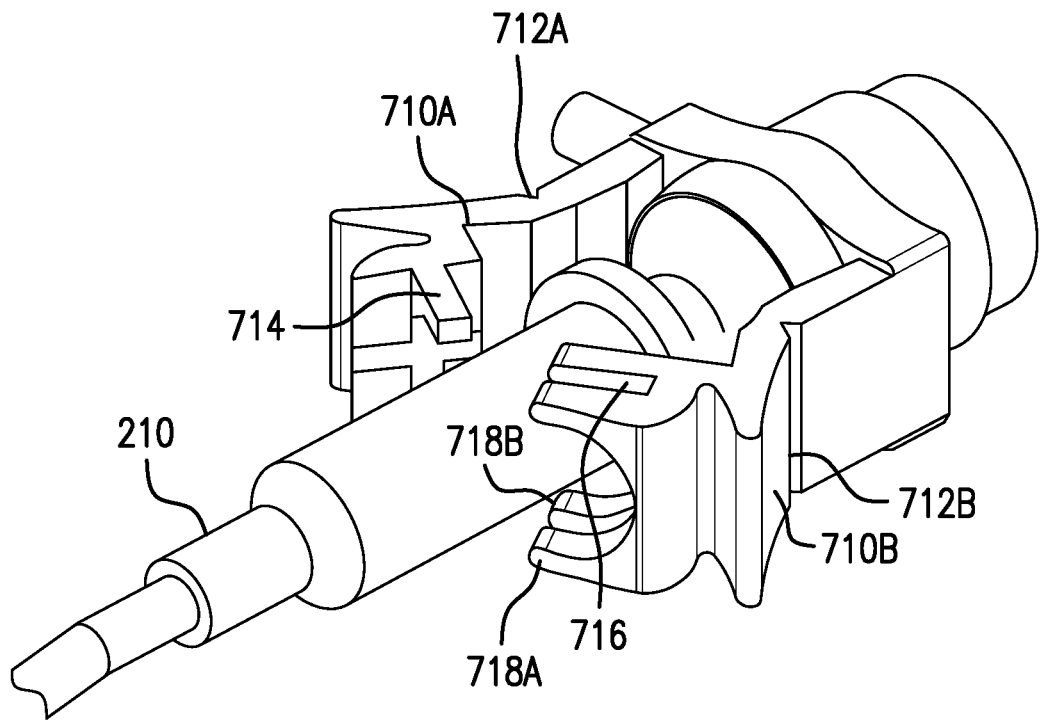

Although the embodiments described above utilize locking arms (e.g., arms 130A/130) and/or a standard rotating collar/ring (e.g., ring 552) to secure the catheter 210 to the vascular access site management systems, other embodiments may utilize different structures. For example, as shown in FIGS. 19A to 19D, the device may have locking arms 710A and 710B within hinges 712A/B (e.g., living hinges) that allow the arms to flex between an open mode (FIGS. 19B and 19D) and a closed mode (FIGS. 19A and 19C). One of the arms 710A may have a protrusion 714 that enters a recess 716 (e.g., formed by two protrusion 718A/B) on the other arm 710B when in the closed mode to secure the catheter 210 (FIG. 19C).

Figure 20A:
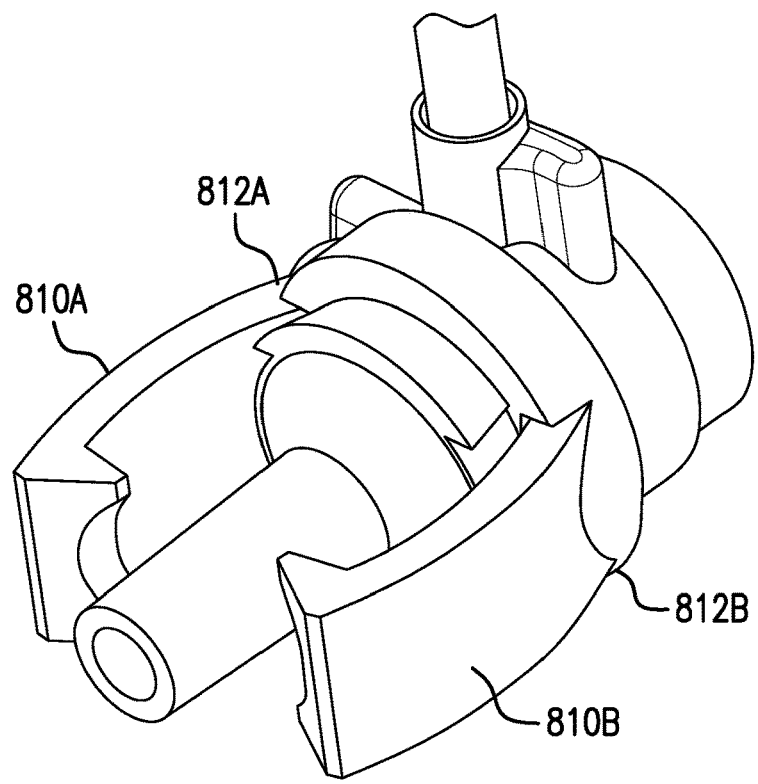
FIGS. 20A-20D schematically show an additional alternative embodiment of a locking mechanism for locking the vascular access site management system to the catheter, in accordance with some embodiments of the present invention.
Figure 20B:
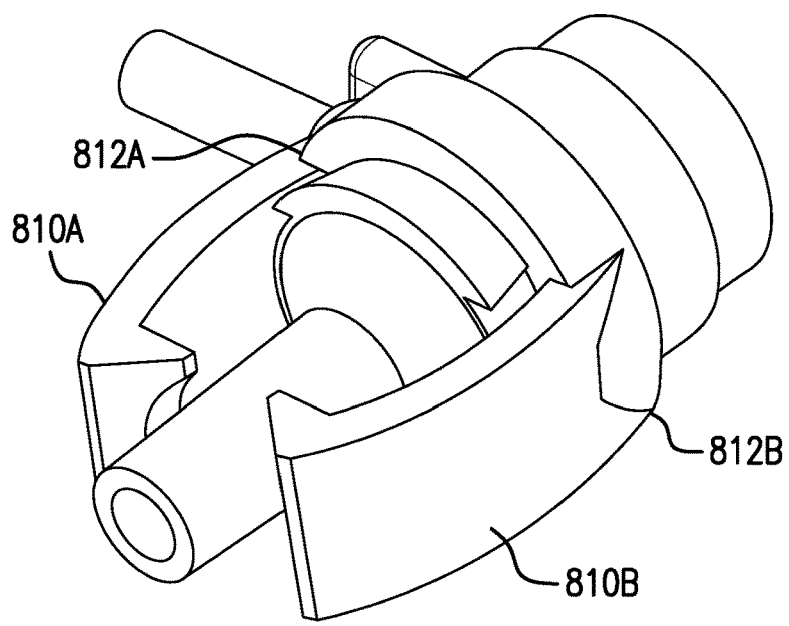
Figure 20C:
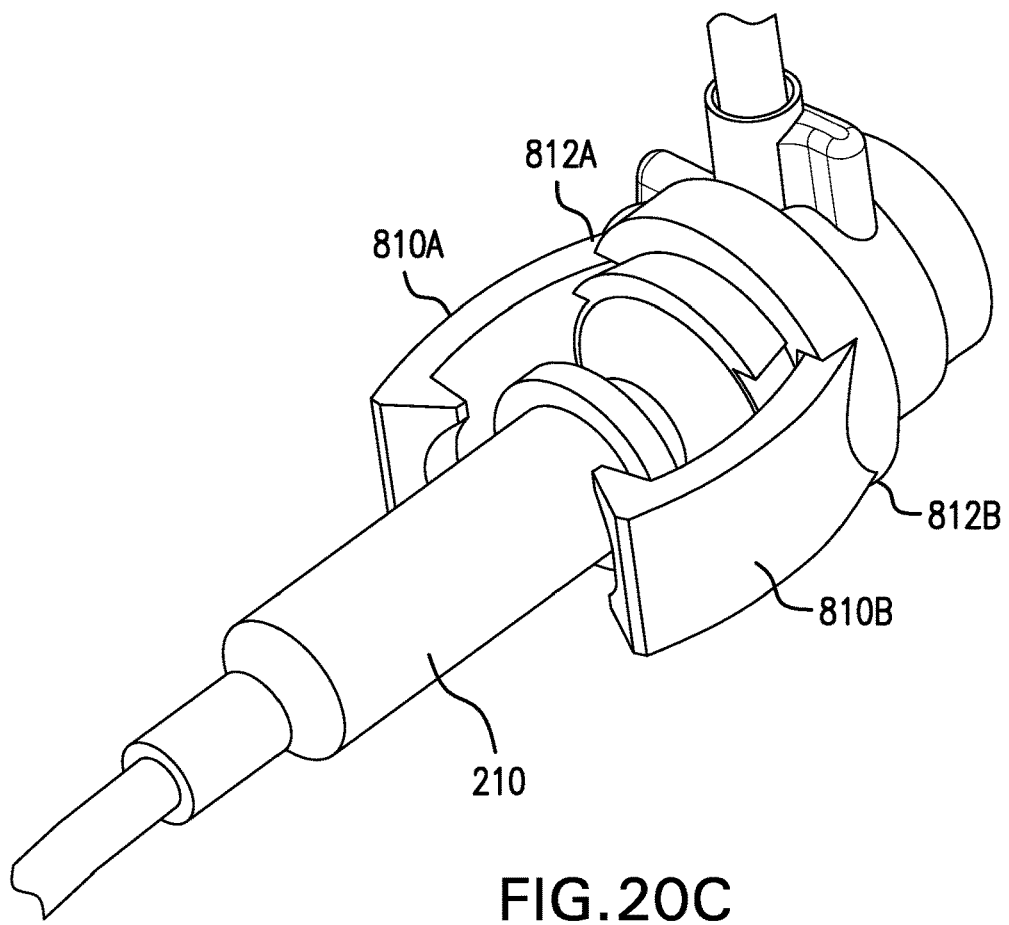
Figure 20D:
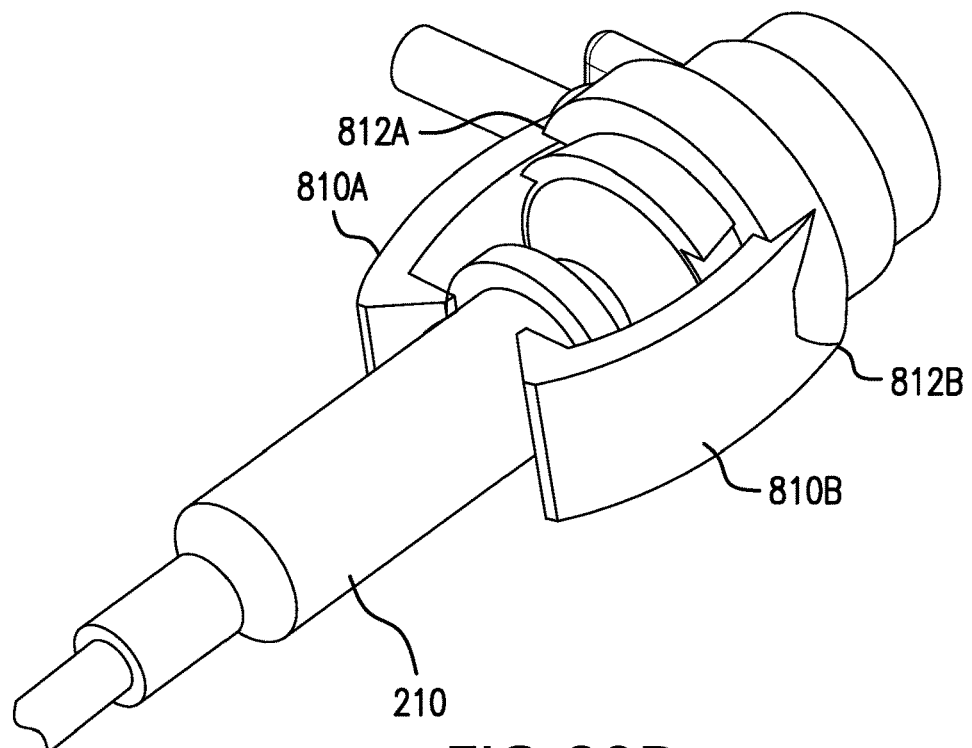

FIGS. 20A-20D show a further alternatively locking mechanism for the catheter 210. Like the locking arms 130A/B described above, the embodiment shown in FIGS. 20A-20D also has arms 810A/B extending from the device. However, the arms 810A/B may be attached to the rest of the device via hinges 812A/B. The hinges 812A/B allow the arms 810A/B to transition between an open mode (FIG. 20A/20C) and a closed mode (FIGS. 20B and 20D).

Figure 21A:
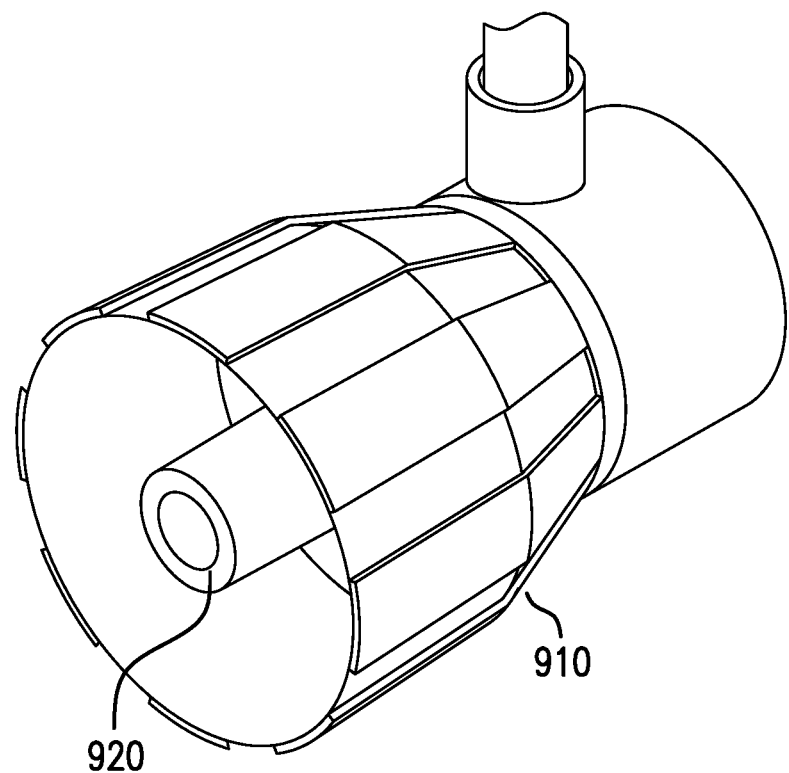
FIGS. 21A-21D schematically show a further alternative embodiment of a locking mechanism for locking the vascular access site management system to the catheter, in accordance with some embodiments of the present invention.
Figure 21B:
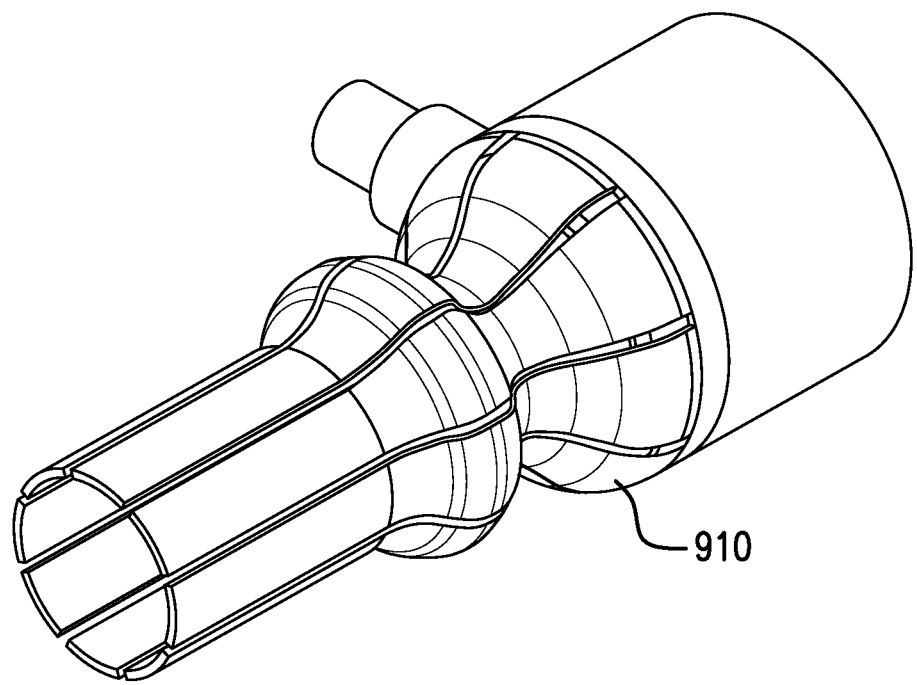
Figure 21C:
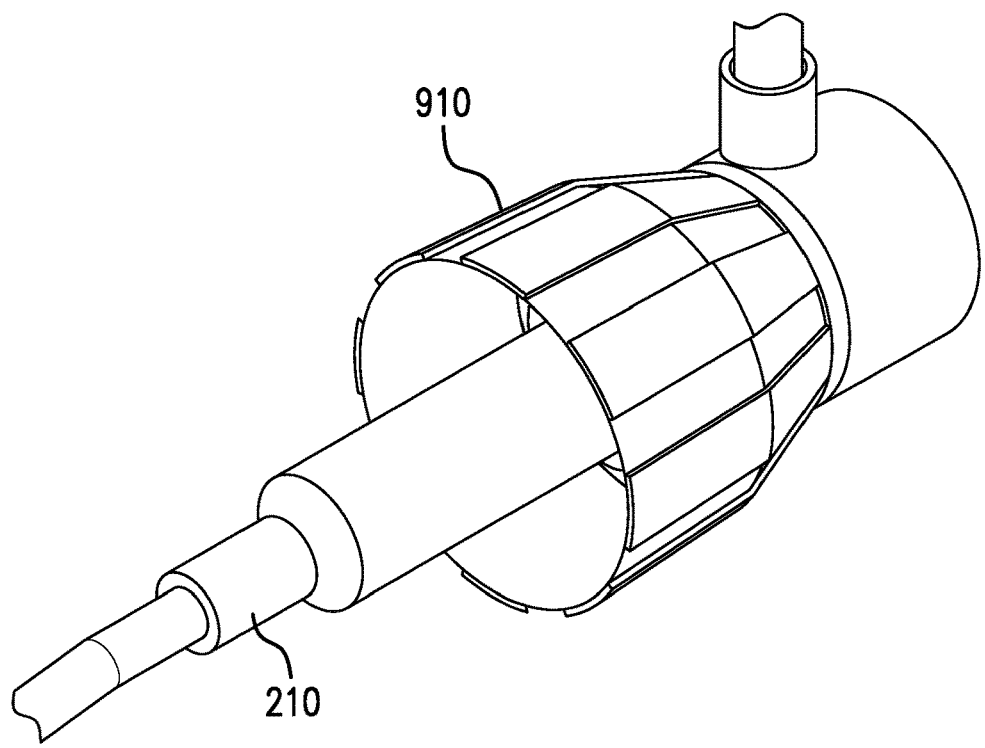
Figure 21D:
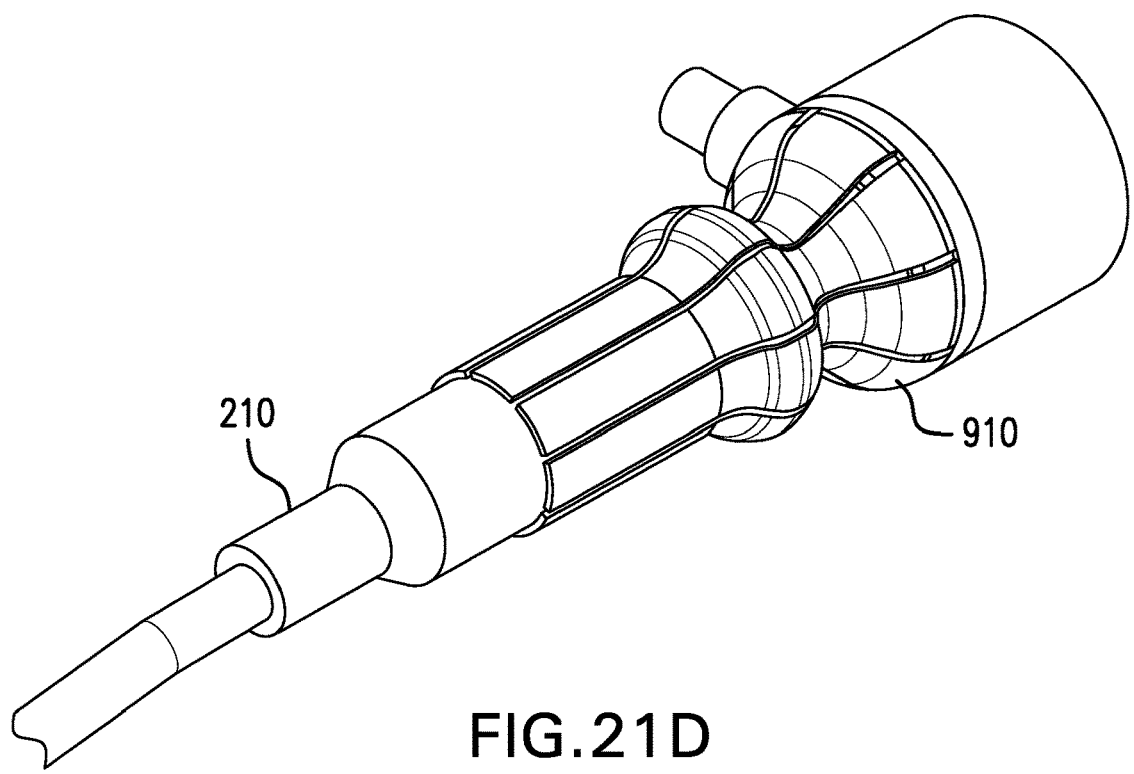

FIGS. 21A-21D show a further embodiment of a locking mechanism that may be used with the vascular access site management systems described herein. This locking mechanism may include a skirt 910 that can transition between an open mode (FIGS. 21A and 21C) and a closed mode (FIGS. 21B and 21D). For example, once the catheter 210 is secured to the male luer connector 920, the skirt 910 may be collapsed to transition it to the closed mode. When in the closed mode, the skirt 910 may surround a portion of the catheter hub 214 to secure the catheter 210 to the device.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A vascular access site management system for transfer of fluid to and/or from a patient, the vascular access site management system comprising:
   a stabilization body having a first portion and a base portion, the first portion having an inlet, an outlet configured to be slidably coupled to a fluid channel surface of a vascular access device inserted into the patient's vasculature, and an internal fluid path extending through at least a portion of the stabilization body and between the inlet and outlet, the internal fluid path having a fluid path longitudinal axis, the stabilization body also having a locking mechanism rotatably coupled to the stabilization body such that the locking mechanism may rotate about the first portion, the locking mechanism configured to independently rotate and secure the stabilization body to the vascular access device inserted into the patient's vasculature, the base portion having a stabilization surface located on an underside of the base portion and configured to stabilize the vascular access site management system when placed upon the patient, the base portion extending from the first portion between the inlet and the outlet such that the stabilization surface is oriented at an angle with respect to the fluid path longitudinal axis; and
   a flow housing having a sleeve portion having a first longitudinal axis and a pathway portion having a second longitudinal axis and extending from the sleeve portion, the first longitudinal axis not parallel to the second longitudinal axis, the pathway portion having a flow path extending through at least a portion of the pathway portion, the sleeve portion, the flow path and the internal fluid path defining a system fluid path through the vascular access site management system, the sleeve portion rotatably coupled to the stabilization body such that the flow housing is rotatable with respect to the stabilization body and between a first position and at least a second position, an inlet of the pathway portion being a first distance from the stabilization surface when in the first portion and a second distance from the stabilization surface when in the second position, the second distance being shorter than the first distance, the stabilization surface configured to be placed on the patient after rotation of the locking mechanism to secure the stabilization body to the vascular access device and configured to remain in place on the patient during rotation of the sleeve portion, thereby restricting rotational and translational movement of the vascular access device.

2. The vascular access site management system according to claim 1, wherein the flow path is fluidly disconnected from the inlet of the stabilization body when in the first position, the flow path being fluidly connected to the inlet of the stabilization body when in the second position.

3. The vascular access site management system according to claim 1, further comprising an o-ring located between at least a portion of the stabilization body and at least a portion of the flow housing.

4. The vascular access site management system according to claim 1, further comprising a first securement portion located on at least a portion of an underside of the stabilization surface, the first securement portion configured to secure the vascular access site management system to the patient.

5. The vascular access site management system according to claim 4, further comprising a second securement portion located on at least a second portion of an underside of the stabilization surface, the second securement portion configured to further secure the vascular access site management system to the patient.

6. The vascular access site management system according to claim 5, wherein the first securement portion includes a first tack adhesive and the second securement portion includes a second tack adhesive, the second tack adhesive being stronger than the first tack adhesive.

7. The vascular access site management system according to claim 6, wherein the first securement portion has a first liner covering the first tack adhesive and configured to be removed prior to securing the vascular access site management system to the patient, the second securement portion has a second liner covering the second tack adhesive and configured to be removed prior to securing the vascular access site management system to the patient.

8. The vascular access site management system according to claim 4, wherein the first securement portion includes at least one gripping and/or conforming structure.

9. The vascular access site management system according to claim 1, wherein the angle is between 5 degrees and 10 degrees.

10. The vascular access site management system according to claim 1, further comprising a valve mechanism located in the internal fluid path, the valve mechanism configured to selectively prevent and allow fluid flow through the internal fluid path.

11. The vascular access site management system according to claim 10, wherein the stabilization body includes an inlet body and an outlet body, the valve mechanism positioned between the inlet body and outlet body.

12. The vascular access site management system according to claim 11, wherein the valve mechanism is a two way pressure activated valve.

13. The vascular access site management system according to claim 12, wherein the valve mechanism is configured to deform in a presence of a forward pressure within the internal fluid path, thereby allowing fluid flow around the valve mechanism from the inlet to the outlet.

14. The vascular access site management system according to claim 13, wherein the outlet body includes a plurality of support arms supporting the valve mechanism within the stabilization body, the valve mechanism configured to deform over the plurality of support arms in the presence of the forward pressure.

15. The vascular access site management system according to claim 12, wherein the valve mechanism includes a slit extending through the valve mechanism, the slit configured to open in the presence of a back pressure within the internal fluid path, thereby allowing fluid flow through the slit and from the outlet to the inlet.

16. The vascular access site management system according to claim 15, wherein the back pressure required to open the slit is above a venous pressure of the patient.

17. The vascular access site management system according to claim 1, further comprising a tube having a first end and a second end, the first end fluidly connected to the flow path of the pathway portion.

18. The vascular access site management system according to claim 17, further comprising a female luer connector located at the second end of the tube.

19. The vascular access site management system according to claim 1, wherein an inlet of the flow path within the pathway portion is configured to fluidly connect to a medical implement.

20. The vascular access site management system according to claim 1, wherein the stabilization body includes a vein relief zone configured to reduce pressure over a vein of the patient when the vascular access site management system is on the patient.

21. The vascular access site management system according to claim 20, wherein the vein relief zone includes an adhesive portion, the adhesive portion configured to lift the patient's skin when the vascular access site management system is on the patient.

22. The vascular access site management system according to claim 20, wherein the vein relief zone is axially aligned with the outlet of the stabilization body.

23. The vascular access site management system according to claim 1, wherein the outlet of the stabilization body is a male luer.

24. The vascular access site management system according to claim 23, wherein the male luer is configured to connect to a catheter.

25. The vascular access site management system according to claim 1, wherein the stabilization body includes at least one protrusion extending from a surface of the stabilization body, the flow housing having at least one recess and configured to snap over the at least one protrusion such that the at least one protrusion enters the at least one recess, thereby axially securing the flow housing to the stabilization body.

* * * * *

UNITED STATES PATENT AND TRADEMARK OFFICE
CERTIFICATE OF CORRECTION

PATENT NO. : 11,013,902 B2
APPLICATION NO. : 16/298501
DATED : May 25, 2021
INVENTOR(S) : Todd M. Chelak et al.

It is certified that error appears in the above-identified patent and that said Letters Patent is hereby corrected as shown below:

In the Claims

In Claim 1 (Column 25, Lines 41-44), please replace "the stabilization body also having a locking mechanism rotatably coupled to the stabilization body such that the locking mechanism may rotate about the first portion," with --the stabilization body also having a locking mechanism rotatably coupled to the stabilization body such that the locking mechanism rotates about the first portion,--

And

In Claim 1 (Column 25, Line 67 & Column 26, Lines 1-4), please replace "an inlet of the pathway portion being a first distance from the stabilization surface when in the first portion and a second distance from the stabilization surface when in the second position," with --an inlet of the pathway portion being a first distance from the stabilization surface when in the first position and a second distance from the stabilization surface when in the second position,--

Signed and Sealed this
Sixteenth Day of August, 2022

Katherine Kelly Vidal
*Director of the United States Patent and Trademark Office*